US012570684B2

(12) United States Patent
Kurosu et al.

(10) Patent No.: US 12,570,684 B2
(45) Date of Patent: Mar. 10, 2026

(54) DPAGT1 INHIBITORS OF CAPURAMYCIN ANALOGUES AND THEIR ANTIMIGRATORY ACTIVITIES OF SOLID TUMORS

(71) Applicants: UNIVERSITY OF TENNESSEE RESEARCH FOUNDATION, Knoxville, TN (US); CALIFORNIA INSTITUTE OF TECHNOLOGY, Pasadena, CA (US)

(72) Inventors: Michio Kurosu, Knoxville, TN (US); Katsuhiko Mitachi, Knoxville, TN (US); William M. Clemons, Pasadena, CA (US)

(73) Assignees: University of Tennessee Research Foundation, Knoxville, TN (US); California Institute of Technology, Pasadena, CA (US)

( * ) Notice: Subject to any disclaimer, the term of this patent is extended or adjusted under 35 U.S.C. 154(b) by 449 days.

(21) Appl. No.: 18/013,403

(22) PCT Filed: Jun. 30, 2021

(86) PCT No.: PCT/US2021/039826
§ 371 (c)(1),
(2) Date: Dec. 28, 2022

(87) PCT Pub. No.: WO2022/006231
PCT Pub. Date: Jan. 6, 2022

(65) Prior Publication Data

US 2023/0340006 A1 Oct. 26, 2023

Related U.S. Application Data

(60) Provisional application No. 63/046,103, filed on Jun. 30, 2020.

(51) Int. Cl.
*C07H 19/067* (2006.01)
*A61K 45/06* (2006.01)
*C07H 19/06* (2006.01)

(52) U.S. Cl.
CPC .......... *C07H 19/067* (2013.01); *A61K 45/06* (2013.01)

(58) Field of Classification Search
CPC ....... C07H 19/067; C07H 19/06; A61K 45/06
USPC .......... 514/43
See application file for complete search history.

(56) References Cited

U.S. PATENT DOCUMENTS

2003/0171330 A1 9/2003 Hotoda et al.

OTHER PUBLICATIONS

International Search Report and Written Opinion in corresponding International Application No. PCT/US2021/039826, dated Nov. 26, 2021, 10 pages.
Mitachi et al. "SemiSynthesis of an Anticancer DPAGT1 Inhibitor from a Muraymycin Biosynthetic Intermediate", Org Lett. 2019. 21(4), pp. 876-879, especially: p. 6.
Siricilla et al. "Discovery of a Capuramycin Analog that Kills Non-replicating *Mycobacterium uberculosis* and Its Synergistic Effects with Translocase I Inhibitors", J Antibiot (Tokyo). 2015, 68(4): pp. 271-278.
Mitachi et al. "DPAGT1 Inhibitors of Capuramycin Analogues and Their Antimigmtory Activities of Solid Tumors", J Med Chem. Sep. 2020. 63(19): p. 10855-10878.

*Primary Examiner* — Scarlett Y Goon
*Assistant Examiner* — Hoi Yan Lee
(74) *Attorney, Agent, or Firm* — Fish IP Law, LLP

(57) ABSTRACT

Provided herein are compounds and methods of using these compounds to treat disorders related to DPAGT1 function, including cancer and bacterial infections.

18 Claims, 11 Drawing Sheets

UDP-GlucNAc

Dolichol-P-P-GlcNAc (*e.g.* $C_{85-105}$)

Asn (N)

Asn (N)

*N*-Glycans glycosyltransferases

- >50% of proteins modified with N-glycans in cancer cells
  Certain cancer cells increase expression of β1, 6-branched *N*-linked glycans D: Western blotting assay for Snail (SiHa)

A: E-Cadherin (PD002)
PBS
CPPB 0.05 μM
CPPB 0.2 μM
CPPB 2.0 μM
CPPB 20 μM
B: E-Cadherin (PANC-1)
PBS
CPPB 0.05 μM
CPPB 0.2 μM
CPPB 2.0 μM
CPPB 20 μM
C: E-Cadherin (HCT-116)
PBS
CPPB 0.05 μM
CPPB 0.2 μM
CPPB 2.0 μM
CPPB 20 μM

DPAGT1 INHIBITORS OF CAPURAMYCIN ANALOGUES AND THEIR ANTIMIGRATORY ACTIVITIES OF SOLID TUMORS

RELATED APPLICATIONS

This application claims priority to U.S. Provisional Application No. 63/046,103 filed Jun. 30, 2020, the content of which is hereby incorporated by reference in its entirety.

STATEMENT REGARDING FEDERALLY SPONSORED RESEARCH

This invention was made with government support under Grant No. GM114611 awarded by the National Institutes of Health. The government has certain rights in the invention.

BACKGROUND

N-acetylglucosamine-phosphotransferase) (DPAGT1) is an enzyme that catalyzes the first step in the dolichol-linked oligosaccharide pathway for glycoprotein biosynthesis. This protein is an integral membrane protein of the endoplasmic reticulum. Several solid cancers, including pancreatic cancers, require high DPAGT1 expression in order for cancer progression. Whereas tunicamycin, a nucleoside antibiotic, has been shown to inhibit DPAGT1, its non-selective activity is toxic to healthy cells. Capuramycin, another nucleoside antibiotic, displays narrow spectrum of antibacterial activity by targeting bacterial translocase I (MraY), but not DPAGT1. Capuramycin is less toxic than tunicamycin.

Therefore, there remains a need for DPAGT1-selective inhibitors to prevent cancer progression.

SUMMARY

Provided herein are compounds and methods of using these compounds to treat disorders related to DPAGT1 function, including cancer and bacterial infections.

In an aspect, provided herein is a compound of Formula I:

(I)

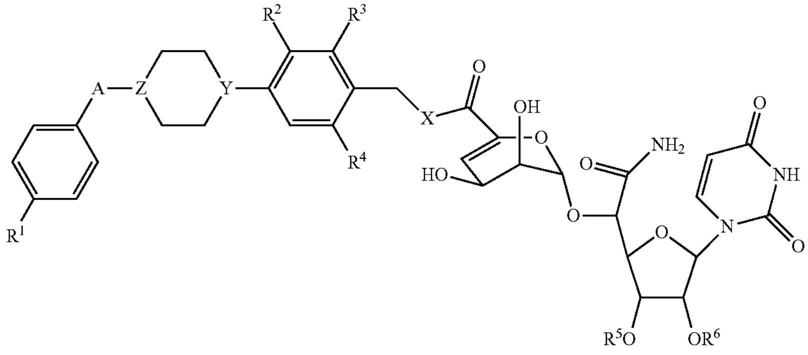

or a pharmaceutically acceptable salt thereof, wherein the variables are defined herein.

In an embodiment, the compound of Formula I is a compound of Formula II:

(II)

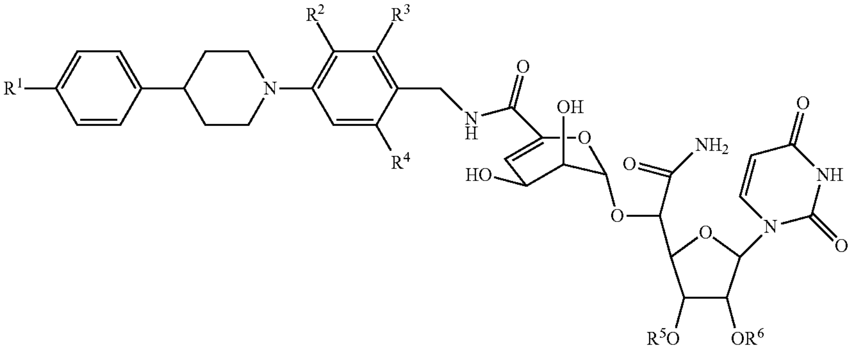

or a pharmaceutically acceptable salt thereof.

In another embodiment, the compound of Formula I is a compound of Formula III:

(III)

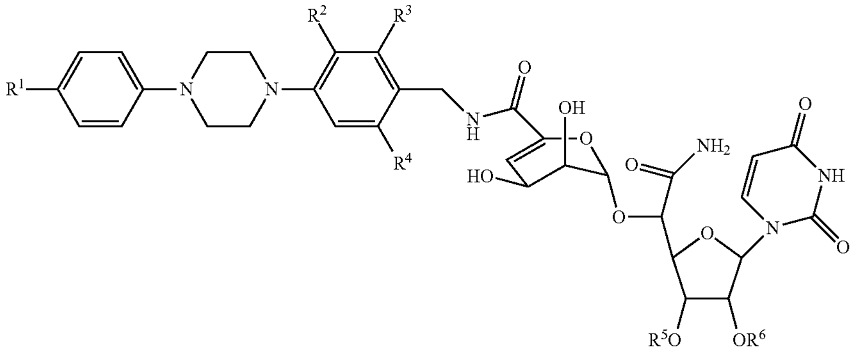

or a pharmaceutically acceptable salt thereof.

In yet another embodiment, the compound of Formula I is a compound of Formula IV:

(IV)

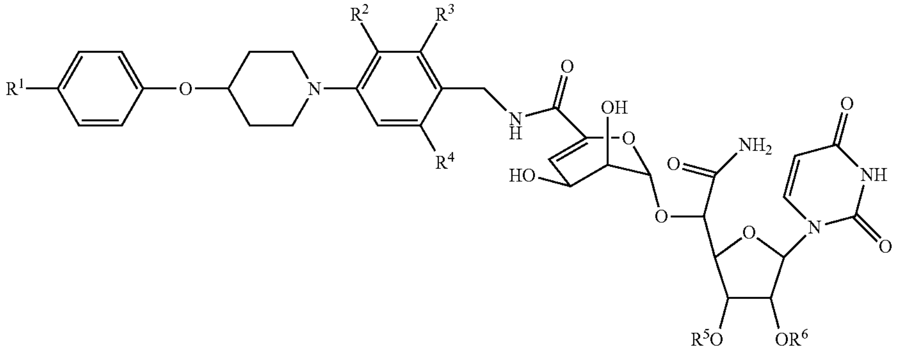

or a pharmaceutically acceptable salt thereof.

In another aspect, provided herein is a compound of Formula V:

(V)

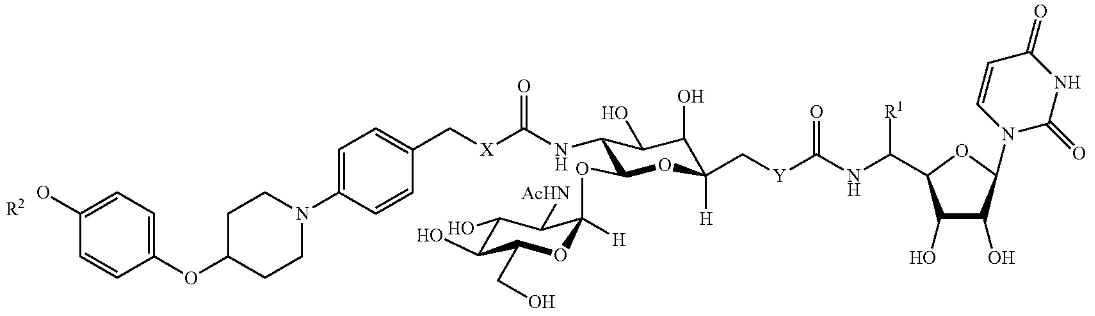

or a pharmaceutically acceptable salt thereof.

In yet another aspect, provided herein is a compound of Formula VI:

(VI)

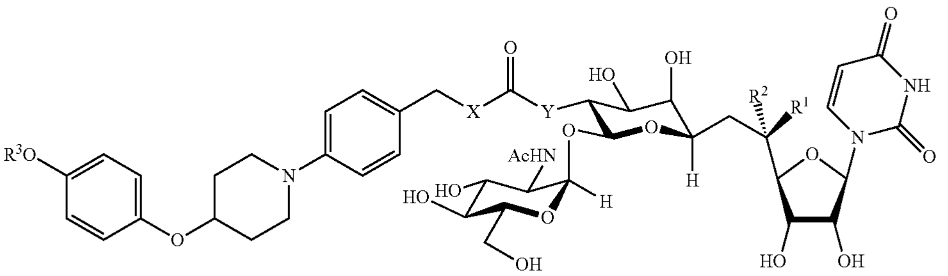

or a pharmaceutically acceptable salt thereof.

In another aspect, provided herein is a method of inhibiting dolichyl-phosphate N-acetylglucosaminephosphotransferase (DPAGT1) in a subject in need thereof, comprising administering to the subject a therapeutically effective amount of any of the compounds disclosed herein, or a pharmaceutically acceptable salt thereof.

In still another aspect, provided herein is a method of treating cancer in a subject in need thereof, comprising administering to the subject a therapeutically effective amount of any of the compounds disclosed herein, or a pharmaceutically acceptable salt thereof.

DETAILED DESCRIPTION

Capuramycin is a nucleoside antibiotic that has a narrow-spectrum of activity against Gram-positive bacteria including *Mycobacterium tuberculosis* (Mtb) (Siricilla, S., et al., *J. Antibiot.* 2015, 68, 271-278). To date, medicinal chemistry efforts on capuramycin have been focused on developing a new tuberculosis (TB) drug. New capuramycin analogues have been synthesized to improve bacterial phospho-MurNAc-pentapeptide translocase I (MraY and MurX for *Mycobacterium* spp.) enzyme as well as antimycobacterial activities (Kurosu, M. et al., *Heterocycles* 2009, 77, 217-225). Somewhat recently, the anti-*Clostridioides difficile* (formerly *Clostridium difficile*) activity of a capuramycin analogue has been reported (Moore, J. H., et al., *J. Antimicrob Chemother.* 2016, 71, 1300-1306). Capuramycin is a specific inhibitor of MraY with the $IC_{50}$ value of 0.15 μM, however, some other nucleoside antibiotics (e.g., muraymycin A1 and tunicamycins) display activity against MraY, WecA (polyprenyl phosphate-GlcNAc-1-phosphate transferase), and its human homologue, DPAGT1 (N-acetylglucosaminephosphotransferase 1)-type phosphotransferases (Mitachi, K., et al. *J. Am. Chem. Soc.* 2016, 138, 12975-12980). MraY is an essential enzyme for growth of the vast majority of bacteria that catalyzes the transformation from UDP-MurNAc-pentapeptide (Park's nucleotide) to prenyl-MurNAc-pentapeptide (lipid I) (van Heijenoort, J. *Microbiol. Mol. Biol. Rev.* 2007, 71, 620-635). WecA catalyzes the transformation from UDP-GlcNAc to decaprenyl-P-P-GlcNAc, the first membrane-anchored glycophospholipid that is responsible for the biosynthesis of mycolylarabinogalactan in *Mycobacterium tuberculosis* (Mtb). WecA is an essential enzyme for the growth of Mtb and some other bacteria.

Figure 1:
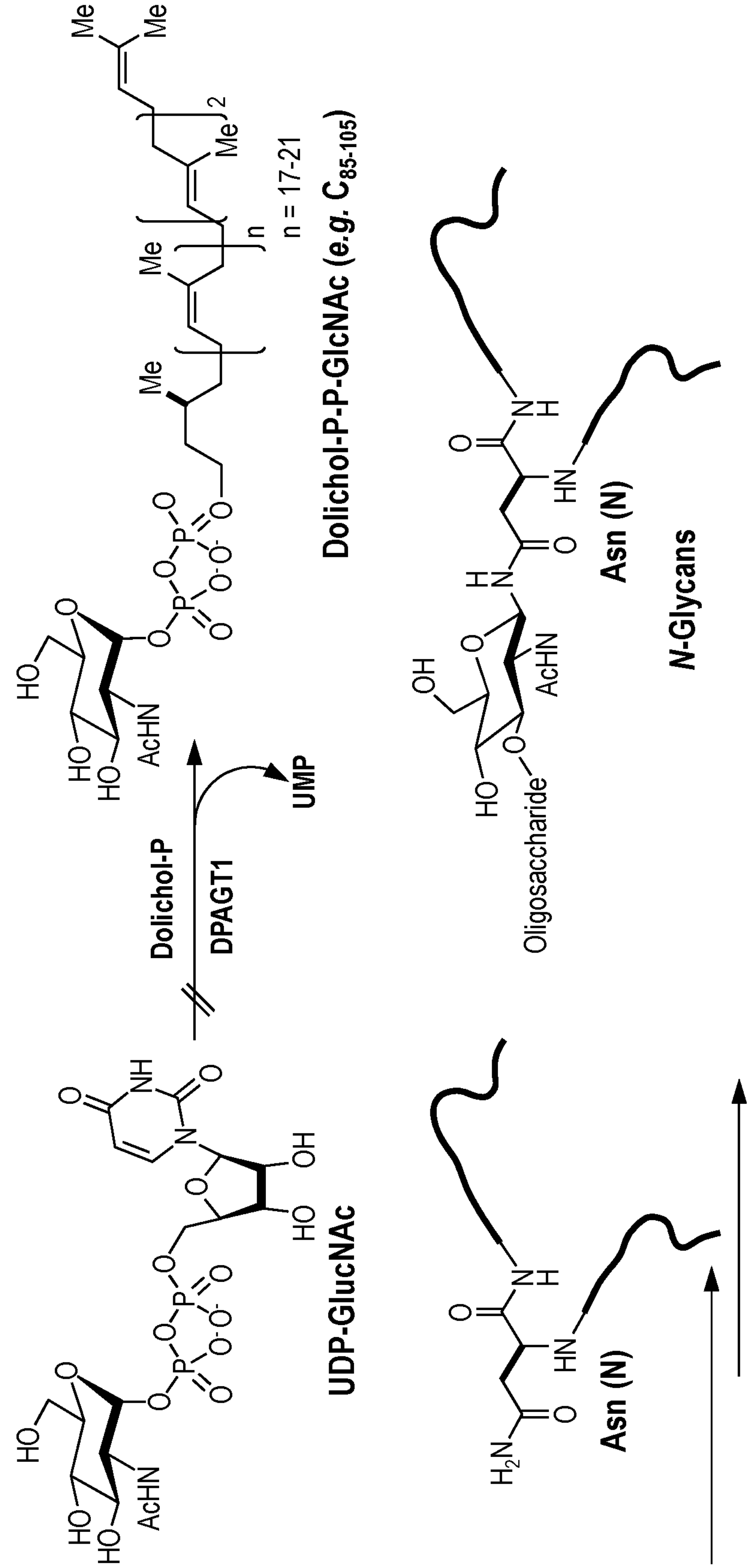
FIG. 1 shows DPAGT1 in N-glycan biosynthesis.

Biochemical studies of WecA enzyme are hampered by lack of selective inhibitor molecules. Tunicamycin shows inhibitory activity against these phosphotransferases with the $IC_{50}$ values of 3.38 μM (MraY/MurX), 0.15 μM (WecA), and 2.5 μM (DPAGT1). CPZEN-45, an antimycobacterial MraY inhibitor, was reported to exhibit WecA inhibitory activity ($IC_{50}$~0.058 μg/mL). It has been shown that 2'O-methyl capuramycin does not exhibit MraY/MurX inhibitory activity, but displays a strong WecA inhibitory activity ($IC_{50}$~0.060 μM). In vitro cytotoxicity of tunicamycin has been documented in a number of articles (Zhong, J-T., et al. *Tumor Biol.* 2017, 39). Acute toxicity of tunicamycin due to its narrow therapeutic window ($LDs_{50}$: 2.0 mg/kg, LD100: 3.5 mg/kg mice, IP) discourages scientists from developing tunicamycin for new antibacterial, antifungal, and anti-cancer agents. A large number of scientists believe that cytotoxicity of tunicamycin is attributable to its interaction with DPAGT1, which catalyzes the first and rate limiting step in the dolichol-linked oligosaccharide pathway in N-linked glycoprotein biosynthesis (FIG. 1).

Provided herein are novel DPAGT1 inhibitors that exhibit in vitro anti-invasion and anti-metastasis activity.

Definitions

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, "pharmaceutical combination" or "combination" refers to formulations of the separate compounds with or without instructions for combined use or to combination products. The combination compounds may thus be entirely separate pharmaceutical dosage forms or in pharmaceutical compositions that are also sold independently of each other and where just instructions for their combined use are provided in the package equipment, e.g., leaflet or the like, or in other information, e.g., provided to physicians and medical staff (e.g. oral communications, communications in writing or the like), for simultaneous or sequential use for being jointly active.

As used herein, the terms "synergy" or "synergistic effect" refer to the effect achieved when the active ingredients, i.e., DPAGT1 inhibitor and additional therapeutic agent, used together is greater than the sum of the effects that results from using the compounds separately.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, $—NR(CR'R'')_n—$ includes both $—NR(CR'R'')_n—$ and $—(CR'R'')_nNR—$ and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include $—OCH_2CH_2O—$ and $OCH_2CH_2CH_2O—$. In some embodiments, the two O atoms of a $C_{n-m}$ dialkoxy group may be attached to the same B atom to form a 5- or 6-membered heterocycloalkyl group.

The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments, aryl groups have 6 carbon atoms. In some embodiments, aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The compounds described herein can be asymmetric (e.g., having one or more stereocenters). All stereoisomers, such as enantiomers and diastereomers, are intended unless otherwise indicated. Compounds provided herein that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as 3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds provided herein have the (R)-configuration. In other embodiments, the compounds have the (S)-configuration. In compounds with more than one chiral centers, each of the chiral centers in the compound may be independently (R) or (S), unless otherwise indicated.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds provided herein can also include all isotopes of atoms occurring in the intermediates or final compounds.

Isotopes include those atoms having the same atomic number but different mass numbers. For example, isotopes of hydrogen include tritium and deuterium. One or more constituent atoms of the compounds provided herein can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound" as used herein is meant to include all stereoisomers, geometric isomers, tautomers and isotopes of the structures depicted. The term is also meant to refer to compounds provided herein, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds provided herein, or salts thereof, are substantially isolated. By "substantially isolated" is meant that the compound is at least partially or substantially separated from the environment in which it was formed or detected. Partial separation can include, e.g., a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The phrase "pharmaceutically acceptable" is employed herein to refer to those compounds, materials, compositions and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The present disclosure also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the non-toxic salts of the parent compound formed, e.g., from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences,* $17^{th}$ Ed., (Mack Publishing Company, Easton, 1985), p. 1418, Berge et al., *J. Pharm. Sci.,* 1977, 66 (1), 1-19 and in Stahl et al., *Handbook of Pharmaceutical Salts: Properties, Selection, and Use*, (Wiley, 2002). In some embodiments, the compounds described herein include the N-oxide forms.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

Compounds

In an aspect, provided herein is a compound of Formula I:

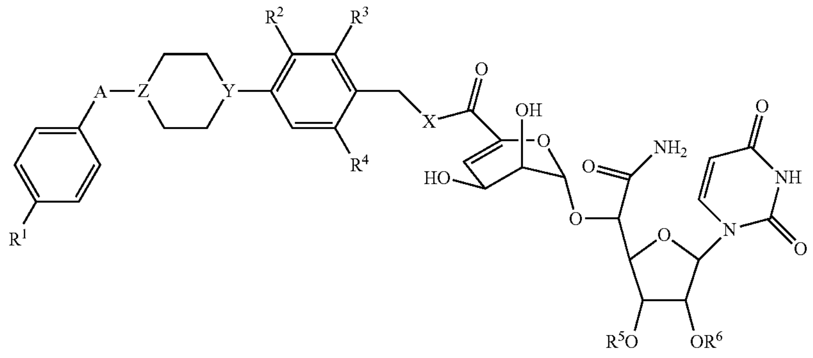

(I)

or a pharmaceutically acceptable salt thereof;

wherein

X is NH, O, or $-(CH_2)_m-$;

Y is CH or N;

Z is CH or N;

A is absent, O, or NH;

$R^1$ is $OR^7$ or $-(CH_2)_nNHR^7$;

$R^2$ is H or halo;

$R^3$ is selected from the group consisting of H, halo, $C_1$-$C_6$ alkyl, $C_2$-$C_6$ alkenyl, $C_2$-$C_6$ alkynyl, $C_1$-$C_6$ alkoxy, and $C_1$-$C_6$ haloalkyl;

$R^4$ is H or halo;

$R^5$ and $R^6$ are each independently selected from the group consisting of H, $C_1$-$C_6$ alkyl, and $C(O)C_1$-$C_6$ alkyl;

$R^7$ is selected from the group consisting of H, $C_1$-$C_6$ alkyl, $C_1$-$C_6$ haloalkyl, $C_6$-$C_{10}$ aryl, and 5-10 membered heteroaryl; wherein aryl and heteroaryl are each optionally substituted one, two, or three times with $OC_1$—$C_6$ haloalkyl; and m and n are, independently at each occurrence, 0, 1, 2, or 3.

In an embodiment, the compound of Formula I is a compound of Formula II:

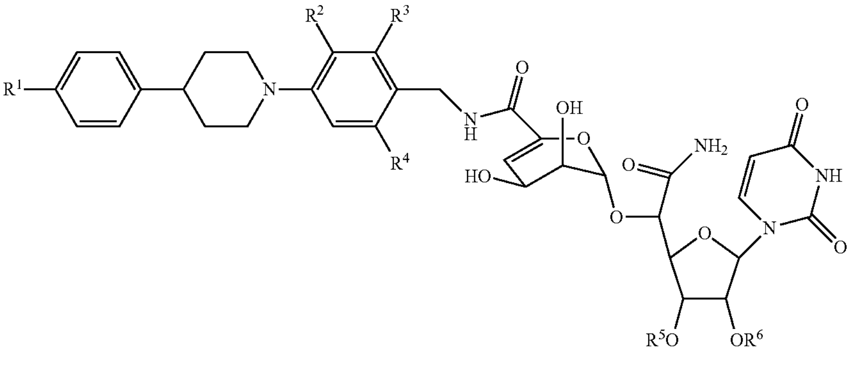

(II)

or a pharmaceutically acceptable salt thereof.

In another embodiment, the compound of Formula I is a compound of Formula III:

(III)

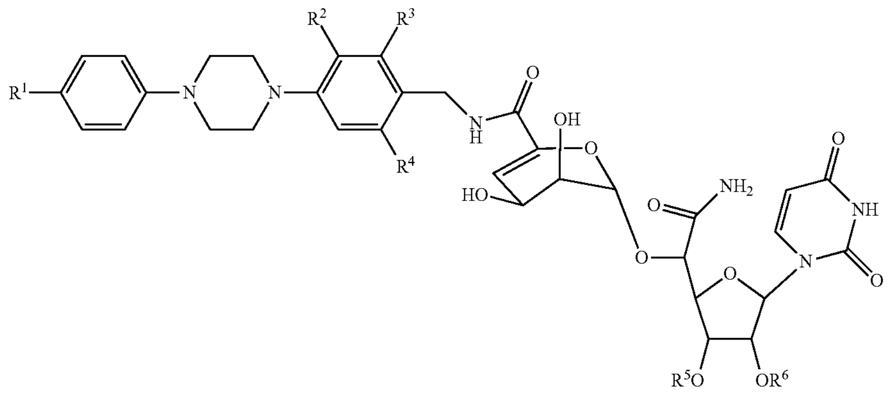

or a pharmaceutically acceptable salt thereof.

In yet another embodiment, the compound of Formula I is a compound of Formula IV:

(IV)

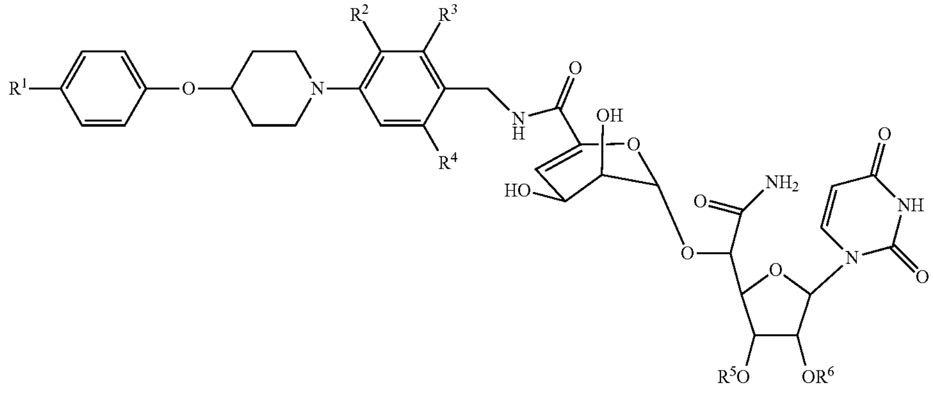

or a pharmaceutically acceptable salt thereof.

In still another embodiment, $R^1$ is $OR^7$. In an embodiment, $R^1$ is —$(CH_2)nNHR^7$. In another embodiment, $R^7$ is selected from the group consisting of $C_1$-$C_6$ alkyl, $C_1$-$C_6$ haloalkyl, and phenyl, wherein phenyl is optionally substituted one time with $OC_1$—$C_6$ haloalkyl. In yet another embodiment, $R^7$ is selected from the group consisting of methyl, ethyl, $C_3$ alkyl, $C_4$ alkyl, $CF_3$, and phenyl-$OCF_3$.

In an embodiment, $R^2$ is H. In another embodiment, $R^2$ is fluoro.

In yet another embodiment, $R^3$ is selected from the group consisting of H, fluoro, methyl, methoxy, $C_2$ alkenyl, and $C_2$ alkynyl. In still another embodiment, $R^3$ is H.

In an embodiment, $R^4$ is H. In another embodiment, $R^4$ is fluoro.

In yet another embodiment, $R^5$ is methyl. In still another embodiment, $R^6$ is H or methyl. In an embodiment, $R^6$ is H.

In another embodiment, the compound of Formula I is CPPB:
(CPPB)
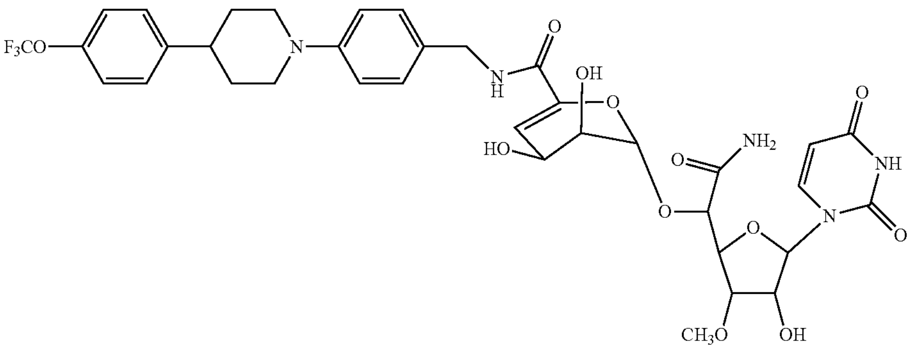
or a pharmaceutically acceptable salt thereof.
In yet another embodiment, the compound of Formula I is CPPB1:
(CPPB1)
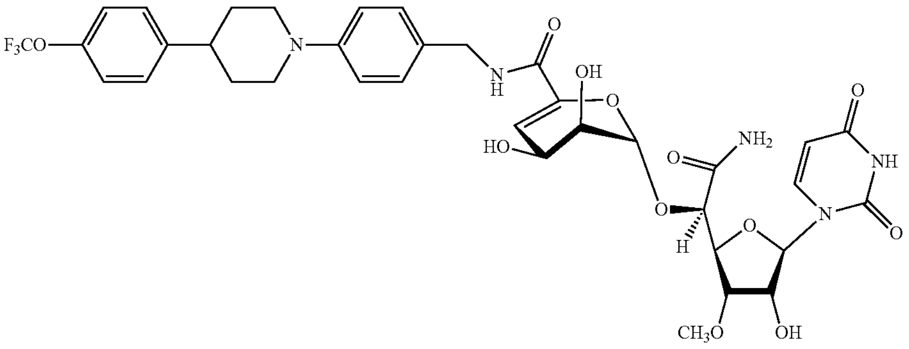
or a pharmaceutically acceptable salt thereof.
In another aspect, provided herein is a compound of Formula V:
(V)
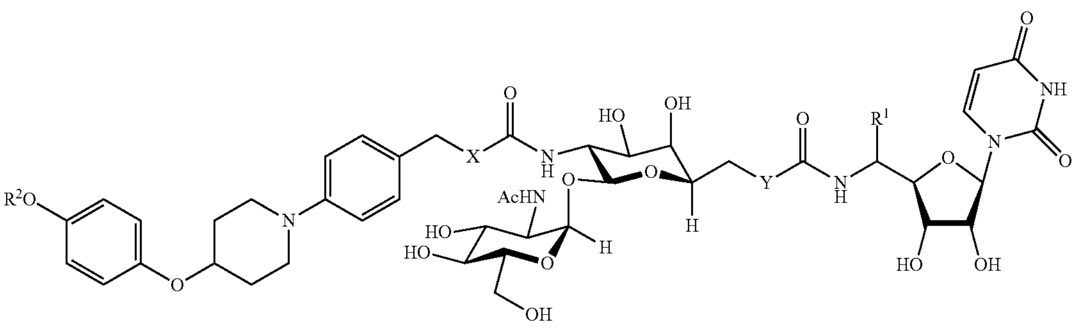
or a pharmaceutically acceptable salt thereof;

wherein

X and Y are independently O or NH;

$R^1$ is selected from the group consisting of H, OH, $C(O)NH_2$, $CO_2H$, C(O)H, and C(O)halo; and $R^2$ is selected from the group consisting of H, $C_1$-$C_6$ alkyl, $C_1$-$C_6$ haloalkyl, $C_6$-$C_{10}$ aryl, and 5-10 membered heteroaryl.

In an embodiment, X is O. In another embodiment, X is NH. In yet another embodiment Y is O. In still another embodiment, Y is NH.

In an embodiment, $R^1$ is $C(O)NH_2$. In another embodiment, $R^2$ is $C_1$-$C_6$ haloalkyl.

In another embodiment, the compound of Formula V is (Compound A)

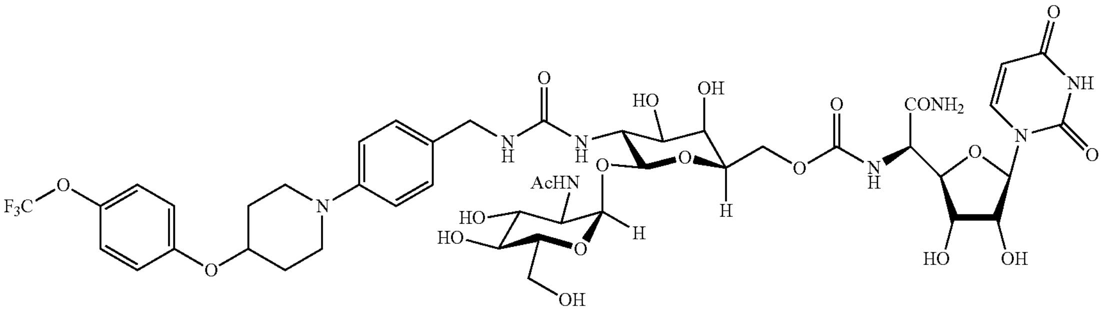

or (Compound B)

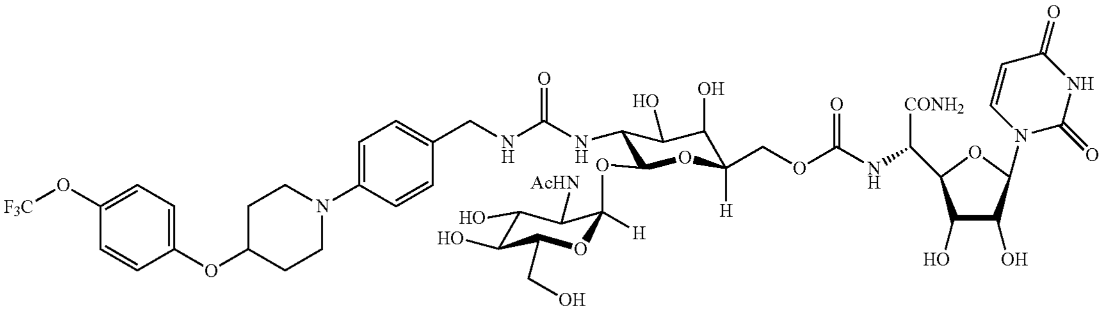

or a pharmaceutically acceptable salt thereof.

In yet another aspect, provided herein is a compound of Formula VI:

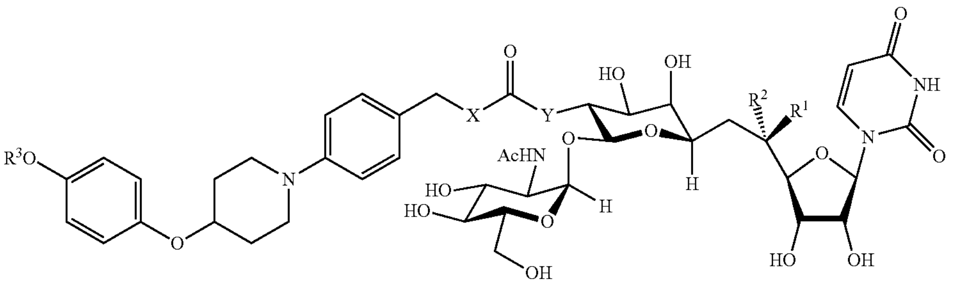

(VI)

or a pharmaceutically acceptable salt thereof;
wherein

X and Y are independently O or NH;

$R^1$ and $R^2$ are each independently selected from H and OH; and $R^3$ is selected from the group consisting of H, $C_1$-$C_6$ alkyl, $C_1$-$C_6$ haloalkyl, $C_6$-$C_{10}$ aryl, and 5-10 membered heteroaryl.

In an embodiment, X and Y are NH. In another embodiment, X is NH and Y is O. In yet another embodiment, X is O and Y is NH.

In still another embodiment, $R^3$ is $C_1$-$C_6$ haloalkyl.

In an embodiment, the compound of Formula VI is selected from the group consisting of:

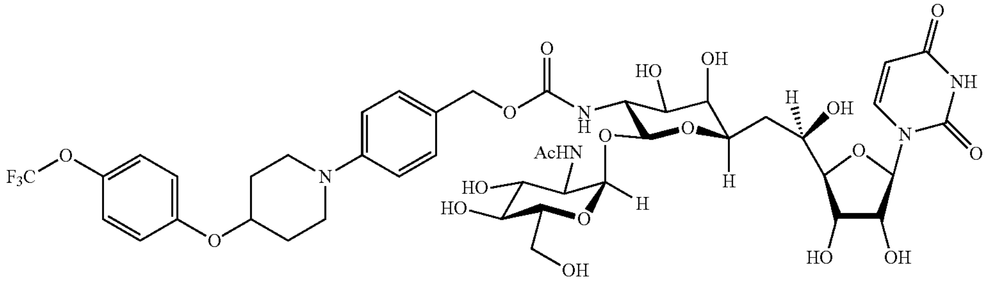

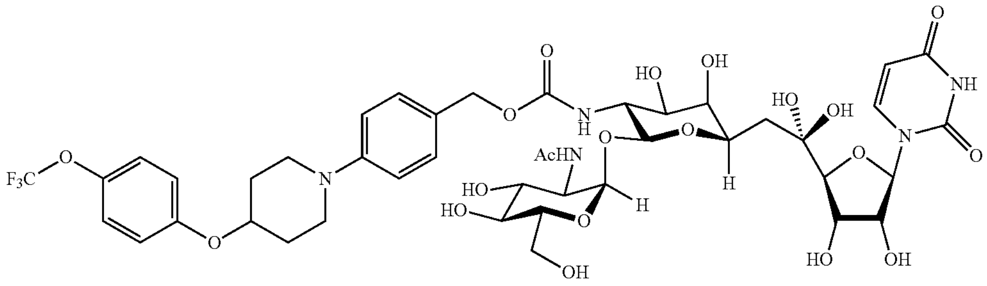

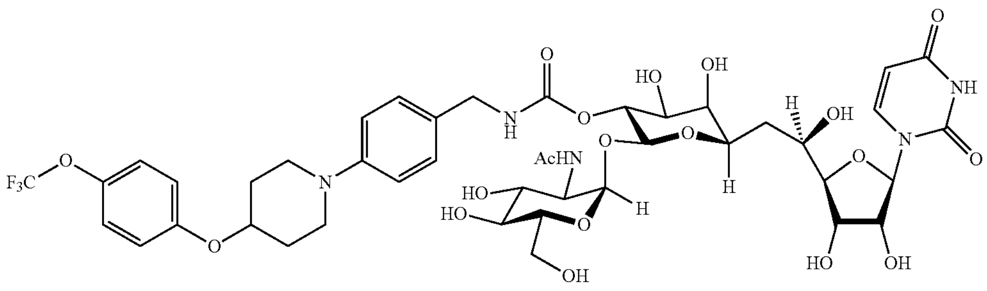

-continued

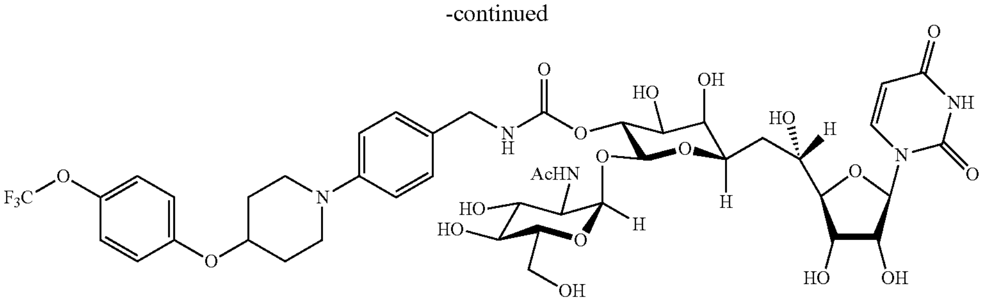

or a pharmaceutically acceptable salt thereof.

In another aspect, provided herein is a pharmaceutical composition comprising a compound disclosed herein, and at least one pharmaceutically acceptable carrier.

In an embodiment, the pharmaceutical composition further comprises an additional therapeutic agent.

In another embodiment, the additional therapeutic agent is selected from the group consisting of paclitaxel, tunicamycin, capuramycin, erlotinib, capecitabine, fluorouracil, and gemcitabine. In yet another embodiment, the additional therapeutic agent is paclitaxel.

Methods of Treatment

In yet another aspect, provided herein is a method of inhibiting dolichyl-phosphate N-acetylglucosaminephosphotransferase (DPAGT1) in a subject in need thereof, comprising administering to the subject a therapeutically effective amount of a compound disclosed herein or a pharmaceutical composition comprising a compound disclosed herein.

In still another aspect, provided herein is a method of treating cancer in a subject in need thereof, comprising administering to the subject a therapeutically effective amount of a compound of the present disclosure or a pharmaceutical composition comprising a compound disclosed herein.

In an embodiment, the cancer is selected from hematological cancers, sarcomas, lung cancers, brain cancers, gastrointestinal cancers, genitourinary tract cancers, liver cancers, bone cancers, nervous system cancers, gynecological cancers, and skin cancers.

In another embodiment, the lung cancer is selected from non-small cell lung cancer (NSCLC), small cell lung cancer, bronchogenic carcinoma, squamous cell bronchogenic carcinoma, undifferentiated small cell bronchogenic carcinoma, undifferentiated large cell bronchogenic carcinoma, adenocarcinoma, bronchogenic carcinoma, alveolar carcinoma, bronchiolar carcinoma, bronchial adenoma, chondromatous hamartoma, mesothelioma, pavicellular and non-pavicellular carcinoma, bronchial adenoma, and pleuropulmonary blastoma.

In yet another embodiment, the lung cancer is non-small cell lung cancer (NSCLC). In still another embodiment, the lung cancer is adenocarcinoma.

In an embodiment, the gastrointestinal cancer is selected from esophagus squamous cell carcinoma, esophagus adenocarcinoma, esophagus leiomyosarcoma, esophagus lymphoma, stomach carcinoma, stomach lymphoma, stomach leiomyosarcoma, exocrine pancreatic carcinoma, pancreatic ductal adenocarcinoma, pancreatic insulinoma, pancreatic glucagonoma, pancreatic gastrinoma, pancreatic carcinoid tumors, pancreatic vipoma, small bowel adenocarcinoma, small bowel lymphoma, small bowel carcinoid tumors, Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma, colorectal cancer, gall bladder cancer, and anal cancer.

In an embodiment, the gastrointestinal cancer is colorectal cancer.

In another embodiment, the brain cancer is selected from acoustic neuroma, astrocytoma, choroid plexus carcinoma, craniopharyngioma, embryonal tumors, ependymoma, glioblastoma, glioma, medulloblastoma, meningioma, oligodendroglioma, pineoblastoma, mixed glioma, mixed glial and neuronal tumors, and primitive neuroectodermal tumors.

In another embodiment, the cancer is a carcinoma. In yet another embodiment, the carcinoma is selected from pancreatic carcinoma, colorectal carcinoma, lung carcinoma, bladder carcinoma, gastric carcinoma, esophageal carcinoma, breast carcinoma, head and neck carcinoma, cervical skin carcinoma, and thyroid carcinoma.

In still another embodiment, the cancer is a hematopoietic malignancy. In an embodiment, the hematopoietic malignancy is selected from multiple myeloma, acute myelogenous leukemia, and myeloproliferative neoplasms.

In another embodiment, the cancer is a neoplasm. In yet another embodiment, the neoplasm is glioblastoma or sarcomas.

In an embodiment, the cancer is selected from the group consisting of hematological cancers, sarcomas, lung cancers, gastrointestinal cancers, genitourinary tract cancers, liver cancers, bone cancers, nervous system cancers, gynecological cancers, and skin cancers.

In an embodiment, the cancer is selected from the group consisting of pancreatic cancer, cervical cancer, colon cancer, ovarian cancer, breast cancer, pancreatic cancer, carcinoma, and adenocarcinoma.

In another embodiment, the cancer is pancreatic cancer. In yet another embodiment, the cancer is a solid tumor.

In an embodiment of the methods, the subject is human.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

EXAMPLES

Example 1: Synthetic Procedures

Scheme 1

A: Synthesis of *iso*-capuramycin (I-CAP)

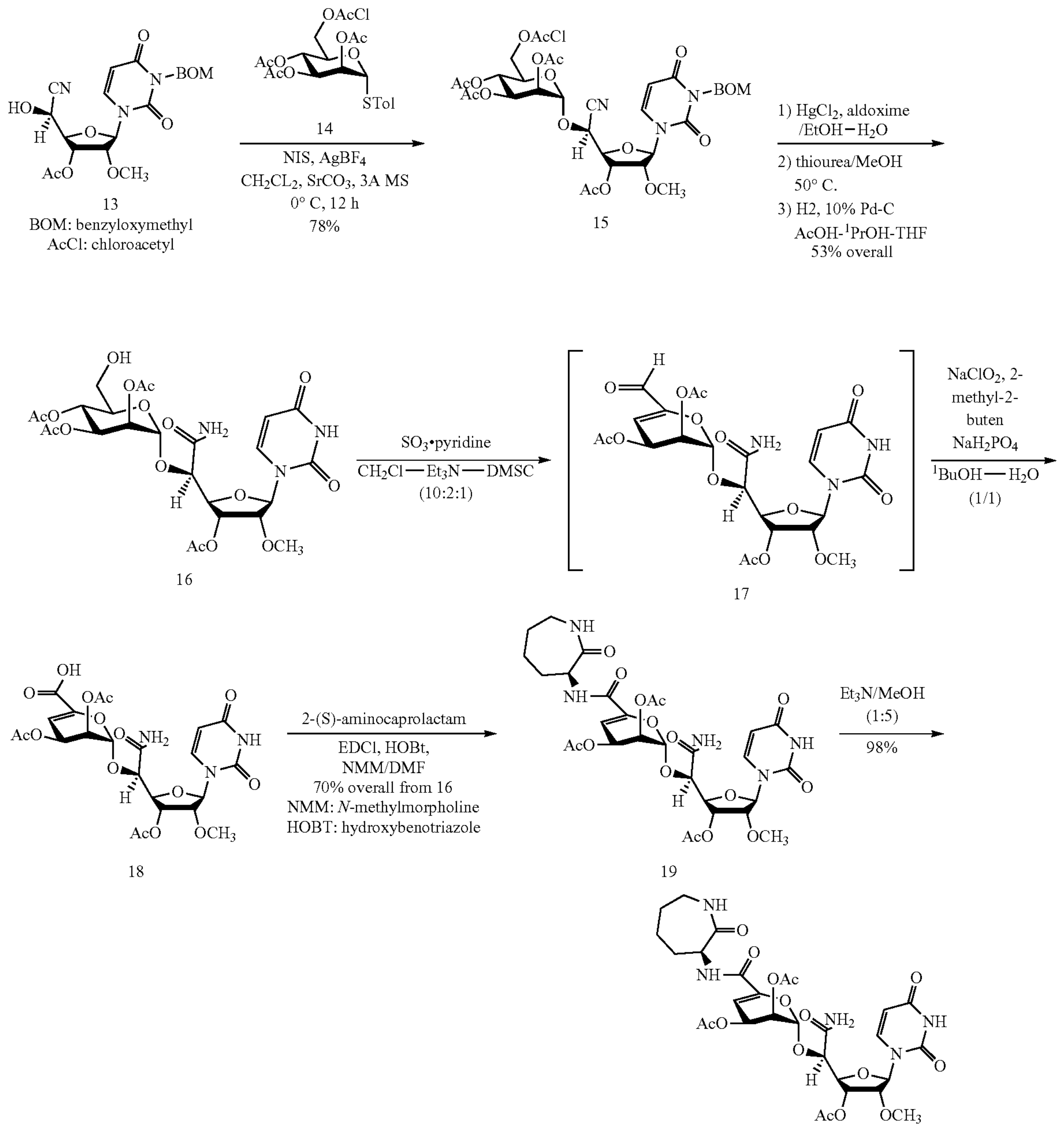

13
BOM: benzyloxymethyl
AcCl: chloroacetyl

14

15

16

17

18

19

I-CAP (3)

-continued

B: Synthesis of demethyl-capuramycin (DM-CAP)

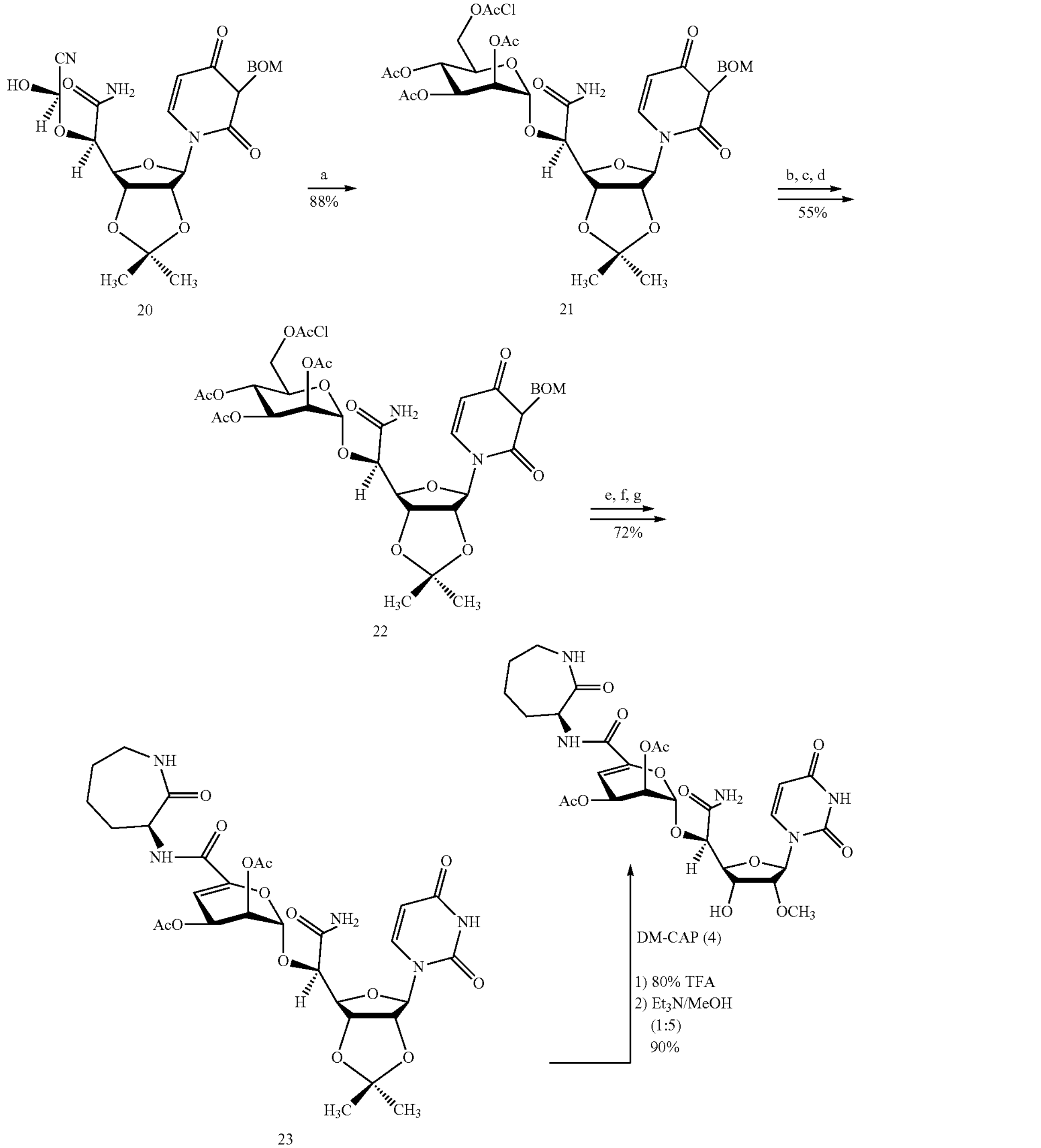

20 21 22 23 a) 14, NIS, AgBF4, SrCO3, 3A MS, CH2CL2, 0° C., 12 h.; b) HgCl2, aldoxime,EtOH—$H_2O$,; c) thiourea, MeOH, 50° C,; d) H2, 10% Pd-C, AcOH-iPrOH-THF,;

The (S)-cyanohydrin (13) was subjected to NIS—$AgBF_4$ promoted α-selective mannosylation with the thioglycoside (14) to yield the α-mannosylated cyanohydrin (15) in 78% yield. The cyano group of 15 was hydrated using $HgCl_2$-aldoxime in aq. EtOH, and the BOM and chloroacetyl groups of the generated amide were deprotected stepwisely: dechloroacetylation with thiourea followed by hydrogenation with 10% Pd—C in AcOH-$^{i}$PrOH-THF provided the C6"-free alcohol 16 in 53% overall yield. Oxidation-elimination reaction of 16 with $SO_3$·pyridine in a solvent system ($CH_2Cl_2$/$Et_3N$/DMSO=10/2/1) provided the α,β-unsaturated aldehyde 17 in quantitative yield (determined by $^1H$ NMR analysis). After all volatiles were removed, the aldehyde 17 was oxidized to the corresponding carboxylic acid 18 by using $NaClO_2$ in the presence of $NaH_2PO_4$ and 2-methyl-2-butene. The resulting carboxylic acid 18 was coupled with (2S)-aminocaprolactam by using a standard peptide-forming reaction condition (HOBt, EDCl, and NMM) to yield the coupling product 19 in 70% overall yield from 16. Saponification of 19 by using $Et_3N$ in MeOH provided I-Cap (3) in quantitative yield. Similarly, dimethyl-capuramycin (DM-CAP) was synthesized in 31% overall yield from the cyanohydrin-acetonide 20.

(2S,3S,4S,5R,6R)-2-((1 S)-((2R,5R)-3-Acetoxy-5-(3-((benzyloxy)methyl)-2,4-dioxo-3,4-dihydropyrimidin-1 (2H)-yl)-4-methoxytetrahydrofuran-2-yl)(cyano)methoxy)-6-((2-chloroacetoxy)methyl)-tetrahydro-2H-pyran-3,4,5-triyl triacetate (15). To a stirred suspension of 13 (0.17 g, 0.38 mmol), 14 (0.37 g, 0.75 mmol), MS 3 Å (0.50 g) and $SrCO_3$ (0.28 g, 1.88 mmol) in $CH_2Cl_2$ (9.4 mL) were added $AgBF_4$ (0.037 g, 0.19 mmol) and NIS (0.25 g, 1.13 mmol) at 0° C. After being stirred for 19 h, the reaction mixture was added $Et_3N$ (1.0 mL) and passed through a silica gel pad (hexanes/EtOAc=1/4). The filtrate was concentrated in vacuo. The crude mixture was purified by silica gel column chromatography (hexanes/EtOAc=2/1 to 1/2) to afford 15 (0.24 g, 78%): $^1$H NMR (400 MHz, Chloroform-d) δ 7.40-7.27 (m, 6H), 6.07 (d, J=4.7 Hz, 1H), 6.00 (d, J=8.2 Hz, 1H), 5.51 (d, J=9.8 Hz, 1H), 5.47 (d, J=9.6 Hz, 1H), 5.37 (dd, J=3.4, 2.0 Hz, 1H), 5.28 (d, J=10.2 Hz, 1H), 5.22-5.15 (m, 2H), 4.84 (d, J=3.2 Hz, 1H), 4.71 (s, 2H), 4.41 (dd, J=5.5, 3.2 Hz, 1H), 4.39-4.35 (m, 1H), 4.33 (d, J=6.0 Hz, 1H), 4.27 (d, J=2.3 Hz, 1H), 4.14 (d, J=1.7 Hz, 2H), 4.03-4.01 (m, 1H), 3.93 (ddd, J=8.9, 5.9, 2.4 Hz, 1H), 3.47 (s, 3H), 2.20 (s, 3H), 2.19 (s, 3H), 2.07 (s, 3H), 2.02 (s, 3H); $^{13}$C NMR (101 MHz, $CDCl_3$) δ 170.20, 169.84, 169.50, 166.92, 162.19, 150.97, 137.75, 137.46, 128.32 (2C), 127.72, 127.69 (2C), 113.96, 103.58, 96.29, 88.68, 80.93, 80.09, 72.30, 70.42, 69.60, 68.46, 67.94, 65.16, 64.35, 63.58, 59.26, 40.61, 31.58, 20.70, 20.66, 20.62, 20.57; HRMS (ESI+) m/z calcd for $C_{35}H_{41}ClN_3O_{17}$ [M+H] 810.2125, found: 810.2151.

(2R,3S,4S,5R,6R)-2-((1R)-1-(2S,5R)-3-Acetoxy-5-(2,4-dioxo-3,4-dihydropyrimidin-1(2H)-yl)-4-methoxy-tetrahydrofuran-2-yl)-2-amino-2-oxoethoxy)-6-(hydroxymethyl) tetrahydro-2H-pyran-3,4,5-triyltriacetate (16). To a stirred solution of 15 (0.24 g, 0.29 mmol) in a 9:1 mixture of EtOH and $H_2O$ (2.9 mL) were added $HgCl_2$ (0.16 g, 0.59 mmol) and acetaldoxime (0.18 mL, 2.9 mmol). After being stirred for 13 h at r.t., the reaction mixture was concentrated in vacuo. The residue was quenched with aq. $NaHCO_3$, and extracted with $CHCl_3$. The combined organic extracts were dried over $Na_2SO_4$ and concentrated in vacuo. The crude product was purified by silica gel column chromatography (hexanes/EtOAc=1/2 to $CHCl_3$/MeOH=96/4) to afford the amide (0.21 g, 87%). To a solution of the amide (0.21 g, 0.26 mmol) in a 1:1 mixture of THF and MeOH (2.6 mL) was added thiourea (0.059 g, 0.77 mmol). After being stirred for 11 h at 50° C., the reaction mixture was concentrated in vacuo. The residue was diluted with $H_2O$ and extracted with $CHCl_3$. The combined organic extracts were dried over $Na_2SO_4$ and concentrated in vacuo. The crude product was purified by silica gel column chromatography ($CHCl_3$/MeOH=98/2 to 97/3 to 96/4) to afford the primary alcohol (0.15 g, 75%). To a stirred solution of the primary alcohol (0.15 g, 0.19 mmol) and AcOH (0.040 mL) in a 1:1 mixture of THF and PrOH (2.0 mL) was added 10% Pd/C (0.12 g) under $N_2$. $H_2$ gas was introduced and the reaction mixture was stirred under $H_2$ atmosphere for 3 h, the solution was filtered through Celite and concentrated in vacuo. The crude product was purified by silica gel column chromatography ($CHCl_3$/MeOH=97/3 to 92/8) to afford 16 (0.10 g, 81%): $^1$H NMR (400 MHz, Chloroform-d) δ 9.08 (brs, 1H), 7.60 (d, J=8.2 Hz, 1H), 6.87 (brs, 1H), 6.12 (brs, 1H), 6.00 (d, J=8.1 Hz, 1H), 5.87 (d, J=3.6 Hz, 1H), 5.55-5.52 (m, 1H), 5.26-5.22 (m, 2H), 5.20 (t, J=6.0 Hz, 1H), 5.00 (d, J=1.7 Hz, 1H), 4.53 (dd, J=6.5, 2.3 Hz, 1H), 4.46 (d, J=2.3 Hz, 1H), 4.06 (dd, J=5.5, 3.7 Hz, 1H), 3.76-3.71 (m, 1H), 3.69-3.57 (m, 2H), 3.44 (s, 3H), 2.17 (s, 3H), 2.15 (s, 3H), 2.09 (s, 3H), 2.04 (s, 3H); $^{13}$C NMR (101 MHz, $CDCl_3$) δ 171.42, 170.46, 170.46, 170.40, 163.10, 150.03, 139.50, 103.61, 97.15, 96.95, 88.50, 81.26, 80.96, 75.33, 72.91, 69.67, 68.89, 65.54, 61.27, 59.05, 50.86, 20.82, 20.75, 20.67, 20.59; HRMS (ESI+) m/z calcd for $C_{25}H_{34}N_3O_{16}$ [M+H] 632.1939, found: 632.1963.

(2S,3S,4S)-3,4-Diacetoxy-2-((1R)-1-((2S,5R)-3-acetoxy-5-(2,4-dioxo-3,4-dihydropyrimidin-1(2H)-yl)-4-methoxytetrahydrofuran-2-yl)-2-amino-2-oxoethoxy)-3,4-dihydro-2H-pyran-6-carboxylic acid (18). To a stirred solution of 16 (0.10 g, 0.16 mmol) and DMSO (0.11 mL, 1.57 mmol) in a 5:1 mixture of $CH_2Cl_2$ and $Et_3N$ (0.80 mL) was added $SO_3$·pyridine (0.25 g, 1.57 mmol). After being stirred for 3 h at r.t., the reaction mixture was added $H_2O$ (0.16 mL) and passed through a silica gel pad ($CHCl_3$/MeOH=92/8) to provide the crude 17. To a stirred solution of the crude mixture in $^t$BuOH (1.0 mL) and 2-methyl-2-butene (0.5 mL) was added a solution of $NaClO_2$ (0.071 g, 0.78 mmol) and $NaH_2PO_4·2H_2O$ (0.12 g, 0.78 mmol) in $H_2O$ (1.0 mL). After being stirred for 4 h at r.t., the reaction was quenched with $H_2O$ and extracted with $CHCl_3$/MeOH (9/1). The combined organic extracts were dried over $Na_2SO_4$ and concentrated in vacuo. The crude product was purified by silica gel column chromatography ($CHCl_3$/MeOH=9/1) to afford 18 (0.078 g, 85%): $^1$H NMR (400 MHz, Methanol-d4) δ 7.77 (d, J=8.1 Hz, 1H), 5.94 (d, J=11.7 Hz, 1H), 5.94 (s, 1H), 5.78 (t, J=2.1 Hz, 1H), 5.66 (dd, J=4.5, 2.5 Hz, 1H), 5.56 (ddd, J=4.7, 3.2, 1.6 Hz, 1H), 5.32 (d, J=3.3 Hz, 1H), 4.99 (t, J=5.2 Hz, 1H), 4.85 (d, J=2.1 Hz, 1H), 4.60 (dd, J=5.2, 2.0 Hz, 1H), 3.95 (t, J=5.0 Hz, 1H), 3.39 (s, 3H), 2.13 (s, 3H), 2.08 (s, 3H), 2.05 (s, 3H); $^{13}$C NMR (101 MHz, MeOD) 0 172.79, 172.06, 171.60, 167.79, 166.01, 152.05, 148.16, 140.97, 104.23, 103.98, 97.91, 88.13, 83.38, 82.91, 76.56, 71.95, 65.17, 65.06, 59.41, 20.75, 20.63, 20.57; HRMS (ESI+) m/z calcd for $C_{23}H_{28}N_3O_{15}$ [M+H] 586.1520, found: 586.1549.

(2S,3S,4S)-2-((1R)-1-((2S,5R)-3-Acetoxy-5-(2,4-dioxo-3,4-dihydropyrimidin-1(2H)-yl)-4-methoxy-tetrahydro-furan-2-yl)-2-amino-2-oxoethoxy)-6-(((S)-2-oxoazepan-3-yl)carbamoyl)-3,4-dihydro-2H-pyran-3,4-diyldiacetate (19). To a stirred solution of 18 (31 mg, 0.053 mmol), 2-(S)-aminocaprolactam (26 mg, 0.16 mmol), HOBt (21 mg, 0.16 mmol) and NMM (58 μL, 0.53 mmol) in DMF (0.26 mL) was added EDCl (51 mg, 0.26 mmol). After being stirred for 6 h at r.t., the reaction was quenched with aq. $NaHCO_3$, and extracted with $CHCl_3$/MeOH (9/1). The combined organic extracts were dried over $Na_2SO_4$ and concentrated in vacuo. The crude product was purified by silica gel column chromatography ($CHCl_3$/MeOH=95/5) to afford 19 (30 mg, 82%): $^1$H NMR (400 MHz, Methanol-d4) 0 7.68 (d, J=8.2 Hz, 1H), 6.02 (t, J=2.1 Hz, 1H), 5.91 (d, J=4.2 Hz, 1H), 5.89 (d, J=6.3 Hz, 1H), 5.73 (dd, J=4.4, 2.5 Hz, 1H), 5.68-5.65 (m, 1H), 5.51 (d, J=3.0 Hz, 1H), 5.01 (d, J=4.6 Hz, 1H), 4.76 (d, J=2.0 Hz, 1H), 4.62 (d, J=12.5 Hz, 1H), 4.60-4.57 (m, 1H), 3.98 (d, J=6.1 Hz, 1H), 3.35 (s, 3H), 2.11 (s, 3H), 2.08 (s, 3H), 2.05 (s, 3H), 2.03-1.98 (m, 2H), 1.91-1.83 (m, 2H), 1.65-1.56 (m, 2H), 1.44-1.37 (m, 2H); $^{13}$C NMR (101 MHz, MeOD) 0 176.12, 172.32, 171.66, 171.29, 171.21, 165.96, 160.96, 151.90, 144.61, 141.42, 106.25, 103.54, 98.81, 88.77, 83.41, 79.28, 77.39, 74.79, 64.91, 64.49, 59.26, 57.36, 53.25, 42.36, 32.19, 29.75, 28.94, 20.54, 20.41, 20.32; HRMS (ESI+) m/z calcd for $C_{29}H_{38}N_5O_{15}$ [M+H] 696.2364, found: 696.2391.

(2S,3S,4S)-2-((1R)-2-Amino-1-(2S,5R)-5-(2,4-dioxo-3,4-dihydropyrimidin-1(2H)-yl)-3-hydroxy-4-methoxytetra-hydrofuran-2-yl)-2-oxoethoxy)-3,4-dihydroxy-N—((S)-2- oxoazepan-3-yl)-3,4-dihydro-2H-pyran-6-carboxamide (3). A solution of 19 (30 mg, 0.043 mmol) in a 5:1 mixture of MeOH and $Et_3N$ (0.60 mL) was stirred for 5 h at r.t., and concentrated in vacuo. The crude mixture was purified by reverse-phase HPLC [column: Luna® (C18, 10 μm, 100 Å, 250×10 mm), solvents: 15:85 MeOH:$H_2O$, flow rate: 3.0 mL/min, UV: 254 nm, retention time: 20 min] to afford I-CAP (3, 24 mg, 98%): $^1H$ NMR (400 MHz, Methanol-d4) δ 7.92 (d, J=8.1 Hz, 1H), 6.02 (d, J=3.8 Hz, 1H), 5.88 (d, J=5.1 Hz, 1H), 5.74 (d, J=8.1 Hz, 1H), 5.23 (d, J=5.6 Hz, 1H), 4.67 (d, J=2.0 Hz, 1H), 4.59-4.54 (m, 2H), 4.38 (t, J=4.2 Hz, 1H), 4.29 (t, J=5.1 Hz, 1H), 3.98 (t, J=5.0 Hz, 1H), 3.84 (t, J=4.6 Hz, 1H), 3.43 (s, 3H), 2.06-1.99 (m, 2H), 1.89-1.81 (m, 2H), 1.62-1.45 (m, 2H), 1.44-1.33 (m, 2H); $^{13}C$ NMR (101 MHz, MeOD) δ 176.27, 173.46, 166.15, 161.85, 152.32, 144.23, 141.91, 109.37, 102.82, 101.22, 90.27, 83.49, 81.02, 78.93, 74.54, 68.51, 63.53, 58.67, 53.35, 42.48, 32.36, 29.91, 29.06; HRMS (ESI+) m/z calcd for $C_{23}H_{32}N_5O_{12}$ [M+H] 570.2048, found: 570.2071.

(2S,3S,4S,5R,6R)-2-((S)-((3aR,4R,6R,6aR)-6-(3-((Benzyloxy)methyl)-2,4-dioxo-3,4-dihydro-pyrimidin-1(2H)-yl)-2,2-dimethyltetrahydrofuro[3,4-d][1,3]dioxol-4-yl)(cyano)methoxy)-6-((2-chloroacetoxy)-methyl)tetrahydro-2H-pyran-3,4,5-triyltriacetate (21). To a stirred suspension of 20 (0.24 g, 0.56 mmol), 14 (0.55 g, 1.12 mmol), MS 3 Å (0.72 g), and $SrCO_3$ (0.41 g, 2.80 mmol) in $CH_2Cl_2$ (14.0 mL) were added $AgBF_4$ (0.055 g, 0.28 mmol) and NIS (0.25 g, 1.12 mmol) at 0° C. After being stirred for 12 h, the reaction mixture was added $Et_3N$ (1.0 mL), and passed through a silica gel pad (hexanes/EtOAc=1/4). The filtrate was concentrated in vacuo. The crude mixture was purified by silica gel column chromatography (hexanes/EtOAc=6/4-4/6) to afford 21 (0.39 g, 88%): $^1H$ NMR (400 MHz, Chloroform-d) δ 7.37-7.28 (m, 5H), 10 7.20 (d, J=8.1 Hz, 1H), 5.82 (d, J=8.1 Hz, 1H), 5.61 (d, J=1.6 Hz, 1H), 5.50 (d, J=9.8 Hz, 1H), 5.42 (d, J=9.8 Hz, 1H), 5.35-5.27 (m, 1H), 5.23 (dd, J=10.0, 3.3 Hz, 1H), 5.07 (d, J=1.9 Hz, 1H), 5.00 (d, J=3.5 Hz, 1H), 4.98 (dd, J=6.4, 1.6 Hz, 1H), 4.84 (d, J=7.1 Hz, 1H), 4.69 (s, 2H), 4.43 (dd, J=7.1, 3.6 Hz, 1H), 4.20 (dd, J=12.2, 4.3 Hz, 1H), 4.17-4.07 (m, 2H), 4.05 (d, J=1.6 Hz, 2H), 3.97-3.92 (m, 1H), 2.16 (s, 3H), 2.02 (s, 3H), 1.98 (s, 3H), 1.59 (s, 3H), 1.39 (s, 3H); $^{13}C$ NMR (101 MHz, $CDCl_3$) δ 169.80, 169.57, 169.47, 166.80, 162.08, 150.84, 140.89, 137.67, 128.33 (2C), 127.91, 127.77, 127.63 (2C), 115.23, 114.72, 102.84, 96.56, 96.30, 86.55, 84.15, 80.95, 72.42, 70.41, 69.41, 68.39 (2C), 66.04, 65.35, 62.90, 40.52, 27.03, 25.20, 20.73, 20.64, 20.59; HRMS (ESI+) m/z calcd for $C_{35}H_{41}ClN_3O_{16}$ [M+H] 794.2175, found: 794.2198.

(2R,3S,4S,5R,6R)-2-((R)-2-Amino-1-((3aR,4S,6R,6aR)-6-(2,4-dioxo-3,4-dihydropyrimidin-1-(2H)-yl)-2,2-dimethyltetrahydrofuro[3,4-d][1,3]dioxol-4-yl)-2-oxoethoxy)-6-(hydroxymethyl)-tetrahydro-2H-pyran-3,4,5-triyltriacetate (22). To a stirred solution of 21 (0.39 g, 0.49 mmol) in a 9:1 mixture of EtOH and $H_2O$ (4.9 mL) were added $HgCl_2$ (0.27 g, 25 0.98 mmol) and acetaldoxime (0.30 mL, 4.9 mmol) at rt. After being stirred for 12 h at r.t., the reaction mixture was concentrated in vacuo. The residue was diluted with aq. $NaHCO_3$, and extracted with $CHCl_3$. The combined organic extracts were dried over $Na_2SO_4$ and concentrated in vacuo. The crude product was purified by silica gel column chromatography (hexanes/EtOAc=1/2 to $CHCl_3$/MeOH=97/3) to afford the amide (0.36 g, 91%). To a solution of the amide (0.36 g, 0.45 mmol) in a 1:1 mixture of THF and MeOH (4.5 mL) was added thiourea (0.10 g, 1.34 mmol). After being stirred for 11 h at 50° C., the reaction mixture was concentrated in vacuo. The residue was diluted with $H_2O$, and extracted with $CHCl_3$. The combined organic extracts were dried over $Na_2SO_4$ and concentrated in vacuo. The crude product was purified by silica gel column chromatography ($CHCl_3$/MeOH=98/2 to 97/3 to 96/4) to afford the primary alcohol (0.25 g, 76%). To a stirred solution of the alcohol (0.25 g, 0.34 mmol) and AcOH (0.08 mL) in a 1:1 mixture of THF and $^i$PrOH (4.0 mL) was added 10% Pd/C (0.20 g) under $N_2$. $H_2$ gas was introduced and the reaction mixture was stirred under $H_2$ atmosphere at rt. After being stirred for 4 h, the reaction mixture was filtered through Celite and concentrated in vacuo. The crude product was purified by silica gel column chromatography (CHCB/MeOH=96/4 to 92/8) to afford 22 (0.17 g, 80%): $^1H$ NMR (400 MHz, Chloroform-d) δ 9.45 (brs, 1H), 7.34 (d, J=8.0 Hz, 1H), 6.72 (brs, 1H), 6.17 (brs, 1H), 5.78 (d, J=8.0 Hz, 1H), 5.60 (d, J=1.7 Hz, 1H), 5.43 (dd, J=10.1, 3.5 Hz, 1H), 5.33 (dd, J=3.5, 1.7 Hz, 1H), 5.20 (t, J=10.1 Hz, 1H), 5.12-5.05 (m, 1H), 5.03 (dd, J=6.4, 1.7 Hz, 1H), 4.98 (s, 1H), 4.46 (d, J=5.8 Hz, 1H), 4.33 (t, J=5.1 Hz, 1H), 3.88 (dt, J=10.1, 4.0 Hz, 1H), 3.60-3.53 (m, 2H), 2.14 (s, 3H), 2.07 (s, 3H), 2.02 (s, 3H), 1.55 (s, 3H), 1.35 (s, 3H); $^{13}C$ NMR (101 MHz, $CDCl_3$) δ 170.68, 170.40, 170.28, 170.24, 163.27, 150.13, 142.81, 114.72, 102.85, 96.39, 87.34, 84.26, 80.35, 71.92, 69.35, 68.64, 66.03, 61.16, 27.25, 25.42, 20.83, 20.77, 20.74; HRMS (ESI+) m/z calcd for $C_{25}H_{34}N_3O_{15}$ [M+H] 616.1990, found: 616.2018.

(2S,3S,4S)-2-(R)-2-Amino-1-(3aR,4S,6R,6aR)-6-(2,4-dioxo-3,4-dihydropyrimidin-1 (2H)-yl)-2,2-dimethyltetrahydrofuro[3,4-d][1,3]dioxol-4-yl)-2-oxoethoxy)-6-(((S)-2-oxoazepan-3-yl)-carbamoyl)-3,4-dihydro-2H-pyran-3,4-diyl diacetate (23). To a stirred solution of 22 (0.17 g, 0.27 mmol) and DMSO (0.19 mL, 2.72 mmol) in a 5:1 mixture of $CH_2Cl_2$ and $Et_3N$ (1.4 mL) was added $SO_3$·pyridine (0.43 g, 2.72 mmol). After being stirred for 3 h at r.t., the reaction mixture was added $H_2O$ (0.27 mL) and passed through a silica gel pad ($CHCl_3$/MeOH=92/8). To a stirred solution of the crude mixture in $^t$BuOH (1.0 mL) and 2-methyl-2-butene (0.5 mL) was added a solution of $NaClO_2$ (0.12 g, 1.36 mmol) and $NaH_2PO_4 \cdot 2H_2O$ (0.21 g, 1.36 mmol) in $H_2O$ (1.0 mL). After being stirred for 5 h at r.t., the reaction was extracted with $CHCl_3$/MeOH (9/1). The combined organic extracts were dried over $Na_2SO_4$ and concentrated in vacuo. The crude product was purified by silica gel column chromatography ($CHCl_3$/MeOH=9/1) to afford the acid (0.13 g, 81%). To a stirred solution of the acid (28 mg, 0.049 mmol), 2-(S)-aminocaprolactam (24 mg, 0.15 mmol), HOBt (20 mg, 0.15 mmol) and NMM (54 μL, 0.49 mmol) in DMF (0.25 mL) was added EDCl (47 mg, 0.25 mmol). After being stirred for 14 h at r.t., the reaction was quenched with aq. $NaHCO_3$, and extracted with $CHCl_3$/MeOH (9/1). The combined organic extracts were dried over $Na_2SO_4$ and concentrated in vacuo. The crude product was purified by silica gel column chromatography ($CHCl_3$/MeOH=95/5) to afford 23 (30 mg, 89%): $^1H$ NMR (400 MHz, Methanol-d4) δ 7.79 (d, J=8.0 Hz, 1H), 5.98 (t, J=2.0 Hz, 1H), 5.84 (d, J=2.8 Hz, 1H), 5.78 (d, J=8.0 Hz, 1H), 5.62 (dd, J=4.5, 2.6 Hz, 1H), 5.51-5.48 (m, 1H), 5.45 (d, J=3.1 Hz, 1H), 4.74 (d, J=2.8 Hz, 1H), 4.71 (dd, J=6.2, 2.9 Hz, 1H), 4.65 (dd, J=6.2, 3.3 Hz, 1H), 4.59-4.55 (m, 2H), 3.76-3.67 (m, 4H), 2.09 (s, 3H), 2.04 (s, 3H), 1.86 (d, J=13.4 Hz, 3H), 1.63-1.52 (m, 3H), 1.51 (s, 3H), 1.45-1.34 (m, 3H), 1.25 (s, 3H); $^{13}C$ NMR (101 MHz, MeOD) δ 176.35, 172.24, 171.62, 171.28, 166.24, 161.14, 151.99, 144.75, 142.76, 115.34, 106.38, 102.91, 98.75, 93.55, 87.12, 85.94, 82.02, 78.13, 67.16, 64.99, 64.46, 56.04, 53.46, 46.10, 42.52, 42.43, 32.25, 29.89, 29.08, 27.47, 25.47, 20.61, 20.52; HRMS (ESI+) m/z calcd for $C_{29}H_{38}N_5O_{14}$ [M+H] 680.2415, found: 680.2432.

(2S,3S,4S)-2-((1R)-2-Amino-1-((2S,5R)-5-(2,4-dioxo-3,4-dihydropyrimidin-1(2H)-yl)-3,4-dihydroxy-tetrahydrofuran-2-yl)-2-oxoethoxy)-3,4-dihydroxy-N—((S)-2-oxoazepan-3-yl)-3,4-dihydro-2H-pyran-6-carboxamide (4). A solution of 23 (30 mg, 0.044 mmol) in a 4:1 mixture of TFA and $H_2O$ (0.88 mL) was stirred for 4 h at r.t., and concentrated in vacuo. A solution of the crude diol in a 5:1 mixture of MeOH and $Et_3N$ (0.88 mL) was stirred for 9 h at r.t., filtered, and concentrated in vacuo. The crude mixture was purified by reverse-phase HPLC [column: Luna® (C18, 10 μm, 100 Å, 250×10 mm), solvents: 15:85 MeOH:$H_2O$, flow rate: 3.0 mL/min, UV: 254 nm, retention time: 16 min] to afford DM-CAP (4, 22 mg, 90%): $^1H$ NMR (400 MHz, Methanol-d4) δ 7.94 (d, J=8.1 Hz, 1H), 6.03 (d, J=4.5 Hz, 1H), 5.85 (d, J=3.7 Hz, 1H), 5.73 (d, J=8.2 Hz, 1H), 5.19 (d, J=6.7 Hz, 1H), 4.68 (d, J=1.7 Hz, 1H), 4.61 (dd, J=11.2, 1.4 Hz, 1H), 4.54 (dd, J=5.8, 1.7 Hz, 1H), 4.36 (t, J=4.5 Hz, 1H), 4.30 (t, J=5.5 Hz, 1H), 4.12 (t, J=4.4 Hz, 1H), 3.97 (t, J=5.7 Hz, 1H), 3.90 (t, J=6.5 Hz, 1H), 3.43-3.38 (m, 1H), 3.03 (t, J=7.0 Hz, 1H), 2.70-2.64 (m, 1H), 2.07-1.97 (m, 2H), 1.81 (d, J=15.2 Hz, 2H), 1.62 (q, J=11.9, 10.7 Hz, 1H), 1.39 (s, 1H); $^{13}C$ NMR (101 MHz, MeOD) δ 176.85, 174.05, 166.21, 162.02, 152.21, 144.60, 141.91, 108.72, 102.50, 101.60, 90.76, 84.77, 79.50, 75.68, 71.40, 63.63, 60.06, 53.44, 42.50, 31.89, 29.82, 29.14; HRMS (ESI+) m/z calcd for $C_{22}H_{30}N_5O_{12}$ [M+H] 556.1891, found: 556.1912.

Scheme 2

A: Synthesis of capuramycin phenoxypiperidinbenzylamide analogues, CPPB; *iso*-CPPB (I-CBPP), and demethyl-CPPB (DM-CAP)

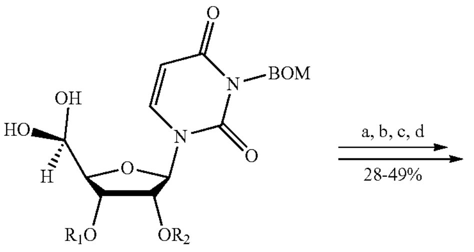

13: $R_1$ = Ac, $R_2$ = $CH_3$
20: $R_1$, $R_2$ = acelonide
24: $R_1$ = $CH_3$ $R_2$ = Ac
25: $R_1$ = $CH_3$, $R_2$ = $CH_3$

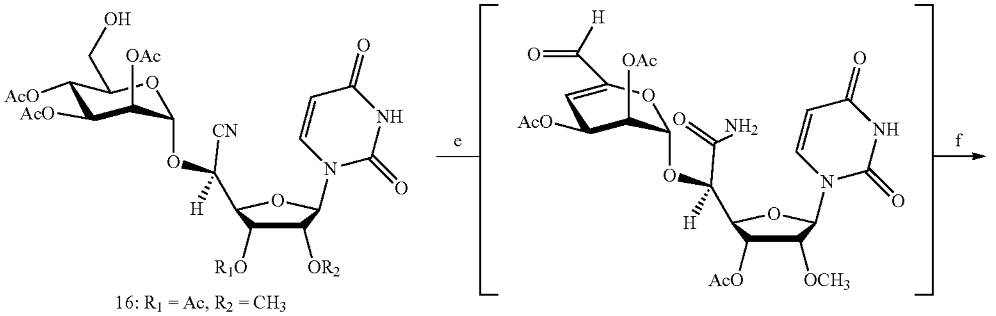

16: $R_1$ = Ac, $R_2$ = $CH_3$
22: $R_1$, $R_2$ = acelonide
26: $R_1$ = $CH_3$, $R_2$ = Ac
27: $R_1$ = $CH_3$, $R_2$ = $CH_3$

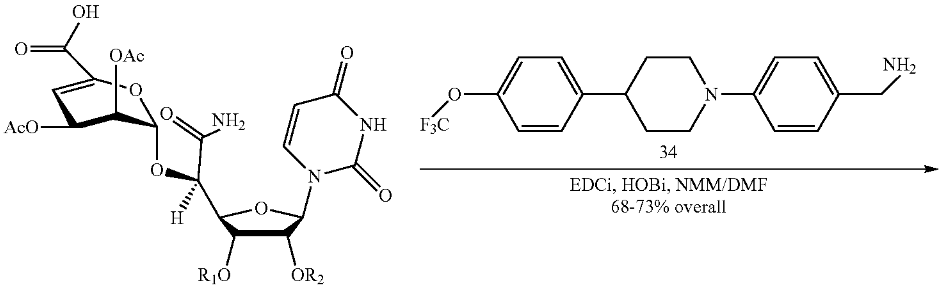

-continued
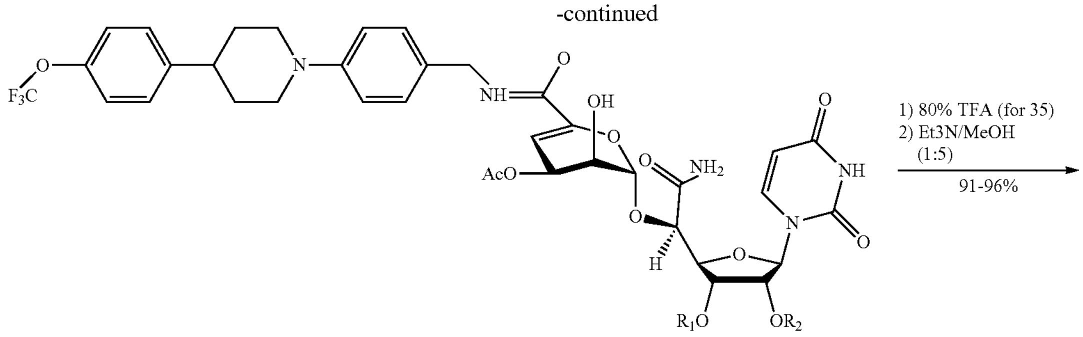
35: $R_1$ = Ac, $R_2$ = $CH_3$
36: $R_1$, $R_2$ = acelonide
37: $R_1$ = $CH_3$, $R_2$ = Ac
38: $R_1$ = $CH_3$, $R_2$ = CH3
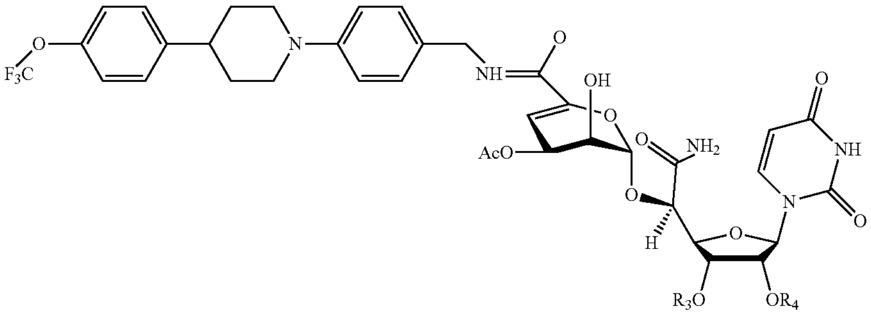
CPPB (5): $R_3$ = $CH_3$, $R_4$ = $CH_3$
I-CPPB (6): $R_3$ = H, $R_4$ = $CH_3$
OM-CPPB (7): $R_3$ = $CH_3$, $R_4$ = $CH_3$
DM-CPPB (8): $R_3$ = H, $R_2$ = $CH_3$
B: Synthesis of capuramycin phenoxypiperidinbenzylanamine analogues, CPPB, *iso*-CPPB (I-CBPP),
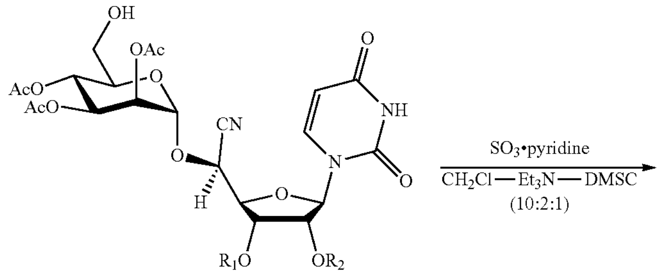
18: $R_1$ = Ac, $R_2$ = $CH_3$
28: $R_1$ = $CH_3$, $R_2$ = Ac
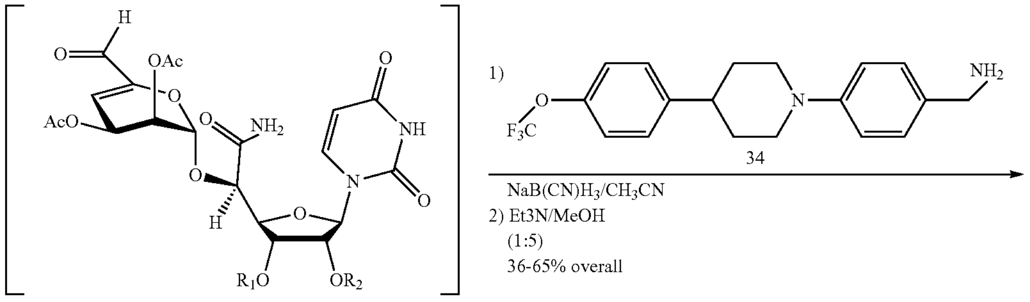
17: $R_1$ = Ac, $R_2$ = $CH_3$
28: $R_1$ = $CH_3$, $R_2$ = Ac -continued

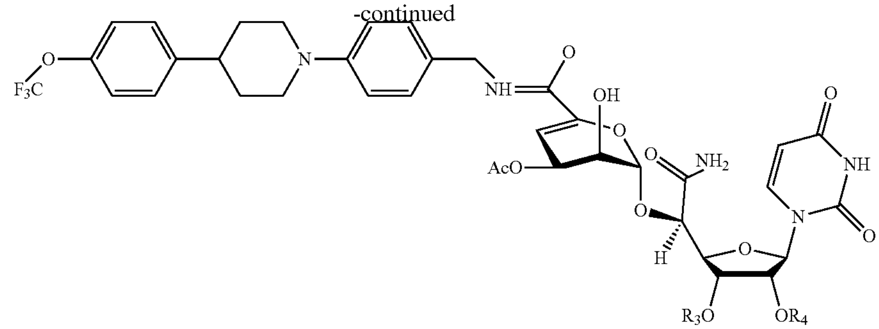

a) 14, NiS, $AgBF_4$, $SrCO_3$, 3A MS, $CH_2Cl_2$, 0° C., 12 h.; b) $HgCl_2$, aldoxime,EtOH—$H_2O$,;
c) thiourea, MeO-THF, 50° C,; d) $H_2$, 10% Pd-C, AcOH-$^i$PrOH-THF,;
e) $SO_3$ pyridine, $CH_2Cl_2$—$Et_3N$—DMSO (10:2:1),; f) $NAClO_2$, $NaH_2PO_4$, 2-methyl-2-butene,$^t$BuOH—$H_2O$ The carboxylic acid intermediate 32 for CAP (1) was subjected to peptide coupling reaction with (((trifluoromethoxy)phenoxy) piperidin-1-yl)phenyl)methylamine (34), providing the protected CPPB, 37. Saponification of 37 and purification by reverse HPLC yielded CPPB (5) in 95% overall yield from 37. Similarly, I—CPPB (6), OM-CPPB (7), and DM-CPPB (8) were synthesized from the cyanohydrins 18, 33, and 31 in 24-34% overall yield. Capuramycin phenoxypiperidinbenzylamine analogues, CPPA (9) and I-CPPA (10), were synthesized via reductive aminations of the aldehydes 29 and 18 with the amine 34, furnishing the desired products in 63-65% overall yield from 26 and 16 after saponification.

(2S,3S,4S)-2-((1R)-1-(2S,5R)-4-Acetoxy-5-(2,4-dioxo-3,4-dihydropyrimidin-1(2H)-yl)-3-methoxy-tetrahydrofuran-2-yl)-2-amino-2-oxoethoxy)-6-(4-(4-(4-(trifluoromethoxy)-phenyl)-piperidin-1-yl)benzyl)carbamoyl)-3,4-dihydro-2H-pyran-3,4-diyldiacetate (37). To a stirred solution of 32 (55 mg, 0.094 mmol), 34 (0.10 g, 0.28 mmol), HOBt (38 mg, 0.28 mmol) and NMM (95 μL, 0.94 mmol) in DMF (0.47 mL) was added EDCl (90 mg, 0.47 mmol). After being stirred for 7 h at r.t., the reaction mixture was quenched with aq. $NaHCO_3$, and extracted with $CHCl_3$/MeOH (9/1). The combined organic extracts were dried over $Na_2SO_4$ and concentrated in vacuo. The crude product was purified by silica gel column chromatography ($CHCl_3$/MeOH=95/5) to afford 37 (76 mg, 87%): $^1$H NMR (400 MHz, Methanol-d4) δ 7.71 (d, J=8.1 Hz, 1H), 7.23 (d, J=8.5 Hz, 2H), 7.19 (d, J=8.8 Hz, 2H), 7.03 (d, J=9.1 Hz, 2H), 6.97 (d, J=8.7 Hz, 2H), 5.97 (t, J=2.1 Hz, 1H), 5.91 (d, J=8.1 Hz, 1H), 5.87 (d, J=3.8 Hz, 1H), 5.74 15 (dd, J=4.5, 2.4 Hz, 1H), 5.67 (ddd, J=4.5, 2.8, 1.7 Hz, 1H), 5.43 (d, J=2.8 Hz, 1H), 5.28 (dd, J=5.1, 3.8 Hz, 1H), 4.70 (d, J=1.9 Hz, 1H), 4.54 (dq, J=7.5, 3.8 Hz, 1H), 4.42 (d, J=14.5 Hz, 1H), 4.38 (dd, J=6.2, 1.9 Hz, 1H), 4.33 (d, J=14.4 Hz, 1H), 3.82-3.79 (m, 1H), 3.48 (td, J=9.0, 6.8, 3.5 Hz, 3H), 3.13-3.06 (m, 2H), 3.05 (s, 3H), 2.09 (s, 3H), 2.09 (s, 3H), 2.06 (s, 3H), 1.87 (dtd, J=12.3, 8.2, 3.6 Hz, 3H); $^{13}$C NMR (101 MHz, MeOD) δ 172.85, 171.84, 171.43, 171.17, 166.07, 162.39, 157.61, 152.11, 151.92, 144.94, 143.92, 141.57, 130.89, 130.02 (2C), 123.59 (2C), 118.04 (2C), 117.98 (2C), 106.19, 103.75, 98.26, 89.36, 83.17, 78.98, 76.60, 74.71, 73.98, 64.75, 59.35, 48.18, 48.16, 31.43 (2C), 20.70, 20.52, 20.49; HRMS (ESI+) m/z calcd for $C_{42}H_{47}F_3N_5O_{15}$ [M+H] 918.3021, found 918.3049.

(2S,3S,4S)-2-((1R)-2-Amino-1-((2S,5R)-5-(2,4-dioxo-3,4-dihydropyrimidin-1(2H)-yl)-4-hydroxy-3-methoxytetrahydrofuran-2-yl)-2-oxoethoxy)-3,4-dihydroxy-N-(4-(4-(4-(trifluoromethoxy)-phenyl)piperidin-1-yl)benzyl)-3,4-dihydro-2H-pyran-6-carboxamide (5). A solution of 37 (76 mg, 0.082 mmol) in a 5:1 mixture of MeOH and $Et_3N$ (1.6 mL) was stirred for 6 h at r.t., and concentrated in vacuo. The crude mixture was purified by reverse-phase HPLC [column: Luna® (C18, 10 μm, 100 Å, 250×10 mm), solvents: 65:35 MeOH:$H_2O$, flow rate: 3.0 mL/min, UV: 254 nm, retention time: 18 min] to afford CPPB (5, 63 mg, 95%): $^1$H NMR (400 MHz, Methanol-d4) δ 7.86 (d, J=8.1 Hz, 1H), 7.20 (dd, J=10.9, 8.6 Hz, 4H), 7.02 (d, J=9.1 Hz, 2H), 6.97 (d, J=8.7 Hz, 2H), 5.98 (dd, J=3.3, 1.0 Hz, 1H), 5.80 (d, J=4.4 Hz, 1H), 5.76 (d, J=8.2 Hz, 1H), 5.21 (d, J=4.6 Hz, 1H), 4.68 (d, J=2.0 Hz, 1H), 4.54 (dp, J=7.3, 3.6 Hz, 1H), 4.48 (dd, J=5.2, 2.0 Hz, 1H), 4.44 (d, J=14.5 Hz, 1H), 4.39 (t, J=3.9 Hz, 1H), 4.33 (d, J=14.6 Hz, 1H), 4.20 (t, J=4.7 Hz, 1H), 4.06-4.02 (m, 1H), 3.66 (t, J=5.1 Hz, 1H), 3.52-3.45 (m, 3H), 3.19 (s, 3H), 3.08 (ddd, J=12.3, 8.6, 3.4 Hz, 3H), 2.15-2.07 (m, 2H), 1.86 (dtd, J=12.2, 8.3, 3.5 Hz, 3H); $^{13}$C NMR (101 MHz, MeO) δ 173.68, 166.16, 163.31, 157.62, 152.18, 152.08, 144.15, 141.83, 130.91, 129.76 (2C), 123.58 (2C), 118.03 (4C), 109.58, 102.74, 100.64, 90.83, 83.32, 80.35, 77.51, 74.27, 74.01, 67.61, 63.48, 58.61, 48.20 (2C), 43.51, 31.47 (2C); HRMS (ESI+) m/z calcd for $C_{36}H_{41}F_3N_5O_{12}$ [M+H] 792.2704, found 792.2733.

(2S,3S,4S)-2-((1R)-1-(2S,5R)-3-Acetoxy-5-(2,4-dioxo-3,4-dihydropyrimidin-1(2H)-yl)-4-methoxytetrahydrofuran-2-yl)-2-amino-2-oxoethoxy)-6-(4-(4-(4-(trifluoromethoxy) phenyl)-piperidin-1-yl)benzyl)carbamoyl)-3,4-dihydro-2H-pyran-3,4-diyl diacetate (35). To a stirred solution of 18 (33 mg, 0.056 mmol), 34 (62 mg, 0.17 mmol), HOBt (23 mg, 0.17 mmol) and NMM (62 μL, 0.56 mmol) in DMF (0.28 mL) was added EDCl (54 mg, 0.28 mmol). After being stirred for 14 h at r.t., the reaction was quenched with aq. $NaHCO_3$, and extracted with $CHCl_3$/MeOH (9/1). The combined organic extracts were dried over $Na_2SO_4$ and concentrated in vacuo. The crude product was purified by silica gel column chromatography ($CHCl_3$/MeOH=95/5) to afford 35 (43 mg, 82%): $^1$H NMR (400 MHz, Methanol-d4) δ 7.69 (d, J=8.2 Hz, 1H), 7.22 (d, J=8.5 Hz, 2H), 7.19 (d, J=8.6 Hz, 2H), 7.02 (d, J=9.0 Hz, 2H), 6.98 (d, J=8.4 Hz, 2H), 5.99-5.97 (m, 1H), 5.95 (d, J=5.8 Hz, 1H), 5.91 (d, J=8.1 Hz, 1H), 5.74-5.71 (m, 1H), 5.66-5.63 (m, 1H), 5.46 (d, J=3.2 Hz, 1H), 5.05 (t, J=4.7 Hz, 1H), 4.78 (d, J=2.0 Hz, 1H), 4.57-4.52 (m, 1H), 4.49 (d, J=14.5 Hz, 1H), 4.39-4.34 (m, 1H), 4.30 (d, J=14.7 Hz, 1H), 3.84-3.80 (m, 1H), 3.64 (s, 3H), 3.53-3.45 (m, 2H), 3.13-3.06 (m, 2H), 2.83 (t, J=6.5 Hz, 1H), 2.10 (s, 3H), 2.07 (s, 3H), 2.06 (s, 3H), 1.87 (dtd, J=12.7, 8.5, 3.5 Hz, 3H); $^{13}C$ NMR (101 MHz, MeOD) δ 172.92, 171.74, 171.36, 170.39, 166.18, 162.23, 157.56, 152.06, 151.81, 145.05, 140.90, 130.78, 129.96 (2C), 123.52 (2C), 117.96 (2C), 117.92 (2C), 105.75, 103.47, 98.22, 88.92, 82.72, 78.21, 76.44, 73.95, 67.92, 64.42, 61.21, 58.65, 58.20, 48.10 (2C), 43.57, 31.38 (2C), 20.60, 20.44, 20.39; HRMS (ESI+) m/z calcd for $C_{42}H_{47}F_3N_5O_{15}$ [M+H] 918.3021, found 918.3038.

(2S,3S,4S)-2-((1R)-2-Amino-1-((2S,5R)-5-(2,4-dioxo-3,4-dihydropyrimidin-1(2H)-yl)-3-hydroxy-4-methoxytetrahydrofuran-2-yl)-2-oxoethoxy)-3,4-dihydroxy-N-(4-(4-(4-(trifluoro-methoxy)phenyl)-piperidin-1-yl)benzyl)-3,4-dihydro-2H-pyran-6-carboxamide (6). A solution of 35 (43 mg, 0.046 mmol) in a 5:1 mixture of MeOH and $Et_3N$ (0.92 mL) was stirred for 6 h at r.t., and concentrated in vacuo. The crude mixture was purified by reverse-phase HPLC [column: Luna® (C18, 10 μm, 100 Å, 250×10 mm), solvents: 65:35 MeOH:$H_2O$, flow rate: 3.0 mL/min, UV: 254 nm, retention time: 19 min] to afford I—CPPB (6, 35 mg, 93%): $^1H$ NMR (400 MHz, Methanol-d4) δ 7.79 (d, J=8.2 Hz, 1H), 7.19 (d, J=8.6 Hz, 4H), 7.02 (d, J=9.1 Hz, 2H), 6.98 (d, J=8.5 Hz, 2H), 5.98 (d, J=3.6 Hz, 1H), 5.94 (d, J=5.1 Hz, 1H), 5.77 (d, J=8.0 Hz, 1H), 5.36 (d, J=5.8 Hz, 1H), 4.67-4.65 (m, 1H), 4.61 (d, J=2.8 Hz, 1H), 4.48 (dd, J=8.6, 4.6 Hz, 1H), 4.36-4.33 (m, 1H), 4.27 (dd, J=5.4, 2.7 Hz, 1H), 3.71-3.65 (m, 2H), 3.51 (d, J=4.4 Hz, 2H), 3.48 (s, 3H), 3.25-3.18 (m, 2H), 2.13-2.00 (m, 3H), 1.92-1.76 (m, 3H); $^{13}C$ NMR (101 MHz, MeOD) δ 173.68, 166.15, 163.30, 157.62, 152.18, 152.08, 144.15, 141.83, 130.90, 129.76 (2C), 123.58 (2C), 118.10 (2C), 118.02 (2C), 109.57, 102.73, 100.63, 90.83, 83.32, 80.35, 77.51, 74.27, 74.01, 67.61, 63.48, 58.61, 48.20 (2C), 43.51, 31.47 (2C); HRMS (ESI+) m/z calcd for $C_{36}H_{41}F_3N_5O_{12}$ [M H] 792.2704, found 792.2728.

(2S,3S,4S)-2-((1R)-2-Amino-1-((2S,5R)-5-(2,4-dioxo-3,4-dihydropyrimidin-1(2H)-yl)-3,4-dimethoxytetrahydrofuran-2-yl)-2-oxoethoxy)-6-(4-(4-(4-(trifluoromethoxy)phenyl)piperidin-1-yl)benzyl)-carbamoyl)-3,4-dihydro-2H-pyran-3,4-diyl diacetate (38). To a stirred solution of 33 (38 mg, 0.068 mmol), 34 (75 mg, 0.20 mmol), HOBt (28 mg, 0.20 mmol) and NMM (75 μL, 0.68 mmol) in DMF (0.34 mL) was added EDCl (65 mg, 0.34 mmol). After being stirred for 7 h at r.t., the reaction was quenched with aq. $NaHCO_3$, and extracted with $CHCl_3$/MeOH (9/1). The combined organic extracts were dried over $Na_2SO_4$ and concentrated in vacuo. The crude product was purified by silica gel column chromatography ($CHCl_3$/MeOH=95/5) to afford 38 (53 mg, 86%): $^1H$ NMR (400 MHz, Methanol-d4) δ 7.75 (d, J=8.2 Hz, 1H), 7.24 (d, J=8.6 Hz, 2H), 7.19 (d, J=8.8 Hz, 2H), 7.02 (d, J=9.1 Hz, 2H), 6.98 (d, J=8.5 Hz, 2H), 5.98 (d, J=2.0 Hz, 1H), 5.96 (d, J=8.1 Hz, 1H), 5.85 (d, J=2.9 Hz, 1H), 5.71-5.66 (m, 2H), 5.43 (d, J=2.3 Hz, 1H), 4.70 (d, J=1.9 Hz, 1H), 4.57-4.51 (m, 1H), 4.45-4.40 (m, 2H), 4.34 (d, J=14.4 Hz, 1H), 3.86 (dd, J=4.9, 2.9 Hz, 1H), 3.79 (t, J=6.5 Hz, 1H), 3.60 (dd, J=6.9, 4.9 Hz, 1H), 3.50 (td, J=7.6, 7.0, 3.3 Hz, 2H), 3.46 (s, 3H), 3.11 (dd, J=8.9, 3.6 Hz, 1H), 3.08 (s, 3H), 2.83 (t, J=6.5 Hz, 1H), 2.14 (dd, J=8.7, 5.4 Hz, 1H), 2.10 (s, 3H), 2.07 (s, 3H), 1.87 (dtd, J=12.5, 8.2, 3.5 Hz, 2H); $^{13}C$ NMR (101 MHz, MeOD) δ 172.98, 171.81, 171.42, 166.22, 162.30, 157.62, 152.12, 151.87, 145.11, 140.96, 130.85, 130.02 (2C), 123.58 (2C), 118.03 (2C), 117.98 (2C), 105.81, 103.54, 98.28, 88.98, 82.79, 82.54, 78.28, 76.50, 74.02, 64.59, 64.49, 61.28, 58.72, 58.27, 48.17 (2C), 43.64, 42.08, 31.45 (2C), 20.67, 20.51; HRMS (ESI+) m/z calcd for $C_{41}H_{47}F_3N_5O_{15}$ [M+H] 906.3021, found 906.3045.

(2S,3S,4S)-2-((1R)-2-Amino-1-(2S,5R)-5-(2,4-dioxo-3,4-dihydropyrimidin-1(2H)-yl)-3,4-dimethoxy-tetrahydrofuran-2-yl)-2-oxoethoxy)-3,4-dihydroxy-N-(4-(4-(4-(trifluoromethoxy)-phenyl)piperidin-1-yl)benzyl)-3,4-dihydro-2H-pyran-6-carboxamide (7). A solution of 38 (53 mg, 0.059 mmol) in a 5:1 mixture of MeOH and $Et_3N$ (1.2 mL) was stirred for 6 h at r.t., and concentrated in vacuo. The crude mixture was purified by reverse-phase HPLC [column: Luna® (C18, 10 μm, 100 Å, 250×10 mm), solvents: 65:35 MeOH:$H_2O$, flow rate: 3.0 mL/min, UV: 254 nm, retention time: 21 min] to afford OM-CPPB (7, 46 mg, 96%): $^1H$ NMR (400 MHz, Methanol-d4) δ 7.89 (d, J=8.1 Hz, 1H), 7.22 (d, J=8.4 Hz, 2H), 7.19 (d, J=8.7 Hz, 2H), 7.02 (d, J=9.1 Hz, 2H), 6.96 (d, J=8.5 Hz, 2H), 5.98 (dd, J=3.0, 1.2 Hz, 1H), 5.85 (d, J=3.3 Hz, 1H), 5.76 (d, J=8.1 Hz, 1H), 5.22 (d, J=4.1 Hz, 1H), 4.67 (d, J=1.9 Hz, 1H), 4.57-4.51 (m, 1H), 4.46 (dd, J=6.8, 2.0 Hz, 1H), 4.43 (d, J=14.9 Hz, 1H), 4.40 (d, J=3.7 Hz, 1H), 4.32 (d, J=14.5 Hz, 1H), 4.08 (t, J=4.2 Hz, 1H), 3.90 (t, J=4.1 Hz, 1H), 3.70 (t, J=5.5 Hz, 1H), 3.52-3.47 (m, 2H), 3.45 (s, 3H), 3.13 (s, 3H), 3.08 (td, J=9.1, 4.6 Hz, 2H), 2.15-2.09 (m, 2H), 1.91-1.82 (m, 2H); $^{13}C$ NMR (101 MHz, MeOD) δ 173.61, 166.17, 163.21, 157.62, 152.09, 151.92, 144.02, 141.57, 130.94, 129.89 (2C), 123.59 (2C), 118.03 (2C), 117.98 (2C), 109.78, 102.61, 100.76, 88.94, 83.23, 82.71, 78.58, 77.02, 74.02, 67.27, 63.42, 60.07, 58.70, 58.37, 48.18, 47.87, 45.76, 43.53, 31.46 (2C); HRMS (ESI+) m/z calcd for $C_{37}H_{14}F_3N_5O_{13}$ [M+H] 822.2809, found 822.2838.

(2S,3S,4S)-2-((R)-2-Amino-1-((3aR,4S,6R,6aR)-6-(2,4-dioxo-3,4-dihydropyrimidin-1(2H)-yl)-2,2-dimethyltetrahydrofuro[3,4-d][1,3]dioxol-4-yl)-2-oxoethoxy)-6-((4-(4-(4-(trifluoro-methoxy)phenyl)piperidin-1-yl)benzyl)carbamoyl)-3,4-dihydro-2H-pyran-3,4-diyldiacetate (36). To a stirred solution of 31 (27 mg, 0.047 mmol), 34 (52 mg, 0.14 mmol), HOBt (19 mg, 0.14 mmol) and NMM (52 μL, 0.47 mmol) in DMF (0.24 mL) was added EDCl (45 mg, 0.24 mmol). After being stirred for 11 h at r.t., the reaction was quenched with aq. $NaHCO_3$, and extracted with $CHCl_3$/MeOH (9/1). The combined organic extracts were dried over $Na_2SO_4$ and concentrated in vacuo. The crude product was purified by silica gel column chromatography ($CHCl_3$/MeOH=95/5) to afford 36 (37 mg, 84%): $^1H$ NMR (400 MHz, Methanol-d4) δ 7.69 (d, J=8.1 Hz, 1H), 7.20 (t, J=9.5 Hz, 4H), 7.02 (d, J=9.2 Hz, 2H), 6.98 (d, J=8.5 Hz, 2H), 5.99 (t, J=2.0 Hz, 1H), 5.87 (d, J=3.0 Hz, 1H), 5.83 (d, J=8.1 Hz, 1H), 5.66 (dd, J=4.4, 2.5 Hz, 1H), 5.57-5.54 (m, 1H), 5.41 (d, J=3.0 Hz, 1H), 4.78 (d, J=2.3 Hz, 1H), 4.70 (dd, J=6.3, 3.1 Hz, 1H), 4.63 (dd, J=6.4, 3.5 Hz, 1H), 4.57-4.52 (m, 1H), 4.39 (s, 2H), 3.79 (t, J=6.5 Hz, 1H), 3.64 (s, 1H), 3.49 (ddd, J=10.9, 6.4, 3.6 Hz, 2H), 3.09 (ddd, J=12.4, 8.6, 3.4 Hz, 2H), 2.83 (t, J=6.5 Hz, 1H), 2.16-2.09 (m, 2H), 2.08 (s, 3H), 2.05

(s, 3H), 1.87 (dtd, J=12.1, 8.1, 3.5 Hz, 2H), 1.53 (s, 3H), 1.21 (s, 3H); $^{13}C$ NMR (101 MHz, MeOD) δ 172.59, 171.76, 171.36, 166.16, 162.38, 157.61, 152.04, 151.92, 145.03, 142.46, 130.80, 129.66 (2C), 123.59 (2C), 118.05 (2C), 118.02 (2C), 115.67, 106.20, 103.33, 98.57, 92.78, 86.55, 85.61, 81.72, 77.88, 73.99, 64.84, 64.58, 61.28, 48.20 (2C), 43.59, 31.47 (2C), 27.52, 25.45, 20.66, 20.51; HRMS (ESI+) m/z calcd for $C_{42}H_{47}F_3N_5O_{14}$ [M+H] 902.3072, found 902.3098.

(2S,3S,4S)-2-((1R)-2-Amino-1-((2S,5R)-5-(2,4-dioxo-3,4-dihydropyrimidin-1(2H)-yl)-3,4-dihydroxy-tetrahydrofuran-2-yl)-2-oxoethoxy)-3,4-dihydroxy-N-(4-(4-(4-(trifluoromethoxy)phenyl)-piperidin-1-yl)benzyl)-3,4-dihydro-2H-pyran-6-carboxamide (8). A solution of 35 (37 mg, 0.040 mmol) in a 4:1 mixture of TFA and $H_2O$ (0.80 mL) was stirred for 4 h at r.t., and concentrated in vacuo. A solution of the crude alcohol in a 5:1 mixture of MeOH and $Et_3N$ (0.80 mL) was stirred for 10 h at r.t., and concentrated in vacuo. The crude mixture was purified by reverse-phase HPLC [column: Luna® (C18, 10 μm, 100 Å, 250×10 mm), solvents: 35:65 MeOH:$H_2O$, flow rate: 3.0 mL/min, UV: 254 nm, retention time: 15 min] to afford DM-CPPB (8, 29 mg, 91%): $^1H$ NMR (400 MHz, Methanol-d4) δ 7.92 (d, J=8.1 Hz, 1H), 7.20 (d, J=3.1 Hz, 2H), 7.18 (d, J=3.5 Hz, 2H), 7.02 (d, J=9.1 Hz, 2H), 6.96 (d, J=8.6 Hz, 2H), 6.01 (d, J=4.4 Hz, 1H), 5.80 (d, J=3.0 Hz, 1H), 5.73 (d, J=8.1 Hz, 1H), 5.14 (d, J=6.7 Hz, 1H), 4.66 (d, J=1.8 Hz, 1H), 4.57-4.51 (m, 1H), 4.50 (dd, J=6.7, 1.7 Hz, 1H), 4.41-4.31 (m, 3H), 4.16 (dd, J=6.6, 5.0 Hz, 1H), 4.04 (dd, J=4.9, 3.0 Hz, 1H), 3.88 (dd, J=6.7, 4.5 Hz, 1H), 3.47 (t, J=6.2 Hz, 2H), 3.27 (d, J=7.2 Hz, 1H), 3.07 (ddd, J=17.0, 8.1, 4.0 Hz, 2H), 2.37-2.29 (m, 1H), 2.16-2.07 (m, 2H), 1.86 (dtd, J=12.3, 8.2, 3.5 Hz, 2H); $^{13}C$ NMR (101 MHz, MeOD) δ 174.07, 170.14, 166.22, 163.14, 157.62, 152.12, 151.99, 144.89, 141.84, 131.07, 129.64 (2C), 123.58 (2C), 118.08 (2C), 118.03 (2C), 116.78, 108.52, 102.45, 101.32, 91.15, 84.20, 78.81, 75.49, 74.02, 71.19, 69.27, 63.69, 60.09, 47.81 (2C), 31.46 (2C); HRMS (ESI+) m/z calcd for $C_{35}H_{39}F_3N_5O_{12}$ [M+H] 778.2547, found 778.2573.

(2R)-2-(((2S,3S,4S)-3,4-Dihydroxy-6-(((4-(4-(4-(trifluoromethoxy)phenyl)piperidin-1-yl)benzyl)-amino)-methyl)-3,4-dihydro-2H-pyran-2-yl)oxy)-2-((2S,5R)-5-(2,4-dioxo-3,4-dihydropyrimidin-1(2H)-yl)-4-hydroxy-3-methoxytetrahydrofuran-2-yl)acetamide (9). To a stirred solution of 16 (5.8 mg, 0.0092 mmol) and DMSO (0.065 mL, 0.92 mmol) in a 5:1 mixture of $CH_2Cl_2$ and $Et_3N$ (0.5 mL) was added $SO_3$pyridine (15 mg, 0.092 mmol). After being stirred for 2 h at r.t., the reaction mixture was added $H_2O$ (0.1 mL) and passed through a silica gel pad ($CHCl_3$/MeOH=93/7) to afford the crude 17: this was used without purification. To a stirred solution of the crude 17 and 34 (17 mg, 0.046 mmol) in $CH_3CN$ (0.5 mL) was added $NaB(CN)H_3$ (5.8 mg, 0.092 mol). After being stirred for 3 h at r.t., the reaction was quenched with aq. $NaHCO_3$, and extracted with $CHCl_3$/MeOH (9/1). The combined organic extracts were dried over $Na_2SO_4$ and concentrated in vacuo. The crude product was passed through a silica gel pad ($CHCl_3$/MeOH=9/1). The solution of the crude product in a 5:1 mixture of MeOH and $Et_3N$ (0.5 mL) was stirred for 8 h at r.t., and concentrated in vacuo. The crude mixture was purified by reverse-phase HPLC [column: Luna® (C18, 10 μm, 100 Å, 250×10 mm), solvents: 65:35 MeOH:$H_2O$, flow rate: 3.0 mL/min, UV: 254 nm, retention time: 15 min] to afford CPPA (9, 4.6 mg, 65% for 3 steps): $^1H$ NMR (400 MHz, Methanol-d4) δ 8.02 (d, J=8.1 Hz, 1H), 7.24 (d, J=8.5 Hz, 2H), 7.19 (d, J=8.5 Hz, 2H), 7.03 (d, J=8.9 Hz, 2H), 6.99 (d, J=8.5 Hz, 2H), 5.90 (d, J=5.4 Hz, 1H), 5.76 (d, J=7.8 Hz, 1H), 5.73 (d, J=8.1 Hz, 1H), 5.06 (d, J=6.6 Hz, 1H), 4.57 (dd, J=6.4, 3.0 Hz, 1H), 4.52 (td, J=4.4, 1.7 Hz, 1H), 4.33 (t, J=5.2 Hz, 1H), 4.26 (d, J=26.3 Hz, 1H), 4.18 (d, J=1.6 Hz, 1H), 3.90-3.77 (m, 3H), 3.55-3.50 (m, 2H), 3.49 (s, 3H), 3.15-3.06 (m, 3H), 2.16-2.07 (m, 3H), 1.86 (m, J=8.8, 4.3 Hz, 3H); $^{13}C$ NMR (101 MHz, MeOD) δ 174.07, 165.86, 163.68, 157.58, 151.26, 144.88, 142.07, 131.25, 129.37 (2C), 123.22 (2C), 118.03 (4C), 109.57, 102.60, 100.40, 90.92, 83.37, 80.46, 77.56, 74.63, 73.77, 73.15, 67.78, 63.30, 58.33, 48.19 (2C), 43.21, 30.74 (2C); HRMS (ESI+) m/z calcd for $C_{36}H_{43}N_3F_5O_{12}$ [M+H] 794.2860, found 794.2877.

(2R)-2-(((2S,3S,4S)-3,4-dihydroxy-6-(((4-(4-(4-(trifluoromethoxy)phenyl)pipendin-1-yl)-benzyl)amino)methyl)-3,4-dihydro-2H-pyran-2-yl)oxy)-2-((2S,5R)-5-(2,4-dioxo-3,4-dihydro-pyrimidin-1(2H)-yl)-3-hydroxy-4-methoxytetrahydrofuran-2-yl)acetamide (10). To a stirred solution of 26 (4.6 mg, 0.0073 mmol) and DMSO (0.052 mL, 0.73 mmol) in a 5:1 mixture of $CH_2Cl_2$ and $Et_3N$ (0.5 mL) was added $SO_3$pyridine (12 mg, 0.073 mmol). After being stirred for 2 h at r.t., the reaction mixture was added $H_2O$ (0.1 mL) and passed through a silica gel pad ($CHCl_3$/MeOH=93/7) to afford the crude 29. To a stirred solution of the crude 29 and 34 (13 mg, 0.036 mmol) in $CH_3CN$ (0.5 mL) was added $NaB(CN)H_3$ (4.6 mg, 0.073 mol). After being stirred for 3 h at r.t., the reaction was quenched with aq. $NaHCO_3$, and extracted with $CHCl_3$/MeOH (9/1). The combined organic extracts were dried over $Na_2SO_4$ and concentrated in vacuo. The crude product was passed through a silica gel pad ($CHCl_3$/MeOH=9/1). A solution of the crude product in a 5:1 mixture of MeOH and $Et_3N$ (0.5 mL) was stirred for 8 h at r.t., and concentrated in vacuo. The crude mixture was purified by reverse-phase HPLC [column: Luna® (C18, 10 μm, 100 Å, 250×10 mm), solvents: 65:35 MeOH:$H_2O$, flow rate: 3.0 mL/min, UV: 254 nm, retention time: 15 min] to afford I-CPPA (10, 3.6 mg, 63% for 3 steps): $^1H$ NMR (400 MHz, Methanol-d4) δ 8.04 (d, J=8.1 Hz, 1H), 7.23 (d, J=8.4 Hz, 2H), 7.19 (d, J=8.7 Hz, 2H), 7.03 (d, J=9.1 Hz, 2H), 6.98 (d, J=8.5 Hz, 2H), 5.94 (d, J=3.6 Hz, 1H), 5.74 (d, J=8.1 Hz, 1H), 5.72 (d, J=8.1 Hz, 1H), 5.06 (s, 1H), 4.59-4.52 (m, 2H), 4.43-4.38 (m, 1H), 4.28 (t, J=5.4 Hz, 1H), 4.25 (t, J=4.4 Hz, 1H), 4.21 (d, J=1.5 Hz, 1H), 4.14 (dd, J=8.3, 4.9 Hz, 1H), 3.88-3.85 (m, 2H), 3.82 (d, J=8.2 Hz, 2H), 3.53 (s, 3H), 3.13 (ddd, J=12.3, 8.7, 3.3 Hz, 2H), 2.11 (d, J=9.7 Hz, 3H), 1.87 (ddt, J=13.3, 8.9, 4.1 Hz, 3H); $^{13}C$ NMR (101 MHz, MeOD) δ 173.92, 165.98, 162.46, 157.87, 151.93, 143.90, 140.73, 130.53, 129.43 (2C), 123.29 (2C), 118.10 (2C), 117.87 (2C), 109.98, 103.08, 100.53, 91.27, 83.47, 80.53, 78.03, 74.70, 73.54, 67.84, 63.75, 58.42, 57.46, 48.20, 43.48 (2C), 31.49 (2C); HRMS (ESI+) m/z calcd for $C_{36}H_{43}N_3F_5O_{12}$ [M+H] 794.2860, found 794.2885.

Scheme 3

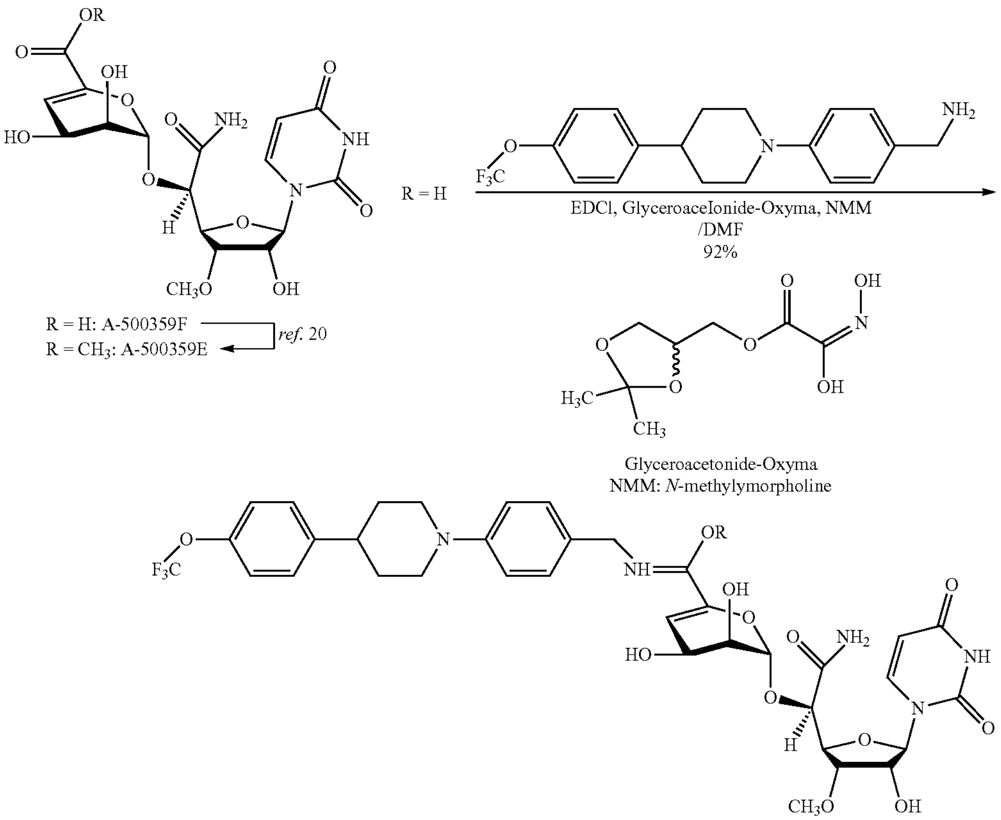

CPPB(5)

Purifications: DOWEX 50W x 4 (MeOH: NH4OH = 4:1)
Reverse HPLC (Luna 10u $C_{18}$ 100A 250 x 10mm,
MeOH: $H_2O$ = 65:35

Previously, a natural product A-5003659E was used to develop novel capuramycin analogues with strong MraY inhibitory activity (Hotoda et. al. 2003). Its free-carboxylic acid analogue, A-500359F was also isolated from the capuramycin-producing strain, *Streptomyces griseus* Sank 60196. Although, the currently available synthetic schemes for capuramycin analogues (e.g., Scheme 2) include a relatively short number of chemical steps, a semi-synthetic approach is more feasible to deliver large quantities of CPPB for pharmacological studies. To establish semi-synthesis of CPPB, A-500359F was first synthesized from the CAP-synthetic intermediate 32 (Scheme 2) in a single step. Amide-forming reaction of synthetic A-500359F with (((trifluormethoxy)-phenoxy) piperidin-1-yl)phenyl)methylamine (34) was performed under an optimized condition using EDCl, glyceroacetonide-Oxyma, and NMM in DMF. All coupling reagents could be removed by partitions between $CHCl_3$ and water and evaporation. The crude product was passed through DOWEX 50W×4 column (MeOH: $NH_4OH$=4:1) to provide CPPB with >95% purity, which was further purified by C18-reverse HPLC (MeOH: $H_2O$=65:35) to yield pure CPPB (Scheme 3).

(2S,3S,4S)-2-((1R)-2-amino-1-(2S,5R)-5-(2,4-dioxo-3,4-dihydropyrimidin-1(2H)-yl)-4-hydroxy-3-methoxytetrahydrofuran-2-yl)-2-oxoethoxy)-3,4-dihydroxy-3,4-dihydro-2H-pyran-6-carboxylic acid (A-500359F). A solution of 32 (18 mg, 29 μmol in a 5:1 mixture of MeOH and $Et_3N$ (0.5 mL) was stirred for 5 h at r.t., and concentrated in vacuo. The crude mixture was purified by reverse-phase HPLC [column: Luna® (C18, 10 μm, 100 Å, 250×10 mm), solvents: 15:85 MeOH:$H_2O$, flow rate: 3.0 mL/min, UV: 254 nm, retention time: 14 min] to afford A-500359F (12 mg, 96%): $^1$H NMR (400 MHz, Deuterium Oxide) δ 7.75 (d, J=8.1 Hz, 1H), 5.88 (d, J=8.1 Hz, 1H), 5.80 (dd, J=2.5, 1.6 Hz, 1H), 5.78 (d, J=4.0 Hz, 1H), 5.25 (d, J=3.2 Hz, 1H), 4.71 (d, J=2.1 Hz, 1H), 4.48 (dd, J=5.7, 2.1 Hz, 1H), 4.43 (dd, J=4.5, 2.5 Hz, 1H), 4.30 (dd, J=5.1, 4.0 Hz, 1H), 4.12 (ddd, J=4.8, 3.3, 1.7 Hz, 1H), 3.73 (t, J=5.4 Hz, 1H), 3.35 (s, 3H); $^{13}$C NMR (101 MHz, D2O) δ 173.32, 168.26, 166.06, 151.29, 144.11, 140.79, 108.44, 101.93, 98.62, 89.42, 81.99, 78.20, 75.00, 72.10, 64.43, 62.19, 57.93; HRMS (ESI+) m/z calcd for $C_{17}H_{22}N_3O_{12}$ [M+H] 460.1204, found 460.1215.

Synthesis of CPPB (5). To a stirred solution of A-500359F (11 mg, 0.024 mmol), 34 (26 mg, 0.072 mmol), Glyceroacetonide-Oxyma (16 mg, 0.072 mmol) and NMM (26 mL, 0.24 mmol) in DMF (0.49 mL) was added EDCl (23 mg, 0.12 mmol). After being stirred for 5 h at r.t., the reaction mixture was filtered, and diluted with water. The product was extracted with $CHCl_3$/MeOH (9/1). The combined extracts were derived over $Na_2SO_4$, and concentrated in vacuo. The crude mixture was purified by DOWEX 50W×4 (MeOH:$NH_4OH$=4:1) followed by reverse-phase HPLC [column: Luna (C18, 10 mm, 100 Å, 250×10 mm), solvents: 65:35 MeOH:$H_2O$, flow rate: 3.0 mL/min, UV: 254 nm, retention time: 18 min] to afford 5 (17 mg, 92%). All physical data were identical to that of CPPB synthesized in Scheme 2.

((2R,4R,5R,6S)-6-(((2R,3S,4S,5S,6S)-3-acetamido-4,5-dihydroxy-6-(hydroxymethyl)tetrahydro-2H-pyran-2-yl)oxy)-3,4-dihydroxy-5-(3-(4-(4-(4-(trifluoromethoxy)phenoxy)piperidin-1-yl)benzyl)ureido)tetrahydro-2H-pyran-2-yl)methyl((1R)-2-amino-1-(2R,3R,5R)-5-(2,4-dioxo-3,4-dihydropyrimidin-1(2H)-yl)-3,4-dihydroxytetrahydrofuran-2-yl)-2-oxoethyl)carbamate (Compound A) $^{1}$H NMR (400 MHz, Methanol-$d_4$) δ 7.60 (d, J=6.4 Hz, 1H), 7.23 (d, J=8.1 Hz, 2H), 7.19 (d, J=8.8 Hz, 2H), 7.02 (d, J=9.5 Hz, 4H), 5.80 (d, J=3.9 Hz, 1H), 5.69 (d, J=8.0 Hz, 1H), 5.36 (d, J=6.2 Hz, 1H), 4.93 (d, J=4.7 Hz, 1H), 4.84 (d, J=8.1 Hz, 1H), 4.60 (d, J=11.2 Hz, 1H), 4.53 (dt, J=7.8, 4.0 Hz, 1H), 4.49-4.07 (m, 4H), 3.91-3.89 (m, 1H), 3.88-3.85 (m, 1H), 3.83-3.79 (m, 2H), 3.77-3.70 (m, 2H), 3.66-3.46 (m, 8H), 3.25 (t, J=7.3 Hz, 1H), 3.03 (ddd, J=12.1, 8.7, 3.2 Hz, 2H), 2.17-2.08 (m, 2H), 1.89 (s, 3H), 1.92-1.83 (m, 2H). $^{13}$C NMR (101 MHz, MeOD) δ 176.7, 175.6, 170.7, 157.6, 155.9, 154.1, 153.0, 152.0, 143.9, 142.1, 131.3, 129.6 (2C), 123.6 (2C), 118.1 (2C), 118.1 (2C), 105.1, 103.8, 102.7, 101.3, 91.7, 84.9, 80.2, 76.7, 75.4, 74.0, 73.2, 72.5, 71.3, 69.4, 66.0, 65.0, 62.2, 60.5, 54.5, 45.5 (2C), 43.7, 31.5 (2C), 27.3.

((2R,4R,5R,6S)-6-(((2R,3S,4S,5S,6S)-3-acetamido-4,5-dihydroxy-6-(hydroxymethyl)tetrahydro-2H-pyran-2-yl)oxy)-3,4-dihydroxy-5-(3-(4-(4-(4-(trifluoromethoxy)phenoxy)piperidin-1-yl)benzyl)ureido)tetrahydro-2H-pyran-2-yl)methyl((1S)-2-amino-1-((2R,3R,5R)-5-(2,4-dioxo-3,4-dihydropyrimidin-1(2H)-yl)-3,4-dihydroxytetrahydrofuran-2-yl)-2-oxoethyl)carbamate (Compound B) 1H NMR (400 MHz, Methanol-d4) δ 7.61 (d, J=7.3 Hz, 1H), 7.23 (d, J=8.1 Hz, 2H), 7.19 (d, J=8.8 Hz, 2H), 7.02 (d, J=9.5 Hz, 4H), 5.81 (d, J=4.3 Hz, 1H), 5.74 (d, J=8.0 Hz, 1H), 5.42 (d, J=3.6 Hz, 1H), 4.94 (d, J=5.1 Hz, 1H), 4.80 (d, J=8.1 Hz, 1H), 4.57 (d, J=11.3 Hz, 1H), 4.53 (dt, J=7.8, 4.0 Hz, 1H), 4.49-4.07 (m, 4H), 3.91-3.89 (m, 1H), 3.88-3.85 (m, 1H), 3.83-3.79 (m, 2H), 3.77-3.70 (m, 2H), 3.66-3.46 (m, 8H), 3.25 (t, J=7.3 Hz, 1H), 3.03 (ddd, J=12.1, 8.7, 3.2 Hz, 2H), 2.17-2.08 (m, 2H), 1.97 (s, 3H), 1.92-1.83 (m, 2H). $^{13}$C NMR (101 MHz, MeOD) δ 177.3, 175.6, 170.7, 157.6, 156.7, 154.1, 153.0, 152.0, 143.9, 142.1, 131.3, 129.6 (2C), 123.6 (2C), 118.1 (2C), 118.1 (2C), 105.1, 103.8, 102.7, 101.3, 91.7, 84.9, 80.2, 77.5, 75.4, 74.0, 73.2, 72.5, 71.3, 70.6, 66.0, 65.0, 62.2, 60.5, 56.8, 45.5 (2C), 43.7, 31.5 (2C), 27.3.

Example 2: Enzymatic Inhibition

CAP (1) and its three analogues, OM-CAP (2), I-CAP (3), and DM-CAP (4) were evaluated in enzyme inhibitory assays against bacterial phosphotransferases, MraY and WecA, and archaeal and human dolichyl-phosphate GlcNAc-1-phosphotransferases, AglH and DPAGT1. CAP is a selective MraY inhibitor that does not display inhibitory activity against WecA, AglH, and DPAGT1 (Table 1). Previously, OM-CAP (2) was identified as a selective WecA inhibitor ($IC_{50}$ 0.060 μM) that does not possess MraY inhibitory activity (ICso >50 μM (entry 2 in Table 1). OM-CAP (2) was shown to have inhibitory activity against AglH and DPAGT1 with the $IC_{50}$ values of 13.5 and 3.5 μM, respectively (entry 2). I-CAP (3) showed enzyme inhibitory activity against MraY, WecA, AglH, and DPAGT1 with the $IC_{50}$ between 7.5-20 μM concentrations (entry 3). On the contrary, DM-CAP (4) showed only a weak WecA inhibitory activity ($IC_{50}$35.0 μM) (entry 4).

MraY, WecA, AglH, and DPAGT1 enzyme inhibitory activity assays for the six (((trifluormethoxy)phenoxy) piperidin-1-yl)phenyl)methylamine analogues revealed that CPPB (5) and I—CPPB (6) are high nM range DPAGT1 inhibitors (entries 5 and 6 in Table 1), however, the O-methylation and demethylation analogues (OM-CPPB (7) and DM-CPPB (8)) turned out to be very low- or no-DPAGT1 inhibitor (entries 7 and 8). The secondary amine analogues, CPPA (9) and I-CPPA (10), did not inhibit all phosphotransferases tested in Table 1 at 50 μM concentration (entries 9 and 10). CPPB was determined to be three times stronger DAPGT1 inhibitor ($IC_{50}$ 0.20 μM) than I—CPPB (entry 5 vs. 6). I—CPPB did not display MraY inhibitory activity, but showed a very weak WecA and AglH enzyme inhibitory activity (entry 6). Interestingly, difference in these phosphotransferase inhibitory profiles between CPPB and I—CPPB correlate with their antimycobacterial activity: CPPB possessing MraY/WecA inhibitory activity killed *Mycobacterium tuberculosis* $H_{37}$Rv, *Mycobacterium avium* 2285, *Mycobacterium smegmatis* (ATCC607) with the MIC values 6.25-12.5 μg/mL. In contrast, I—CPPB, which does not have MraY inhibitory activity, did not show growth inhibitory activity against these *Mycobacterium* spp. at 50 μg/mL.

TABLE 1

| | | $IC_{50}$ (μM) | | | |
|---|---|---|---|---|---|
| Entry | Compound | MraY (*Hydrogenivirga* sp.) | WecA (*E. coli*) | AglH (*M. jannaschii*) | DPAGT1 (Human) |
| 1 | Capuramycin | 0.13 | >50 | >50 | >50 |
| 2 | O-Methyl capuramycin | >50 | 0.060 | 2.5 | 4.5 |
| 3 | iso-Capuramycin | 8.5 | 30.0 | 20.0 | 11.5 |
| 4 | Dimethyl capuramycin | >50 | 35.0 | >50 | >50 |
| 5 | Capuramycin phenoxypiperidin-benzylamide (CPPB) | 10.3 | 0.10 | 0.15 | 0.20 |
| 6 | iso-Capuramycin phenoxy-piperidinbenzylamide (I-CPPB, 6) | >50 | 20.0 | 15.0 | 0.60 |
| 7 | O-Methyl capuramycin phenoxy-piperidinbenzylamide (OM-CPPB, 7) | 5.0 | 10.0 | 30.0 | 20.0 |
| 8 | Demethyl capuramycin phenoxy-piperidinbenzylamide (DM-CPPB, 8) | >50 | 30.0 | >50 | >50 |

TABLE 1-continued

| | | IC50 (μM) | | | |
|---|---|---|---|---|---|
| Entry | Compound | MraY (*Hydrogenivirga* sp.) | WecA (*E. coli*) | AglH (*M. jannaschii*) | DPAGT1 (Human) |
| 9 | Capuramycin phenoxypiperidin-benzylamine (CPPA, 9) | >50 | >50 | >50 | >50 |
| 10 | iso-Capuramycin phenoxypiperidin-benzylamine (I-CPPA, 10) | >50 | >50 | >50 | >50 |
| 11 | Tunicamycin (11) | 2.9 | 0.15 | 13.2 | 1.5 |

Expression and purification of HyMraY. The gene mraY of *Hydrogenivirga* spp. 128-5-R1-1 was cloned with a N-terminal His6 tag into a pET22b vector. The plasmid was transformed and expressed in *E. coli* NiCo21(DE3) pLEMO competent cells. The proteins were purified using a nickel, cation exchange, and size exclusion chromatography. The final storage buffer was 20 mM HEPES pH 7.5, 100 mM NaCl, 10% glycerol, 5 mM 3ME, 0.15% decyl 3-D-maltopyranoside (DM).

Expression and purification of MjAglH. The gene mj1113 of *Methanocaldococcus jannaschii* DSM 2661 was cloned with a N-terminal His9 tag into a pET33b-derived vector. The plasmid was transformed and expressed in *E. coli* NiCo21(DE3) pLEMO competent cells. The proteins were purified using cobalt and size exclusion chromatography. The final storage buffer was 20 mM Tris-HCl, pH 7.5, 100 mM NaCl, 5% glycerol, 5 mM 3ME, 0.15% DM.

Preparation of membrane fraction P-60 containing WecA. *E. coli* B21 wecA strain were harvested by centrifugation (4,700 rpm) at 4° C. followed by washing with 0.9% saline solution (thrice). The washed cell pellets were washed with homogenization buffer (containing 50 mM K2HPO4, 5 mM MgCl2, 5 mM 1,4-dithio-DL-threitol, and 10% glycerol, pH=7.2) (thrice), and approximately 5 g of pellet (wet weight) was collected. The washed cell pellets were suspended in homogenization buffer and disrupted by probe sonication on ice (5 s on and 2 s off for 1 min, then cool down for 1.5 min., 5 cycles, cool down for 15 min, and then, 5 s on and 2 s off for 1 min., cool down for 1.5 min, 5 cycles). The resulting suspension was centrifuged at 4,700×g for 15 min. at 4° C. to remove unbroken cells. The lysate was centrifuged at 25,000×g for 20 min. at 4° C. The supernatant was subjected to ultracentrifugation at 60,000×g for 1 h at 4° C. The supernatant was discarded, and the membrane fraction containing WecA enzyme (P-60) was suspended in the Tris-HCl buffer (pH=7.5). Total protein concentrations were approximately 8 to 10 mg/mL. Aliquots were stored in Eppendorf tubes at −80° C.

DPAGT1 expression and purification. DPAGT1 was expressed in suspended Expi293 cells for 36 h. The cells were lysed by drawing through a 26 g needle (10 times) and membrane protein was extracted using buffer containing 1% decyl f3-D-maltopyranoside detergent. DPAGT1 was purified using HA-agarose resin and a superdex 200 size exclusion column.

MraY assay. MraY assay substrates, Park's nucleotide-$N^{ε}$-C6-dansylthiourea, neryl phosphate, were chemically synthesized according to the reported procedures.[7] Park's nucleotide-$N^{ε}$-C6-dansylthiourea (2 mM stock solution, 1.88 jiL), $MgCl_2$ (0.5 M, 5 jiL), KCl (2 M, 5 jiL), Triton X-100 (0.5%, 5.63 jiL), Tris buffer (pH 8.0, 50 mM), neryl phosphate (0.1 M, 2.25 jiL), and inhibitor molecule (0-50 .ig/mL in Tris buffer) were placed in a 1.5 mL Eppendorf tube. To a reaction mixture, P-60 (10 jiL) was added (total volume of reaction mixture: 50 jiL adjust with Tris buffer). The reaction mixture was incubated for 2 h at r.t. (26° C.) and quenched with $CHCl_3$ (100 jiL). Two phases were mixed via vortex and centrifuged at 25,000×g for 10 min. The aqueous phase was assayed via reverse-phase HPLC. The water phase (10 jiL) was injected into HPLC (solvent: $CH_3CN$/0.05 M aq. $NH_4HCO_3$=25:75; UV: 350 nm; flow rate: 0.5 mL/min; column: Kinetex 5 μM C8, 100 A, 150×4.60 mm), and the area of the peak for lipid I-neryl derivative was quantified to obtain the ICso value. The $IC_{50}$ values were calculated from plots of the percentage product inhibition versus the inhibitor.

WecA assay. WecA assay substrate, UDP-Glucosamine-C6-FITC was chemically synthesized according to the reported procedures.[9,11,58] UDP-Glucosamine-C6-FITC (UDP-GlcN-C6-FITC, 2 mM stock solution, 0.56 μL), $MgCl_2$ (0.5 M, 4 μL), β-mercaptoethanol (50 mM, 5 μL), CHAPS (5%, 11.3 μL), Tris buffer (pH 8.0, 50 mM), undecaprenyl phosphate (4 mM, 1.4 μL), and inhibitor molecule (0-50 μg/mL in Tris buffer) were place in a 1.5 μL Eppendorf tube. To a reaction mixture, P-60 (10 μL) was added (total volume of reaction mixture: 50 μL adjust with Tris buffer). The reaction mixture was incubated for 2 h at 37° C. and quenched with n-butanol (150 μL). Two phases were mixed via vortex and centrifuged at 10,000×g for 3 min. The upper organic phase was assayed via reverse-phase HPLC. The organic phase (30 μL) was injected into HPLC (solvent: gradient elution of 85:15 to 95:5 MeOH/0.05 M aq. $NH_4HCO_3$; UV: 485 nm; flow rate: 0.5 mL/min; column: Kinetex 5 μm C8, 100 Å, 150×4.60 mm), and the area of the peak for $C_{55}$-P-P-GlcN-$C_6$-FITC was quantified to obtain the $IC_{50}$ value. The $IC_{50}$ values were calculated from plots of the percentage product inhibition versus the inhibitor concentration.

AglH assay. AglH assays were performed as the procedure described for WecA assays, but used MjAglH and α-dihydroundecaprenyl phosphate ($C_{55}$-dolichyl phosphate) instead of WecA and undecaprenyl phosphate. UDP-GlcN-$C_6$-FITC (2 mM stock solution, 0.56 μL), $MgCl_2$ (0.5 M, 4 μL), β-mercaptoethanol (50 mM, 5 μL), CHAPS (5%, 11.3 μL), Tris buffer (pH 8.0, 50 mM), $C_{55}$-dolichyl phosphate (4 mM, 1.4 μL), and inhibitor molecule (0-50 μg/mL in Tris buffer) were place in a 1.5 μL Eppendorf tube. To a reaction mixture, AglH solution (10 μL) was added (total volume of reaction mixture: 50 μL adjust with Tris buffer). The reaction mixture was incubated for 2 h at 37° C. and quenched with n-butanol (150 μL). Two phases were mixed via vortex and centrifuged at 10,000×g for 3 min. The upper organic phase was assayed via reverse-phase HPLC. The organic phase (30 μL) was injected into HPLC (solvent: gradient elution of 85:15 to 95:5 MeOH/0.05 M aq. $NH_4HCO_3$; UV: 485 nm;

flow rate: 0.5 mL/min; column: Kinetex 5 μm C8, 100 Å, 150×4.60 mm), and the area of the peak for $C_{55}$-P-P-GlcN-$C_6$-FITC was quantified to obtain the $IC_{50}$ value. The $IC_{50}$ values were calculated from plots of the percentage product inhibition versus the inhibitor concentration.

(0.2-20 μM) inhibited cell proliferation of PD002: ca. 20% of cell proliferation was inhibited at time 72 h. These results indicate that DPAGT1 inhibitors may have cytostatic effect again certain cancerous tumors that require DPAGT1 over-expression for their growth.

TABLE 2

| | | $IC_{50}$ (μM) | | | | | | | | | | |
|---|---|---|---|---|---|---|---|---|---|---|---|---|
| No. | Compound | L1210 | KB | SiHa | HCT-116 | DLD-1 | Capan-2 | PANC-1 | AsPC-1 | PD002 | HPNE | Vero |
| 1 | CAP (1) | >50 | >50 | >50 | >50 | >50 | >50 | >50 | >50 | >50 | >50 | >50 |
| 2 | OM-CAP (2) | >50 | >50 | >50 | >50 | >50 | >50 | >50 | >50 | >50 | >50 | >50 |
| 3 | CPPB (5) | >50 | 35.0 | 15.0 | 15.0 | 25.0 | 30.0 | 35.0 | 25.0 | 35.0 | >50 | >50 |
| 4 | I-CPPB (6) | >50 | 35.0 | 25.0 | 25.0 | 35.0 | 40.0 | 45.0 | 30.0 | 50.0 | >50 | >50 |
| 5 | Tunicamycin (11) | 1.70 | 2.50 | 0.92 | 0.92 | 1.25 | 1.50 | 1.50 | 0.45 | 1.50 | 7.5 | 0.78 |

DPAGT1 assay. DPAGT1 assays were performed as the procedure described for AgIH assays, but used DPAGT1.

Example 3: Cytotoxicity of New Capuramycin Analogues, CPPB (5) and I—CPPB (6)

In the capuramycin analogue series, the degree of MraY inhibitory activity correlates with their antimycobaterial activity. Antimycobacterial capuramycin analogues display low in vitro cytotoxicity against mammalian cells, and have been recognized as safe drug leads that have acceptable tolerability in animal models. The toxicity of tunicamycin has been studied extensively in vitro: tunicamycin inhibits growth in many cancer cell lines without selectivity, and has a narrow therapeutic window demonstrated in in vivo studies using mice. The toxicity of tunicamycin is believed to be attributable to its ability to inhibit DPAGT1 enzyme function. Tunicamycin's toxicity, however, cannot be explained solely by its inhibition of DPAGT1.

Figure 2A:
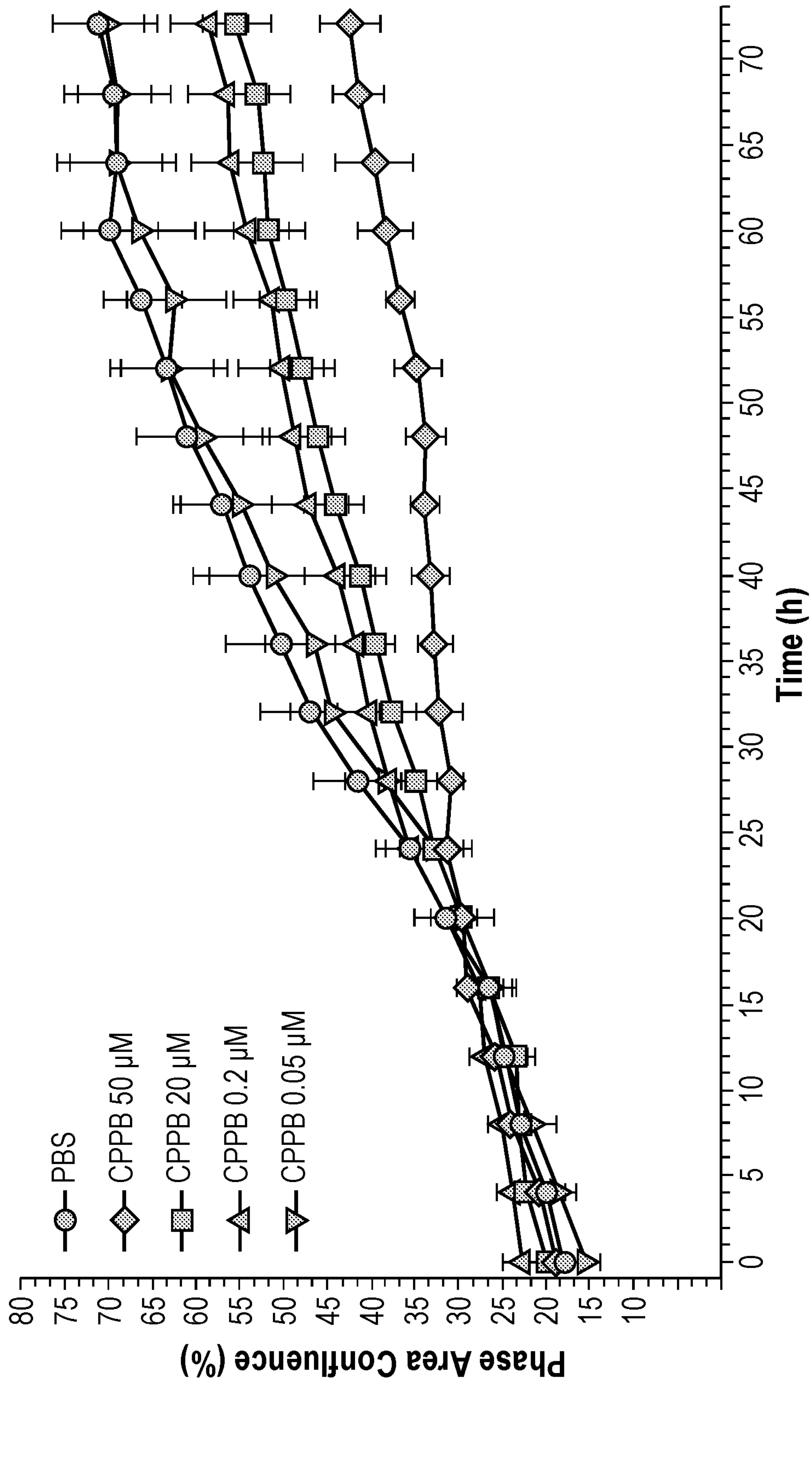
FIGS. 2A, 2B and 2C show phase area confluence of PD002 treated with CPPB in kinetic proliferation assays.

Capuramycin-based DPAGT1 inhibitors, CPPB (5) and I—CPPB (6) inhibited DPAGT1 enzyme with the $IC_{50}$ values of 0.2 and 0.6 μM, respectively. Unlike the MraY-antimycobacterial activity relationship observed for CAP analogues, the DPAGT1 inhibitors, CPPB and I—CPPB, did not show antiproliferative activity against L1210 (a leukemia cell), HPNE (a normal pancreatic ductal cell), and Vero (a normal kidney cell) at 50 μM. They showed various levels of growth inhibitory activity several against solid cancer cell lines such as KB (HeLa, a cervix carcinoma), SiHa (a cervical squamous cell carcinoma), HCT-116 (a colorectal adenocarcinoma), DLP-1 (a colorectal adenocarcinoma), Capan-2 (a pancreatic ductal adenocarcinoma), PANC-1 (a pancreatic ductal carcinoma), AsPC-1 (a pancreatic adenocarcinoma), PD002 (a patient-derived pancreatic adenocarcinoma) in MTT assays ($IC_{50}$ 15-40 μM, Table 2). A lower DPAGT1 inhibitor, tunicamycin (11), showed growth inhibition of all cell lines in Table 2 with the $IC_{50}$ values of 0.78-7.5 μM concentrations (entry 5 in Table 2). Cellular behavior and morphological changes of PD002 treated with CPPB were monitored over time via IncuCyte® live cell analysis imaging system (FIG. 2A).

Figures 2B, 2C:
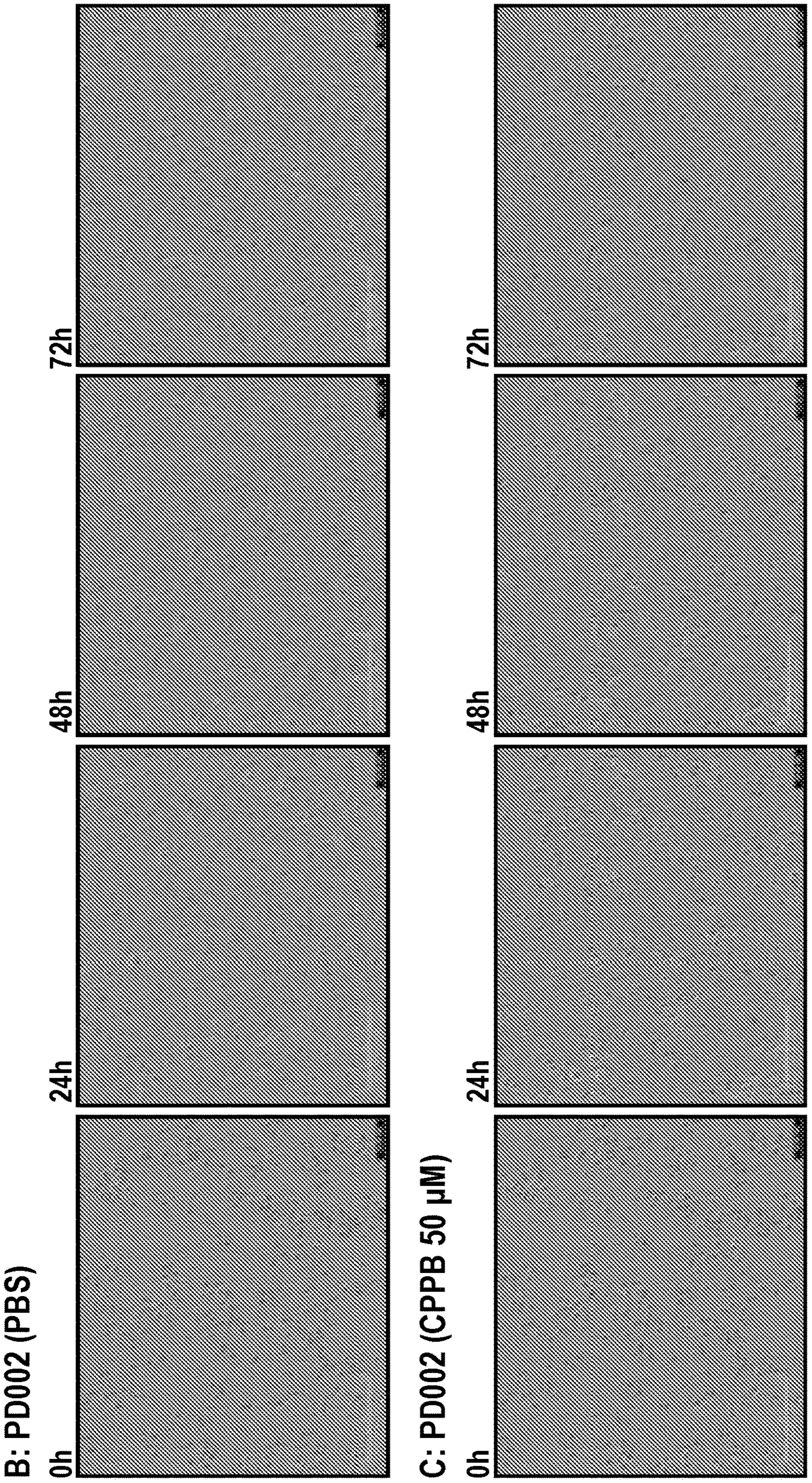

Interestingly, 10-13% of phase area confluent of PD002 culture (time 0 h) remained the same after 72 h for the CPPB-treated cells (50 μM), whereas, ca. 70% of confluence was reached for the control PD002 culture (PBS) (FIGS. 2B and 2C). Although morphological changes were subtle over time (0-72 h), cell viability assessed by the MTT reduction assay revealed that PD002 cells treated with CPPB (50 μM) was significantly decreased (Table 2). Exposure of CPPB Cell lines. The human primary PDAC cell lines PANC-1 (ATCC CRL 1469); Capan-2 (ATCC HTB-80) and metastatic PDAC cell lines Capan-1 (ATCC HTB-79), AsPC-1 (ATCC CRL-1682), L1210 (ATCC CCL-219), KB (ATCC CCL-17), HeLa, SiHa (ATCC HTB-35), HCT-116 (ATCC CCL-247), DLD-1 (ATCC CCL221), hTERT-HPNE (ATCC CRL-4023), Vero (ATCC CCL-81) were purchased from the ATCC. The cell lines were cultured and maintained in the media as recommended by the supplier. The cell lines were regularly tested for mycoplasma contamination and authenticated. In addition to ATCC cell lines, Dr. Glazer's lab generated patient-derived PDAC cell line, PD002. PD002 Cells were maintained and cultured in DMEM medium supplemented with 20% FBS and 100 IU/mL penicillin and incubated at 37° C. with 5% $CO_2$.

MTT cytotoxicity assay. To study the effect of treatment with DPAGT1 inhibitors on the growth and proliferation of cells, a fixed number of cells ($5\times10^4$ cells/well, 196 μL) were plated in a 96 well plate. Into each well 5 μL of drug concentration was added. After 72 h of incubation with drugs at 37° C., 5% $CO_2$, 10 μL of MTT solution (5 mg/mL in PBS) was added and incubated another 3 h at 37° C., 5% $CO_2$. The medium was removed, and DMSO (200 μL/well) was added. Viability was assessed on the basis of cellular conversion of MTT into a purple formazan product. The absorbance of the colored formazan product was measured at 570 nm by BioTek Synergy HT Spectrophotometer.

Kinetic Proliferation Assay. To study the effect of treatment with DPAGT1 inhibitors on the growth and proliferation of cells, a fixed number of cells ($2\times10^4$) were plated in multiple wells of a 96 well plate, incubated for 24 h to let cells settle down. Then, CPPB (5) was added (0-50 μM). Images were obtained every 4 h using an IncuCyte Live-Cell Imaging System (Essen BioScience, Ann Arbor, MI). After 72 h, cell proliferation was quantified using the metric phase object confluence (POC), a measurement of the area of the field of view that is covered by cells, which is calculated by the integrated software.

Scratch Assay. A confluent monolayer was formed in 24-well plates. The monolayer was scratched by a sterile 200 μL pipette tip and washed with PBS to remove cell debris. Complete medium with CPPB (5) (0, 0.05, 0.1, 0.2 μM) were added and scratched areas were photographed with microscope. The scratched cells were incubated at 37° C., 5% $CO_2$. After 24 h, medium was removed and cells were stained with a 1:1 mixture of crystal violet and PBS for 5 min., washed with PBS twice, and photographed with microscope. Wound areas were measured and recovered areas were calculated.

Example 4: Cell Migratory Inhibition by CPPB (5)

DPAGT1 catalyzes the first step in N-glycan biosynthesis of mammalian cells (FIG. 1). Aberrant N-glycosylation is common in many solid cancers and important for the epithelial to mesenchymal transition program (EMT, a mechanism of metastases). High levels of DPAGT1 protein expression were found in a series of pancreatic cancers (e.g., Panc-1, CAPAN-2, and AsPC-1). Dysregulation of DPAGT1 enzyme leads to disturbances in cell-cell adhesions and may increase epithelial to mesenchymal transition (EMT): these processes increase migratory and invasive capabilities of malignant neoplasms that are the initiation of metastasis in cancer progression, especially pancreatic cancer. Interestingly, there is significant crosstalk between DPAGT1 and the Wnt/β-catenin and Snail pathway where DPAGT1 overexpression leads to 1) accumulation of β-catenin in the cytoplasm and then translocation into the nucleus, and 2) reduction of the Snail expression levels, preventing epithelial-mesenchymal transition.

Figure 3A:
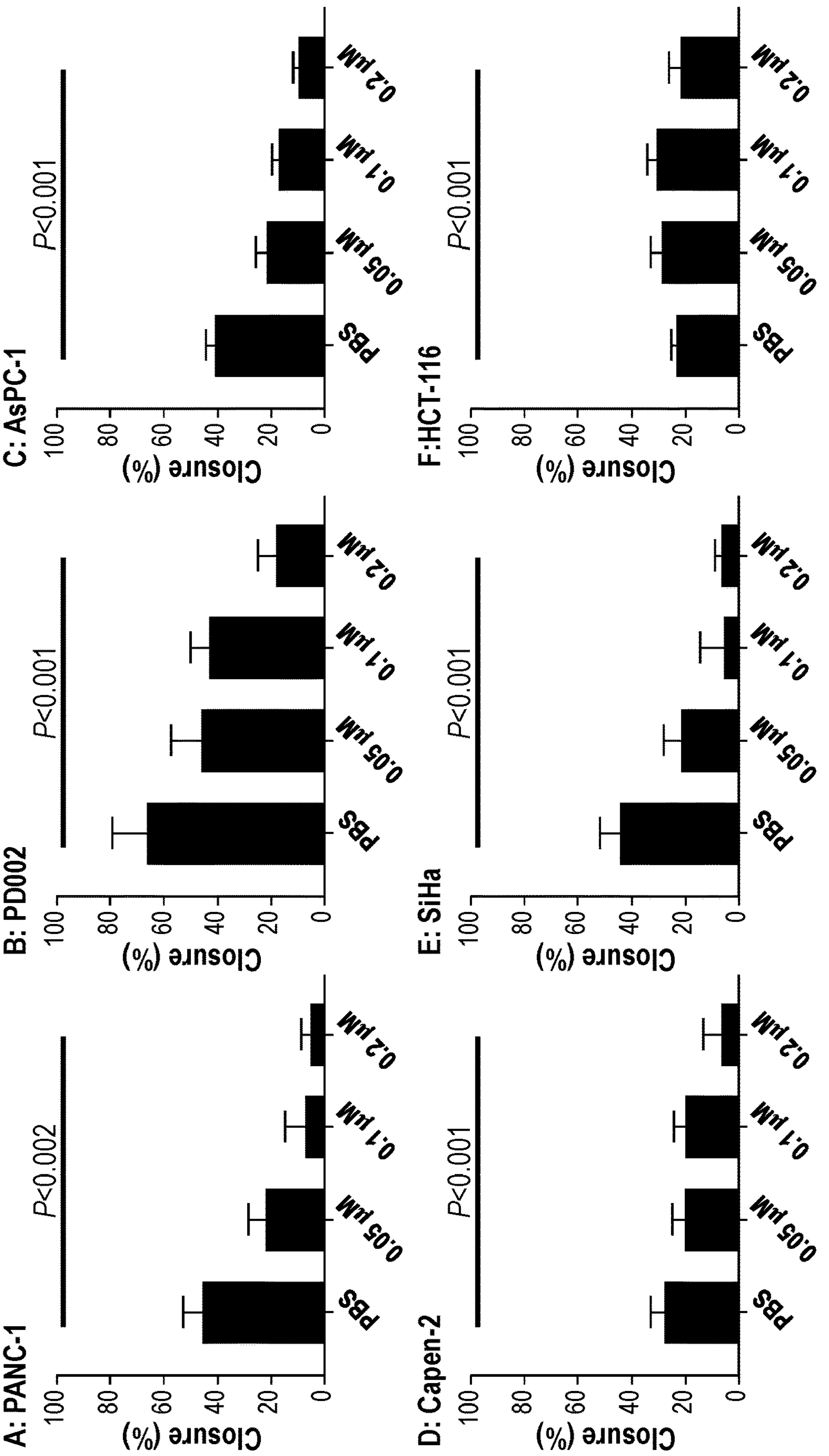
FIGS. 3A and 3B show analyses of migration inhibition of pancreatic cancers, a cervical carcinoma, and a colorectal adenocarcinoma by treatment of CPPB in wound healing (scratch) assays.
Figure 3B:
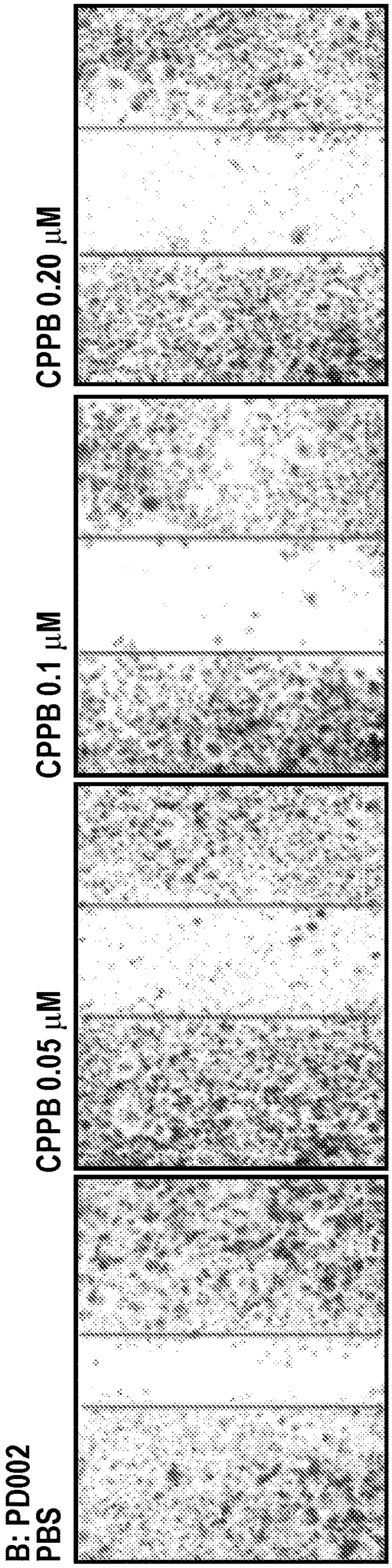

As such, aberrations in these pathways occur in numerous cancers, thus, discovery of small molecules directed towards inhibition of the Wnt and Snail pathways represents an important area of anticancer therapeutics. The degree of cell migration in several commercially available cell lines (Capan-2, PANC-1, and AsPC-1) were observed when treated with the compounds provided herein to determine the effects on cellular motility. After 24 h of three treatment doses (0.05, 0.1, and 0.2 μM) with CPPB (5), inhibition of migration (closing the gap) was measured in a scratch assay (wound healing assay) (FIGS. 3A and 3B). The pancreatic cancer cell lines treated with CPPB migrated far less than the PBS treated (control) cells (FIG. 3A). In these assays, the wound-healing rate of the untreated PD002 cells was 63% in 24 h. In sharp contrast, CPPB treated cells inhibited the wound-healing effectively at its $IC_{50}$ level against DPAGT1 (0.2 μM): the wound-healing rate was approximately 20% (FIG. 3B). The migration inhibition ability of CPPB was thoroughly evaluated compared to gemcitabine, one of the main chemotherapy drugs used to treat pancreatic cancer, and tunicamycin using PD002 cells.

Figure 4:
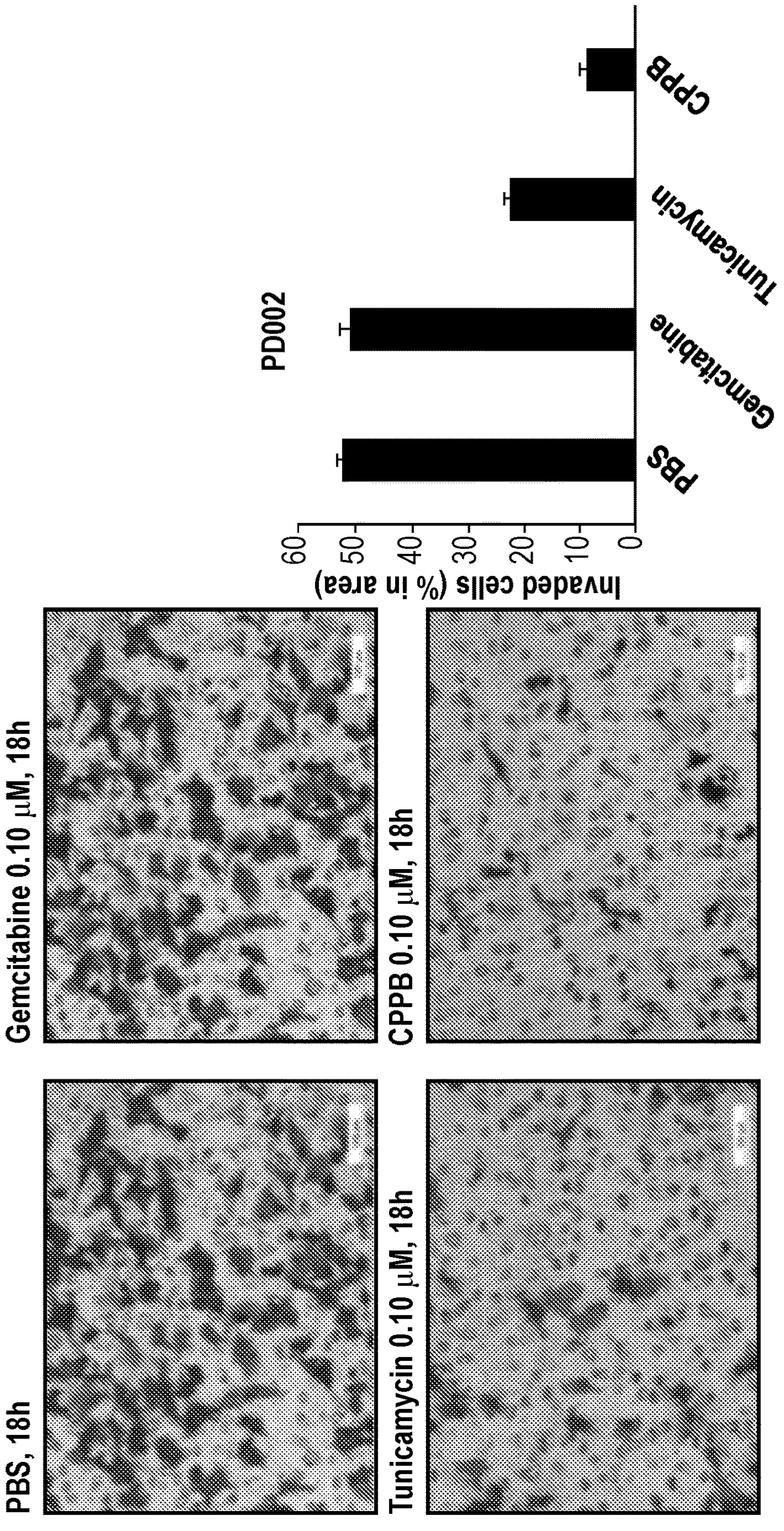
FIG. 4 shows cells migration of PD002 by gemcitabine, tunicamycin, and CPPB via transwell chamber.

Gemcitabine shows a wound-healing rate of 43% at 0.2 μM, and tunicamycin shows 35% at 0.2 μM. Thus, it was concluded that CPPB is more effective in inhibiting cancer cell migration than gemcitabine and tunicamycin. These trends were further confirmed by an endpoint migration assays via Boyden chambers for PD002. In these assays, the cell migrations of PD002 treated with CPPB (0.1 μM) were inhibited on a higher level compared to those with tunicamycin and gemcitabine at the same concentration (0.1 μM) (FIG. 4).

Cell migration assays using Transwell chamber. Cell migration assay was performed using Boyden chamber (thermo fisher). PD002 cells (~$10^4$ cells/mL) were seeded in 96-wells plate (Corning, HTS Transwell-96 Well Permeable Supports, pore size: 8 μm) in FBS free media and the lower chambers were filled with 10% FBS medium. CPPB, tunicamycin, or gemcitabine (0.1 μM) was added to the upper chamber. The cells were incubated for 18 h at 37° C. under 5% $CO_2$. The cells were fixed using 4% paraformaldehyde for 0.5 h and stained with 0.05% crystal violet (300 μL/well), after 0.5 h, images were captured via 10× magnification microscopy.

Example 5: Inhibition of a Zinc-Finger Transcription Factor, Snail (Snail) in the Selected Cancer Cell Lines by CPPB Snail protein is one of the most important transcription factors that induces epithelial to mesenchymal transition (EMT), which converts epithelial cells into migratory mesenchymal cells that are more efficient at metastasizing. EMT induced by overexpression of Snail produces cancer stem-like properties in a number of solid organ cancers. Aberrant expression of Snail leads to loss of expression of E-cadherin, a cell-cell adhesion glycoprotein. Thus, suppression of Snail expression or inhibition of Snail functions represents a potent targeted therapeutic strategy for many cancers.

Figure 5:
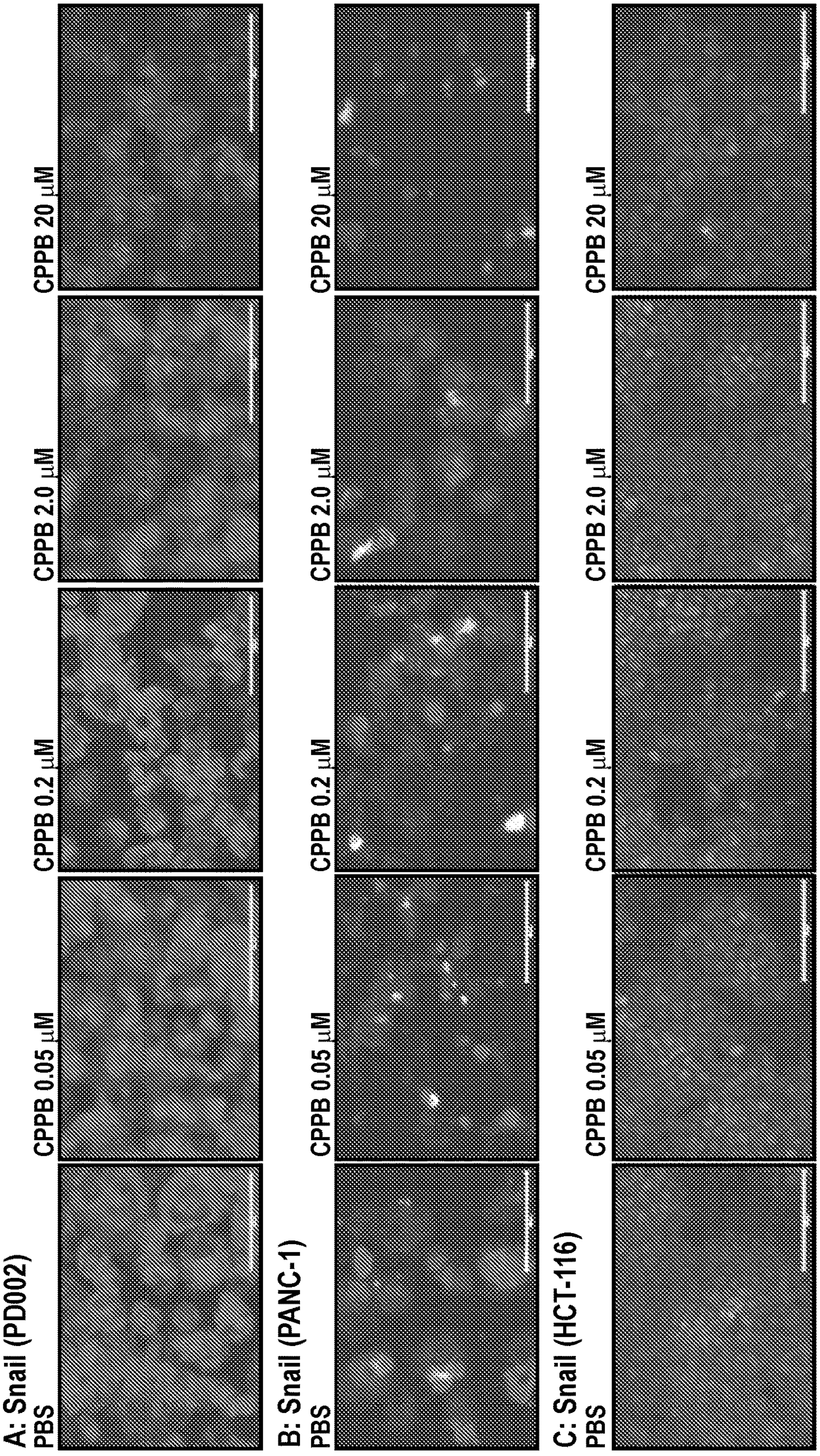
FIG. 5 shows immunofluorescent staining to observe the effect of CPPB on snail in pancreatic cancer cells and a colorectal adenomcarcinoma.
Figure 6:
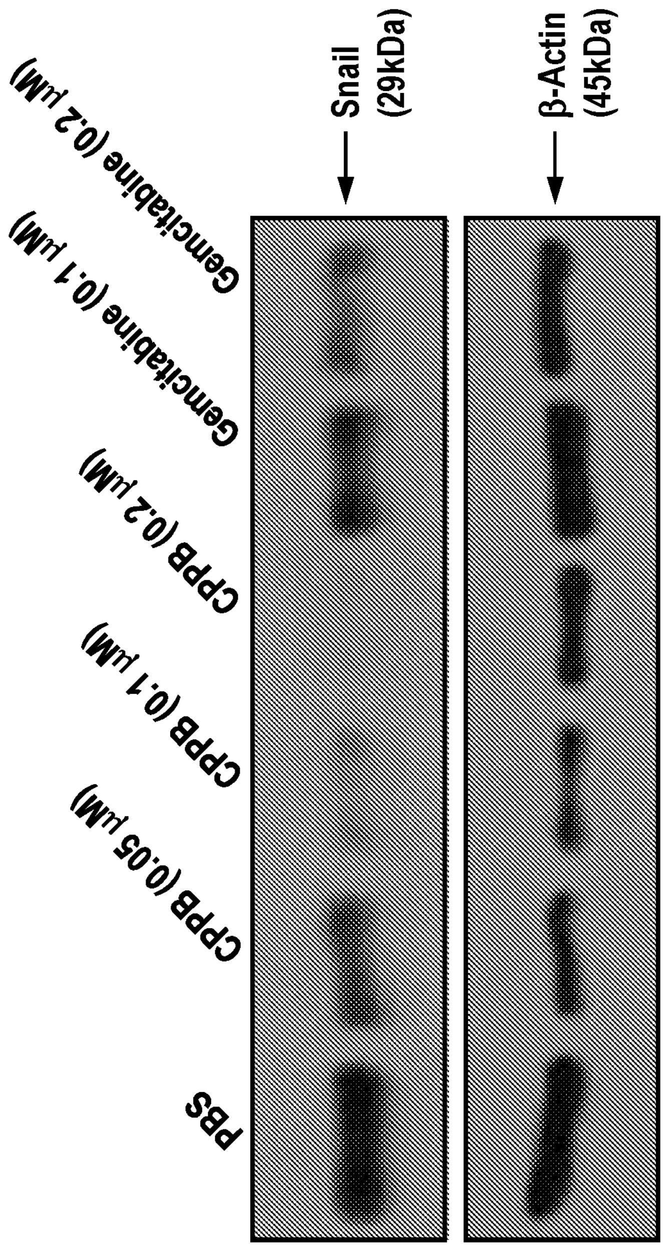
FIG. 6 shows a western blot for CPPB in cervical cancer.

Immunofluorescence assays using an anti-Snail antibody revealed that the fluorescence intensity of Snail was strong in a series of pancreatic cancer cells (PANC-1, AsPC-1, Capan-2, and PD002), and the expression of Snail was decreased by the treatment with CPPB in a concentration dependent manner. Among pancreatic cancer cell lines, only the data for PD002 and PANC-1 are shown in FIG. 5. The Snail expression level of a non-metastatic pancreatic cancer, PANC-1, was much lower than metastatic pancreatic cancers (e.g., PD002 and Capan-2). A few other types of cancer cells such as a colorectal cancer (HCT-116) and a cervical cancer (SiHa) were examined by similarly designed immunofluorescence assays or Western blot assays (FIGS. 5 and 6). The Snail expression in SiHa was inhibited by treatment of CPPB in a concentration dependent manner; at the $IC_{50}$ concentration (0.2 μM against DPAGT1), CPPB effectively inhibited the Snail expression (FIG. 6). In contrast, the Snail expression level in HCT-116 was not noticeably changed by the treatment of CPPB between 0.05 and 2.0 μM concentrations.

Figure 7:
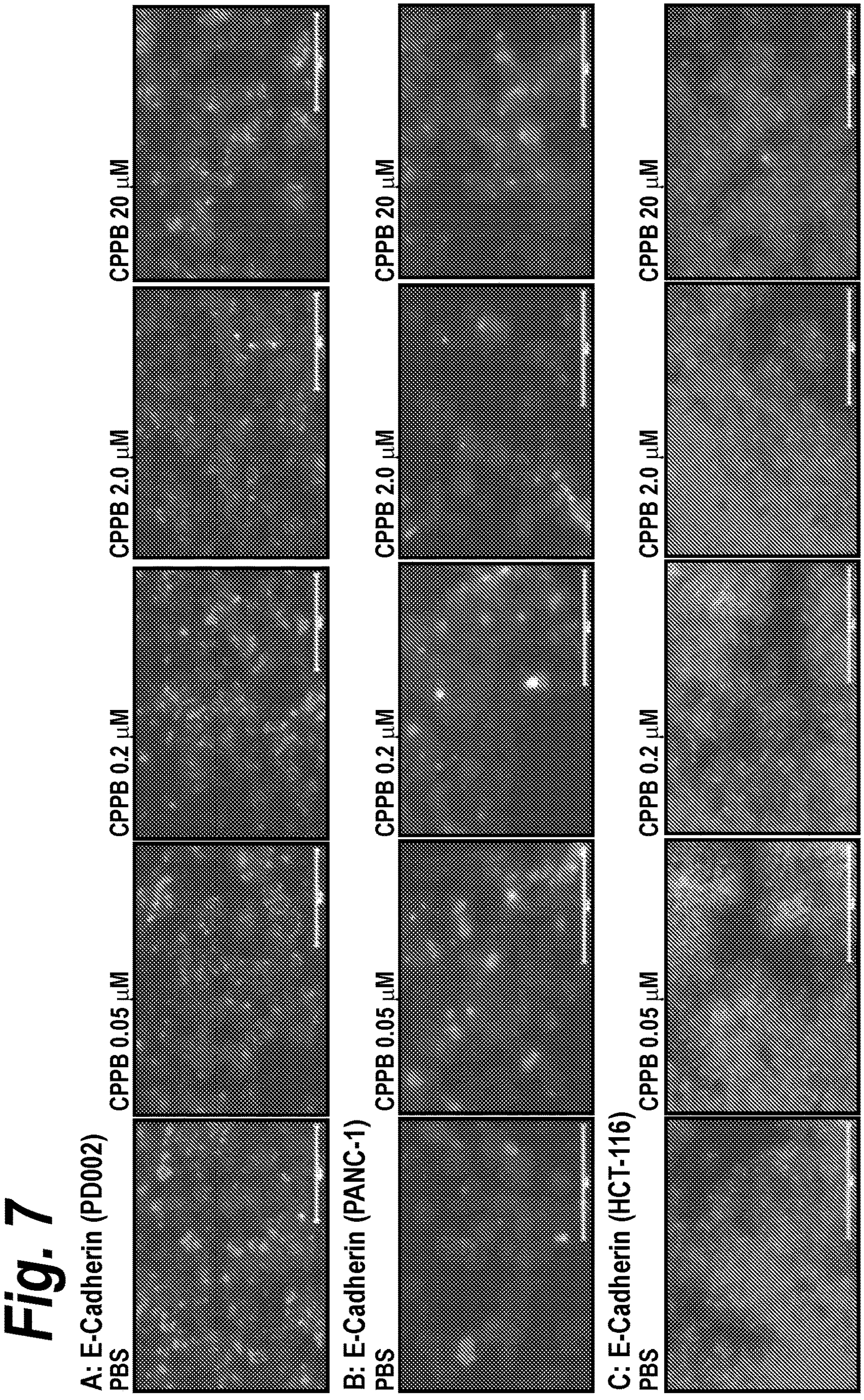
FIG. 7 shows immunofluorescent staining to observe the effect of CPPB on E-cadherin in pancreatic cancer cells and a colorectal adenomcarcinoma.

Interestingly, cell migration of HCT-116 was not inhibited by CPPB demonstrated in the wound healing (scratch) assays (FIG. 3). At the concentrations tested in the scratch assays (0.05-2.0 μM), the E-cadherin expression levels of PD002, PANC-1, and HCT-116 were not changed significantly (FIG. 7).

Example 6: Inhibition of DPAGT1 by CPPB

Figure 8:
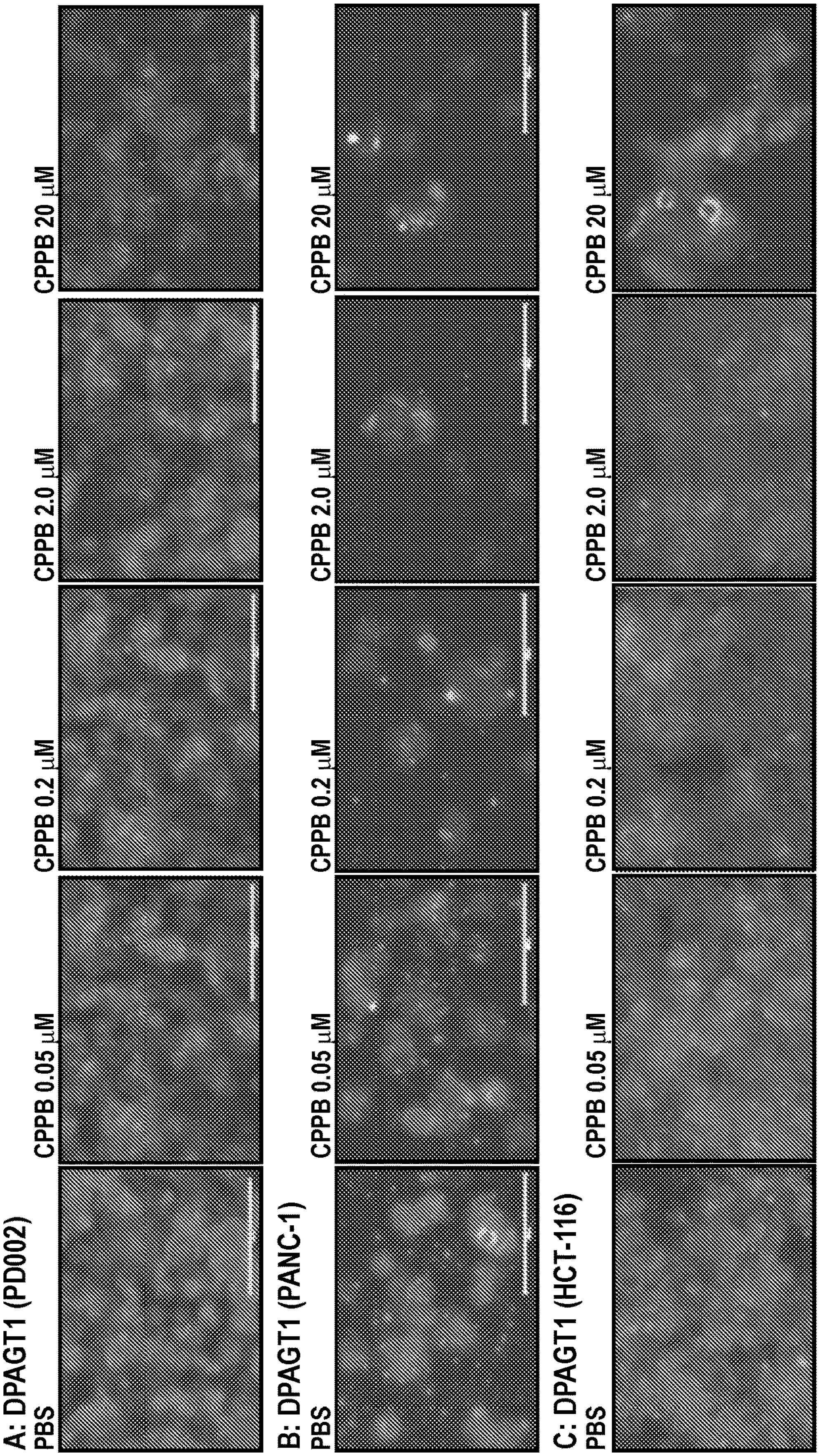
FIG. 8 shows immunofluorescent staining to observe the effect of CPPB on DPAGT1 expression levels in pancreatic cancer cells and a colorectal adenomcarcinoma.

CPPB decreased the DPAGT1 expression level in all pancreatic cancer cell lines examined in FIG. 3: the DPAGT1 expression was apparently inhibited by the $IC_{50}$ concentration of CPPB (0.2 μM) (FIG. 8). However, the DPAGT1 expression of the pancreatic cancer cell lines could not completely be inhibited at a high concentration of CPPB (2-20 μM). In MTT assays, all pancreatic cancers tested remained viable at 20 μM concentration of CPPB (Table 2). In contrast, the DPAGT1 expression levels of a colorectal adenocarcinoma, HCT-116, remained high even at a high concentration of CPPB (20 μM) (FIG. 8). These data imply that the inhibitory effect of CPPB on cell migration varies depending on degree of inhibition of the DPAGT1 expression: at the $IC_{50}$ of CPPB (0.2 μM against DPAGT1), the degree of DPAGT1 expression was decreased by the following order: PANC-1>PD002>>HCT-116.

Figure 9:
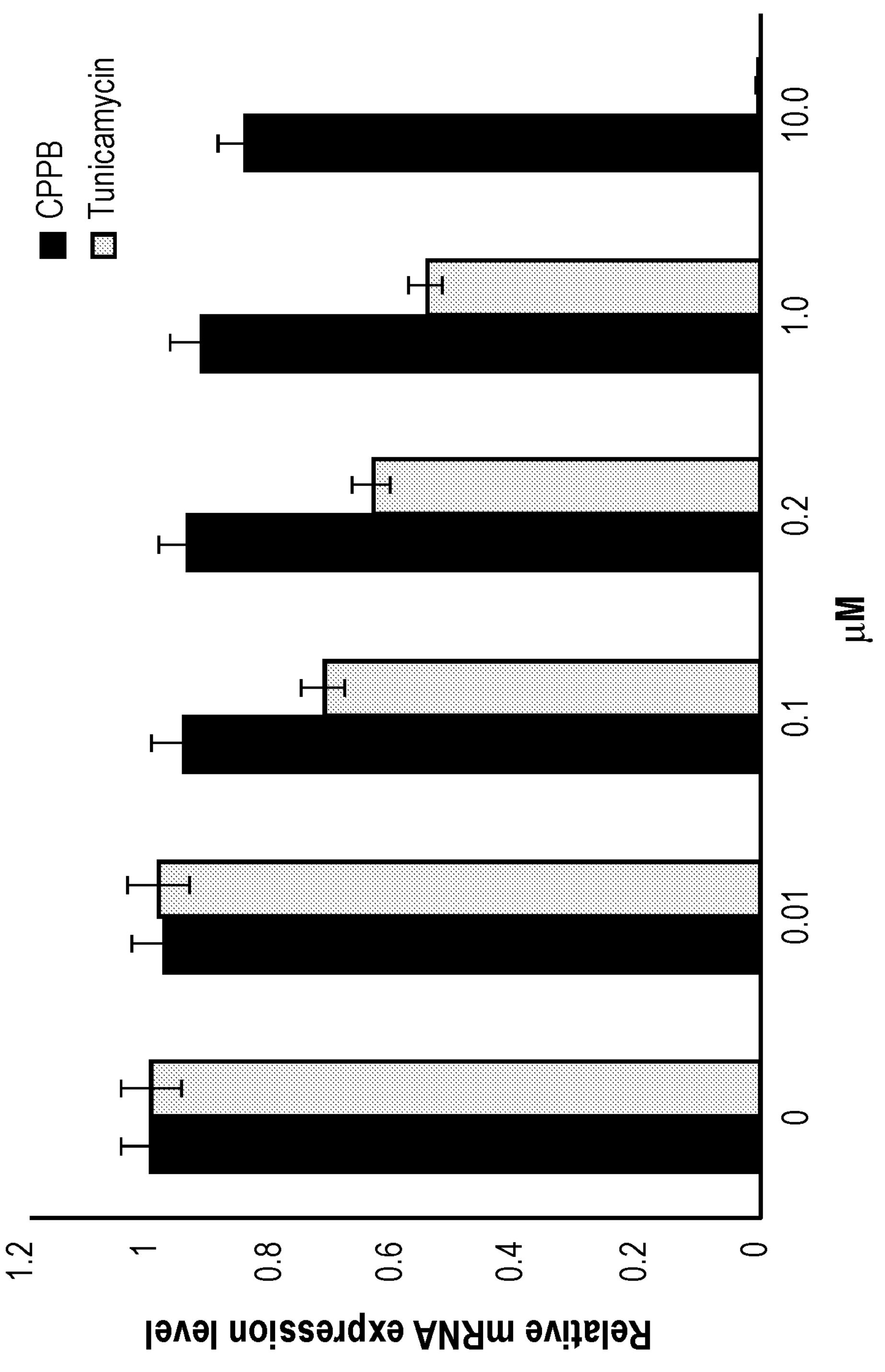
FIG. 9 shows RT-qPCR analyses of DPAGT1 expression level in PD002 treated with CPPB.

Migration inhibition observed in the scratched assays (FIG. 3) is well-correlated with the degree of the DPAGT1 expression inhibition. Although CPPB decreased the protein expression of DPAGT1 without significantly decreasing its gene (DPAGT1) expression, tunicamycin decreased both the gene expression of DPAGT1 and DPAGT1 protein expression (FIG. 9). These down-regulation in DPAGT1 gene expression by tunicamycin may be attributable to its high cytotoxicity against mammalian cells without selectivity.

Example 7: Synergistic Effect of CPPB with Paclitaxel

The FOLFIRINOX (a combination of folinic acid, 5-fluorouracil, irinotecan, and oxaliplatin) and nab-paclitaxel (albumin-bound paclitaxel)-gemcitabine regimens have been adopted into clinical practice for patients with metastatic pancreatic cancers. Median progression-free survival was reported in one study of patients with metastatic pancreatic cancer to be 6.4 months in the FOLFIRINOX group and 3.3 months in the gemcitabine group. Over the past years, the clinical data have not supported that FOLFIRINOX is associated with any better (or worse) survival rates compared to the nab-paclitaxel-gemcitabine regimen as there have been no head-to-head trials. However, the inclusion of paclitaxel and its derivatives in combination regimens remains an important therapeutic strategy in pancreatic cancer chemotherapy since nab-paclitaxel-gemcitabine is associated with less adverse effects (toxicity in patients) than FOLFIRINOX.

The synergistic or antagonistic activities of CPPB were assessed in vitro via checkerboard technique. In these experiments, CPPB displayed strong synergistic effects with paclitaxel in a wide range of concentrations against PD002. Table 3 summarizes the results of FIC index analyses for selected combinations of CPPB ($IC_{50}$ 35.0 μM) plus paclitaxel ($IC_{50}$ 1.25 μM) that showed synergistic combination (ΣFIC<0.5). The FIC index below 0.50 was observed for 20 combinations of two molecules out of 96 different concentrations (see Supporting Information). The $IC_{50}$ value of paclitaxel against PD002 was lowered (0.024-0.61 μM) in combination with CPPB (0.1-2.0 μM).

TABLE 3

| Entry | Combination of A and B | IC50 (μM) CA and CB | ΣFIC |
|---|---|---|---|
| 1 | A: CPPB | 0.10 | 0.50 |
| | B: Paclitaxel | 0.63 | |
| 2 | A: CPPB | 0.10 | 0.13 |
| | B: Paclitaxel | 0.16 | |
| 3 | A: CPPB | 0.20 | 0.0096 |
| | B: Paclitaxel | 0.0049 | |
| 4 | A: CPPB | 0.20 | 0.021 |
| | B: Paclitaxel | 0.020 | |
| 5 | A: CPPB | 0.20 | 0.26 |
| | B: Paclitaxel | 0.031 | |
| 6 | A: CPPB | 2.0 | 0.021 |
| | B: Paclitaxel | 0.020 | |
| 7 | A: CPPB | 2.0 | 0.037 |
| | B: Paclitaxel | 0.039 | |
| 8 | A: CPPB | 2.0 | 0.26 |
| | B: Paclitaxel | 0.31 | |

CPPB showed ~7.5 times stronger DPAGT1 inhibitory activity than tunicamycin. However, unlike tunicamycin, CPPB did not inhibit growth of cancer cell lines at the $IC_{50}$ values observed for tunicamycin (0.45-7.5 μM). CPPB is a cell-permeable molecule which was demonstrated by IncuCyte® live cell analyses and immunofluorescence assays. The effectiveness of CPPB on the expression levels of Snail, E-cadherin, and DPAGT1 primary in pancreatic cancers has been shown in the present disclosure. CPPB decreased the Snail expression in commercially available pancreatic cancer cell lines (PANC-1, AsPC-1, and Capan-2) and a patient-derived pancreatic ductal adenocarcinoma cell line (PD002) in a dose dependent manner. On the other hand, the E-cadherin expression level was not noticeably changed in PD002 or slightly increased in Panc-1 at between 0.05-0.2 μM of CPPB. These biochemical data support that a selective DPAGT1 inhibitor, CPPB, is effective in inhibiting migrations of the pancreatic cancer cells in migration (scratch) assays. Other than pancreatic cancers, a lower DPAGT1 expression cell, a colorectal adenocarcinoma (HCT-116) and a higher DPAGT1 expression cell, a cervical carcinoma (SiHa) were examined. CPPB did not inhibit migration of HCT-116, but strongly inhibited migration of SiHa in scratch assays at its $IC_{50}$ concentration (0.2 μM against DPAGT1).

These observations were supported by the biochemical analyses of the Snail and E-cadherin expression levels. Snail plays an important role in cancer progression. The accumulated evidence on Snail indicates that over-expression of Snail promotes drug resistance, tumor recurrence and metastasis. Snail inhibitory activity of CPPB suggests that selective DPAGT1 inhibitors have the potential to develop into less toxic anticancer therapeutics than current anticancer agents that are cytotoxic to all dividing cells in the body.

CPPB is not cytotoxic against a series of cancer and healthy cell lines at 10 μM or higher concentrations. However, it showed a strong synergistic effect with paclitaxel; cytostatic activity of paclitaxel is improved over 250-times against PD002 in combination with CPPB (0.2-2.0 μM).

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A compound of Formula I:

(I)

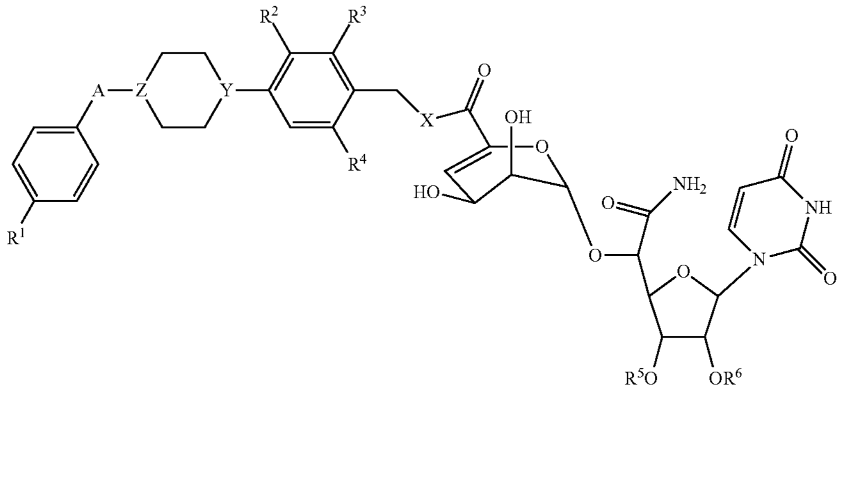

or a pharmaceutically acceptable salt thereof;

wherein

X is NH, O, or $-(CH_2)_m-$;

Y is CH or N;

Z is CH or N;

A is absent, O, or NH;

$R^1$ is $OR^7$ or $-(CH_2)_nNHR^7$;

$R^2$ is H or halo;

$R^3$ is selected from the group consisting of H, halo, $C_1$-$C_6$ alkyl, $C_2$-$C_6$ alkenyl, $C_2$-$C_6$ alkynyl, $C_1$-$C_6$ alkoxy, and $C_1$-$C_6$ haloalkyl;

$R^4$ is H or halo;

$R^5$ and $R^6$ are each independently selected from the group consisting of H, $C_1$-$C_6$ alkyl, and $C(O)C_1$-$C_6$ alkyl;

$R^7$ is selected from the group consisting of H, $C_1$-$C_6$ alkyl, $C_1$-$C_6$ haloalkyl, $C_6$-$C_{10}$ aryl, and 5-10 membered heteroaryl, wherein the aryl and heteroaryl are each optionally substituted one, two, or three times with $OC_1-C_6$ haloalkyl; and m and n are, independently at each occurrence, 0, 1, 2, or 3.

2. The compound of claim 1, wherein the compound of Formula I is a compound of Formula II:

(II)

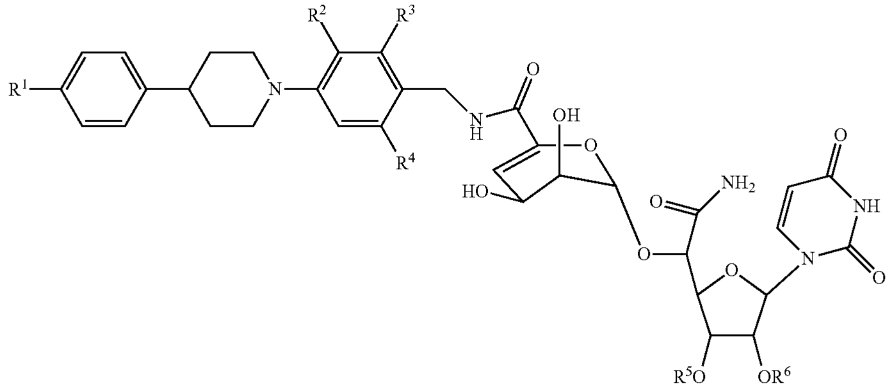

or a pharmaceutically acceptable salt thereof.

3. The compound of claim 1, wherein the compound of Formula I is a compound of Formula III:

(III)

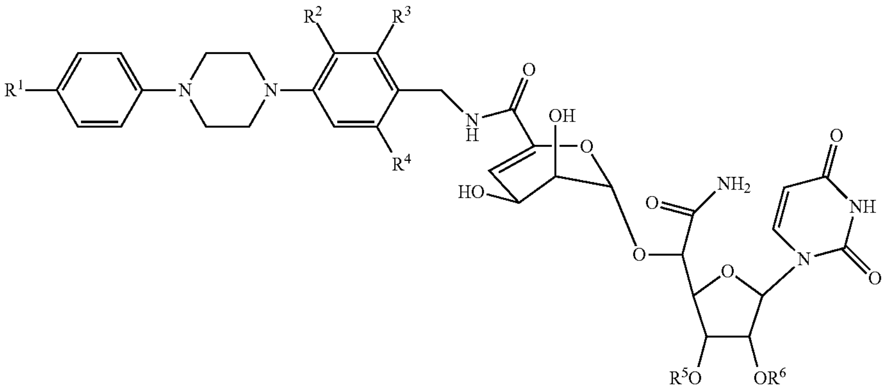

or a pharmaceutically acceptable salt thereof.

4. The compound of claim 1, wherein the compound of Formula I is a compound of Formula IV:

(IV)

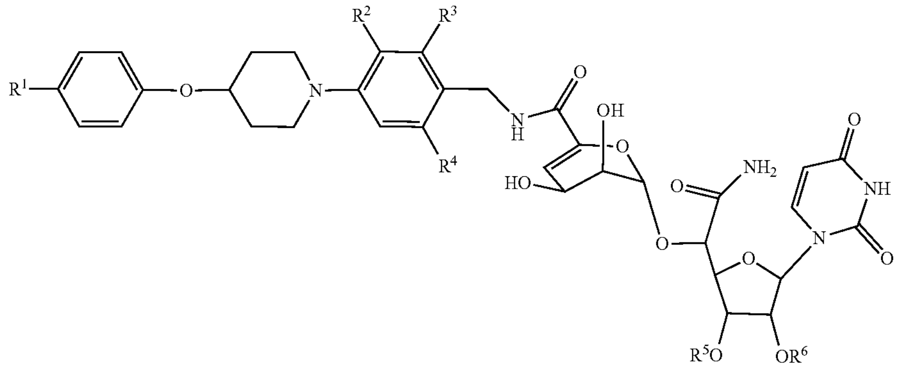

or a pharmaceutically acceptable salt thereof.

5. The compound of claim 1, wherein $R^1$ is $OR^7$.

6. The compound of claim 1, wherein $R^1$ is $-(CH_2)_n NHR^7$.

7. The compound of claim 1, wherein the compound of Formula I is CPPB:

(CPPB)

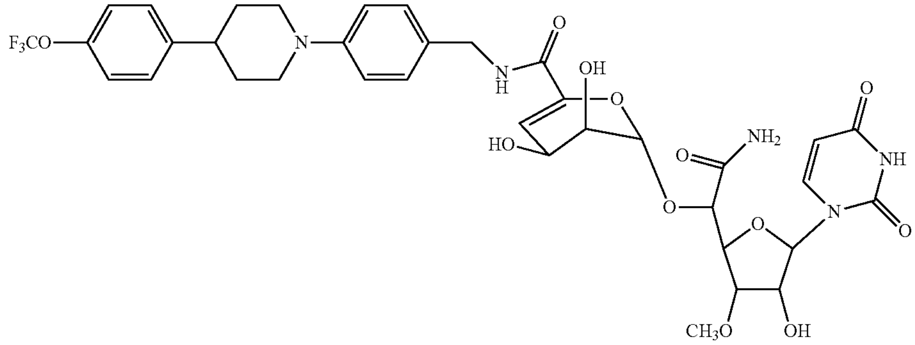

or a pharmaceutically acceptable salt thereof.

8. The compound of claim 7, wherein the compound of Formula I is CPPB1:

(CPPB1)

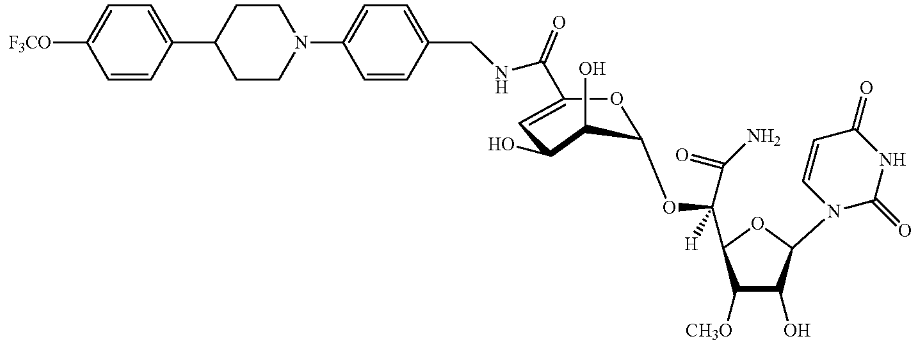

or a pharmaceutically acceptable salt thereof.

9. A pharmaceutical composition comprising the compound of claim 1, and at least one pharmaceutically acceptable carrier.

10. The pharmaceutical composition of claim 9, further comprising an additional therapeutic agent.

11. The pharmaceutical composition of claim 10, wherein the additional therapeutic agent is selected from the group consisting of paclitaxel, tunicamycin, capuramycin, erlotinib, capecitabine, fluorouracil, and gemcitabine.

12. A method of inhibiting dolichyl-phosphate N-acetylglucosaminephosphotransferase (DPAGT1) in a subject in need thereof, comprising administering to the subject a therapeutically effective amount of the compound of claim 1.

13. A method of treating cancer in a subject in need thereof, comprising administering to the subject a therapeutically effective amount of the compound of claim 1.

14. The method of claim 13, wherein the cancer is selected from the group consisting of pancreatic cancer, cervical cancer, brain cancer, colon cancer, ovarian cancer, breast cancer, carcinoma, and adenocarcinoma.

15. The method of claim 14, wherein the cancer is pancreatic cancer.

16. The method of claim 13, wherein the cancer is a solid tumor.

17. A compound of Formula V:

(V)

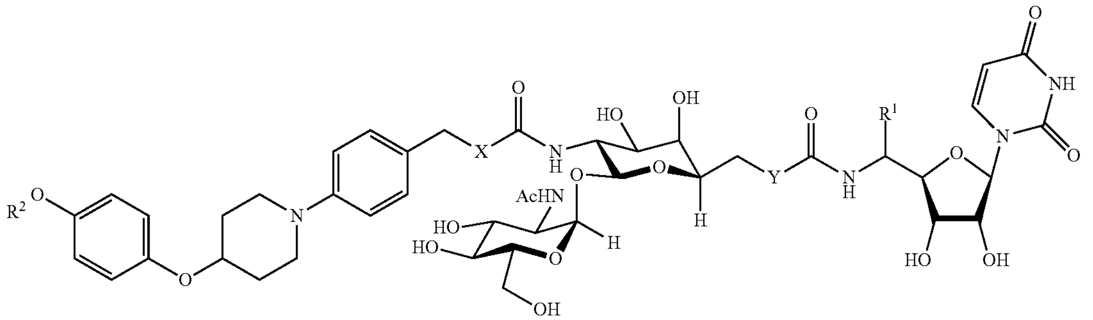

or a pharmaceutically acceptable salt thereof; wherein

X and Y are independently O or NH;

R1 is selected from the group consisting of H, OH, C(O)NH2, CO2H, C(O)H, and C(O)halo; and R2 is selected from the group consisting of H, C1-C6 alkyl, C1-C6 haloalkyl, C6-C10 aryl, and 5-10 membered heteroaryl.

18. A compound of Formula VI:

(VI)

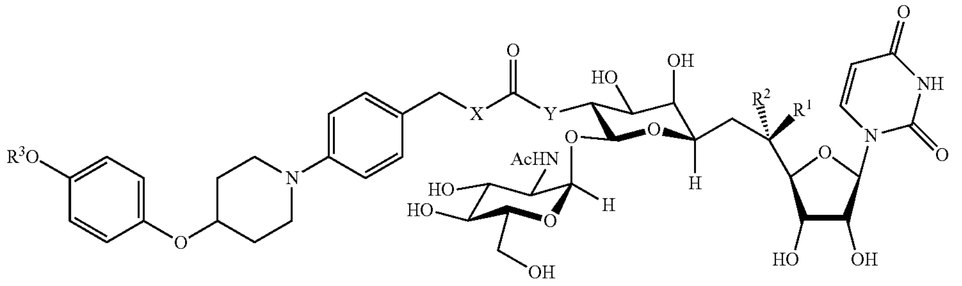

or a pharmaceutically acceptable salt thereof; wherein

X and Y are independently O or NH;

$R^1$ and $R^2$ are each independently selected from H and OH; and $R^3$ is selected from the group consisting of H, $C_1$-$C_6$ alkyl, $C_1$-$C_6$ haloalkyl, $C_6$-$C_{10}$ aryl, and 5-10 membered heteroaryl.

* * * * *